US006531136B1

United States Patent
(12) United States Patent
Studdert et al.

(10) Patent No.: US 6,531,136 B1
(45) Date of Patent: Mar. 11, 2003

(54) EQUINE RHINOVIRUS 1 PROTEINS

(75) Inventors: Michael J Studdert, Parkville (AU); Brendan S Crabb, Parkville (AU); Li Feng, Pittsburgh, PA (US)

(73) Assignee: The University of Melbourne, Parkville (AU)

(*) Notice: Subject to any disclaimer, the term of this patent is extended or adjusted under 35 U.S.C. 154(b) by 20 days.

(21) Appl. No.: 09/660,541

(22) Filed: Sep. 12, 2000

Related U.S. Application Data

(62) Division of application No. 09/091,219, filed as application No. PCT/AU96/00815 on Dec. 18, 1996, now Pat. No. 6,171,592.

(30) Foreign Application Priority Data

Dec. 18, 1995 (AU) ........................................... PN 7201

(51) Int. Cl.[7] ....................... A61K 39/12; A61K 39/245

(52) U.S. Cl. ............................... 424/199.1; 424/204.1; 424/229.1; 435/320.1; 435/325; 435/235.1; 435/91.1; 435/91.33; 435/69.1

(58) Field of Search .......................... 424/204.1, 199.1, 424/229.1; 435/69.1, 91.1, 91.33, 235.1, 320.1, 325

(56) References Cited

PUBLICATIONS

Newman, J.F.E. et al.: "Physicochemical characterization of two serologically unrelated equine rhinoviruses" Intervirology, vol. 8, 1977, pp. 145–154, XP000945104, pp. 147–153.

Campbell, T.M. et al.: "Immunogenicity of equiine herpesvirus type 1 (EHV1) and equine rhinovirus type 1 (ErhV1) following inactivation by betapropiolactone (BPL) and ultraviolet (UV) light" Veterinary Microbiology, vol. 7, No. 6, 1982, pp. 535–544, XP000972810, pp 538–543, 'Results' and 'Discussion' tables V–VII.

EMBL Database; EMBL: FMDNPCAP; Accession–No.: M55287, XP002157237.(Jul. 9, 1992).

De Boer, G. F. et al.: "Prevalence of antibodies to equine viruses in the Netherlands", The Veterinary Quarterly, vol. 1, No. 2, 1979, pp. 65–74, XP000972838, pp. 66–72, 'Assays for antibody' and 'Results' table 7.

Ditchfield et al., "The properties and classifications of two new rhinoviruses recovered from horses in Toronto, Canada", pp. 181–189, (1965).

Li et al., "Equine rhinnovirus 1 is more closely related to foot–and–mouth disease virus than to other Picomaviruses", Proc. Nat'l. Acad. Sci., vol. 93:990–995, (1996).

Wutz et al., "Equine rhinovirus serotypes 1 and 2: relationship to each other and to aphthoviruses and Cardioviruses", Journal of General Virology, vol. 77:1719–1730, (1996).

Forss et al., Nucleic Acid Research, 1984, vol. 12, No. 16, pp. 6587–6601.

*Primary Examiner*—Ali R. Salimi
(74) *Attorney, Agent, or Firm*—Foley & Lardner

(57) ABSTRACT

A determination of the nucleotide sequence for the genome of Equine rhinovirus 1 (ERhV1), a horse-respiratory pathogen of heretofor uncertain taxonomic status, reveals a structure and predicted amino acid sequence that are more similar to those of foot-and-mouth disease viruses, the only members of the aphthovirus genus, than of other picornaviruses. These insights inform an understanding of ERhV1 virion proteins and virus-like particles, as well as the design of probes, primers, antigens, vectors, diagnostics and tests of relevance to ERhV1.

5 Claims, 19 Drawing Sheets

```
-790                    -770                    -750
TAAGTAAAACGCTGTAACTGCATGATTTGCGCCTGTAGCGCCAGTAAAACGCAGAAACCA
-730                    -710                    -690
CAAGCAAAAACCTGTAGCGTCAGTAAAACGCGCACATTCACATACAGAGCTTCCCGGCTT
-670                    -650                    -630
TAAGGGTTACTGCTCGTAATGAGAGCACATGACAACTTGTCGAGATTACGGCAACTGTCA
-610                    -590                    -570
CGGGAGAGAGGAGCCCGTTTTCGGGCACTTGTCTCCTAAACAATGTTGGCGCGCATTTGC
-550                    -530                    -510
GCGCCCCCCCCCTTTTTCAGCCCCCTGTCATTGACTGGTCGAAGCGTTCGCAATAAGACT
-490                    -470                    -450
GGTCGTCACTTGGCTGTTCTATCGTTTCAGGCTTTAGCGCGCCCTTGCGCGGCGGGCCGT
-430                    -410                    -390
CAAGCCCGTGCGCTGTATAGCGCCAGGTAACCGGACAGCGGCGTGCTGGATTTTCCCGGT
-370                    -350                    -330
GCCATTGCTCTGGATGGTGTCACCAAGCTGACAAATGCGGAGTGAACCTCACAAAGCGAC
-310                    -290                    -270
ACGCCTGTGGTAGCGCTGCCCAAAAGGGAGCGGAACTCCCCGCCGAGGCGGTCCTCTCTG
-250                    -230                    -210
GCCAAAAGCCCAGCGTTGATAGCGCCTTTTGGGATGCAGGAACCCCACCTGCCAGGTGTG
-190                    -170                    -150
AAGTGGAGTGAGCGGATCTCCAATTTGGTCTGTTCTGAACTACACCATTTACTGCTGTGA
-130                    -110                    -90
AGAATGCCCTGGAGGCAAGCTGGTTACAGCCCTGACCAGGCCCTGCCCGTGACTCTCGAC
 -70                     -50                    -30
CGGCGCAGGGTCAAAAATTGTCTAAGCAGCAGCAGGAACGCGGGAGCGTTTCTTTTCCTT
 -10                     10                     30
TTGTACTGACATGATGGCGGCGTCTAAGGTGTATAGAGTTTGCGAGCAGACTCTGCTGGC
          M   A   A   S   K   V   Y   R   V   C   E   Q   T   L   L   A
 50                      70
AGGTGCCGTTCGCATGATGGACAAA
 G   A   V   R   M   M   D   K
```

FIG. 2B

```
FMDVO1K    1  MNTTDCFIALVQAIREIKALFLSRTTGKMELTLYNGEKKTFYSRPNNHDN-CWLNAILQL   59
              :* .: **   *:.  :  :*  :   .*****     .:: . :***** *********
ERhV1      1  MAASKVYRVCEQTLLAGAVRMDKFLQKRTVFVPHLDKTIRLTGLHNYDNTCWLNALTQL   60

FMDVO1K   60  FRYVEEPFFDWVYSSPENLTLEAIKQLEDLTGL-ELHEGGPPALVIWNIKHLLHTGIGTA  118
              : .: ****:.  :* :* ****  *::: *  *  .*.**********  *:* :**
ERhV1     61  TQILGIRLFDEHFGNRGLFTRKTIDWSDQTGIKDLKSGAPPLVVVYKLWQHGHLDVGTM  120

FMDVO1K  119  SRPSEVCMVDGTDMCLADFHAGIFLKGQEHAVFACVTSNGWYAIDDEDFYPWTPDPSDVL  178
              .*:****** ***.***  .*  *:* *:*******  :.*.  ..*:: :* ** ***
ERhV1    121  EKPRSITLWSGPKVCLSDFWACVSAK-PGHAVFYLLTSEGWICVDDKKIYPETPKTEDVL  179
                                      L↓VP4
FMDVO1K  179  VFVPYDQEPLNGEWKAKVQR----KLKGAGQSSPATGSQNQSGNTGSIINNYMQQYQN  233
              ** ***:*  *   .  *: *   * .:.. :.:*.. :. : .:.:.:* ******
ERhV1    180  VFAPYDFESLGKDPPKLHQRYEKAFELSGGTSTPTTGNQMSGNSGSIVQNFYMQQYQN  239
                                     L↓VP4
FMDVO1K  234  SMDTQLGDNAISGGSNEGSTDTTSTHTTNTQNNDWFSKLASSAFSGLFGALLADKKTEET  293
              *:*   *** :: **  * **** **.:...:   *             ********
ERhV1    240  SIDADLGDNVISPEGQGSNTSSSSSTSSSQSSGLGGWFSSLL-----NLGTKLLADKKTEET  294
                                                              VP4↓VP2
FMDVO1K  294  TLLEDRILTTRNGHTTSTTQSSVGVTYGYATAEDFVSGPNTSGLETRVVQAERFFKTHLF  353
              * **** *** :*.*** *:***** **:** ***:*** .*::*::::::. :::::
ERhV1    295  TNIEDRIETTVGVTIINSQGSVGTTYCYSKPDGRPPSTVSDPVTRLGPTLSRHYTFKVG  354

FMDVO1K  354  DWVTSDSFGRCHLLELPTDHKGVYGSLTD---SYAYMRNGWDVEVTAVGNQFNGGCLLVA  410
              :*: :** *   * ****.*:::.  ***:  .:**:***..* ******   *****
ERhV1    355  EWPHSQSHGHAWICPLPGDKLKKMGSFHEVVKAHHLVKNGWDVVVQNPSFAHSGPLCVA  414

FIG. 3A
```

```
FMDVO1K  411  MVPELYSIQKREL------------YQLTLFPHQFINPRTNMTAHITVPFVGVNRYDQYK  458
              ***           .:    :  **  .::**.*
ERhV1    415  AVPEYEHTHEKALKWSELEEPAYTYQQLSVFPHQLLNLRTNSSVHLVMPYIGPGQPTNLT  474
                                              VP2 ↓ VP3
FMDVO1K  459  VHKPWTLVVMVVAPLTVNTEGAPQIKVYANIAPTNVHVAGEFPSKEGIFPVACSDGYGGL  518
              :*.****.*:::  *: * :*  :*  : :* * .: ::
ERhV1    475  LHNPWTIVILILSELTGPGQTVP---VTMSVAPIDAMVNGPLPNPEAPIRVSVPESDSF  531
                                                   VP2 ↑ VP3
FMDVO1K  519  VTTDPKTADPVYGKVFNPPRNQLPGRFTNLLDVAEACPTFLRFEGGVPYVTTKTDSDRVL  578
              :   * :  ****** ***:::****** ***** *    *.:  .   *  ::*.**
ERhV1    532  MSSVPDNSTPLYPKVVVPPR-QVPGRFTNFIDVAKQTYSFCSISGKPYFEVTNTSGDEPL  590
              *
FMDVO1K  579  AQFDMSLAAKQMSNTFLAGLAQYYTQYSGTINLHFMFTGPTDAKARYMVAYAPPGMEPPK  638
              :*::*:*::  *  *:  **   ::   ::      .*  : *
ERhV1    591  FQMDVSLSAAELHGTYVASLSSFFAQYRGSLNFNFIFTGAAATKAKFLVAFVPPHSAAPK  650
                                                                       ***
FMDVO1K  639  TPEAAAHCIHAEWDTGLNSKFTFSIPYLSAADYAYTASGVAETTNVQGWVCLFQITHGKA  698
              *.::*** **.:**.****.**.:  ::::** *
ERhV1    651  TRDEAMACIHAVWDVGLNSAFSFNVPYPSPADFMAVYSAERTVVNVSGLQVYALTALTS  710
                                          VP3 ↓ VP1
FMDVO1K  699  DGDA----LVVLASAGKDFELRLPVD-ARAETTSAGESADPVTTTVENYGGETQIQRR  751
              : :     : :.** *:**   *                  .  .
ERhV1    711  TDIAVNSKGRVLVAVSAGPDFSLRHPADLPDKQVTNVGEDGEPGETEPRH--ALSPVDMH  768
                                                  VP3 ↑ VP1
FMDVO1K  752  QHTDVSFIMDRFVKV-------TPQNQINILDLMQIPSHTLVGALLRASTYYFSDLEIA  803
              .*:*.*::.**:** **:
ERhV1    769  VHTDVSFLLDRFFDVETLELSNLTGSPATHVLDPFGSTAQLAWARLLNTCTYFFSDLELS  828
```

FIG. 3B

```
FMDVO1K  804  VKHEGDLT--------WVPNGAPEKALDNTTNPTAYHKAPLTRLALPYTAPHRVL-  850
              :.: *       *.* ****.* *     *..
ERhV1    829  IQFKFTTTPSSVGEGFWVKWLPVGAPTKTTDAWQLEGGNSVRIQKLAVAGMCPTVVFK  888

FMDVO1K  851  --------ATVYNGECRYNRNAVPNLRGDLQVLAQKVAR-----TLPTSFNYGAIKATR  896
                      : * :.: .:   :                   ****.**  :
ERhV1    889  IAGSRSQACASALPYTSMWRVVPVFYNGWGAPTKEKATYNWLPGAHFGSILLTSDAHDKG  948
                                                               VP1 ↓ 2A     2B
FMDVO1K  897  VTELLYRMKRAETYCPRPL-LAIHPTEARHKQKIVAPV-KQTLNFDLLKLAGDVESNPGP  954
              * * ::.::: :   :                     *  ** ****************
ERhV1    949  GCYLRYAFRAPAMYCPRPIPPAFTRPADKTRHKFPTNINKQCTNYSLLKLAGDVESNPGP 1008
                                                               VP1 ↑ 2A     2B

FMDVO1K  955  FFFSDVRSNFSKLVETINQMQEDMSTKHGPDFNRLVSAFEELAIGVKAIRTGLDEAKPWY 1014
              : **                                      *  :.:: :      *
ERhV1    1009 TIFS-----------------------KASADLNALSTSLGELTGMLKDLKAKAETYSPFY 1046

FMDVO1K  1015 KLIKLLSRLSCMAAVAARSKDPVLVAIMLADTGLEILDSTFVVKKISDSLSSLFHVPAPV 1074
              *:: :.:: .  :.: : *  ****** * ..* :* **: :
ERhV1    1075 FS---FGAPVLLAGLVKVASSFFRSTPEDLE-RAEKQLKARDINDIFAILKNGEWLVKLI 1130
                                                                    2B ↓ 2C
FMDVO1K  1075 KMAKMLFKLATLAVAAMRTKDPVVVMLIADFGLEVFDTGFFFSYFQEKLQPYMKTIPGK  1166
              *  :::*: :.:: :: *  ***  :: *:  ** *** * *:::  :. *:** :.
ERhV1    1107 ISDLVTDAATAAAQIPKGVYSFVSSFFETPEGVVEKQVSLRTVNDIFALLKNSDWFIKTL 1166
                                                                    2B ↑ 2C
FMDVO1K  1131 LAIRDWIKAWIASEEKF-VTMTDLVPGILEKQRDLNDPSKYKEAKEWLDNARQACLKSGN 1189
              :*::*::::* :*..::   * * *  :. *::*.*   :: :::: * :::  :*.
ERhV1    1167 VALKKWLTSWFAQEQQADDALYSELEKYPLYKLKLKEPDTQEEARQWFKDMQQRALAVKD 1226
```

FIG. 3C

```
FMDV01K  1190  VHIANLCKVVVAPAPSKSRPEPVVCLRGKSGQGKSFLANVLAQAISTHFTGRIDSVWYCP   1249
               :  *::  :..::* *:**** ****.**********:****  : ****** ****
ERhV1    1227  KGLFSLLQIPLVNLPQSRPEPVVCVLRGASGQGKSYLANLMAQAISLLLVGKQDSVWSCP   1286

FMDV01K  1250  PDPDHFDGYNQQTVVVMDDLGQNPDGKDFKYFAQMVSTTGFIPPMASLEDKGKPFNSKVI   1309
               *** .:* ****.**::*: * :*.*: ***:**:*:.**:**** :****:***.***
ERhV1    1287  PDPTYFDGYNGQAVVIMDALGQDPNGADFKYFCQMVSTTAFVPPMAHLDDKGIPFTSPVV   1346

FMDV01K  1310  IATTNLYSGFTPRTMVCPDALNRRFHFDIDVSAKDGY----KINSKLDIIKALEDTHANP   1365
               * ****:**:*: *: *  *:*** *:   :*.*:        ..  :: ** :     
ERhV1    1347  ICTTNLHSSFTPITVSCPEALKRRFRFDVTVSAKPGFVRTVGSNQLLNLPLALKPAGLPP   1406
                                                                          2C↓
FMDV01K  1366  VAMFQYDCALLNGMAVEMKRMQQDMFKPQPPLQNVYQLVQEVIDRVELHEKVSSHPIFKQ   1425
                : : ::  :  ..**:*:*:   :: *:  *                  * ****:**
ERhV1    1407  HPIFENDMPIINGQAVKLALSGGEV------TAFELIEMILSEVQNRQDTHKMPIFKQ    1458
                                                                          2C↓

FMDV01K  1426  ISIPSQKSVLYFLIEKGQHEAAIEFFEGMVHDSIKEELRPLIQQTSFVKRAFKRLKENFE   1485
               : * : *: :: : :   :::*   :  * :::*::  *      .: *:*.:: ***:
ERhV1    1459  SWSD------LFRKCTTDEEQKMLQFLIDNKDSEILRAFVSERSILLHEEYLKWESYM    1510

FMDV01K  1486  IVALCLTLLANIVIMIRETKRQKMVDDAVNEYIEKANITTDDKTLDEAEKSPLETSGAS   1545
               : :   *: ::  :  *  :: :  ::     *  : *:*  : ::*  :.* :  *
ERhV1    1511  TRRAKFHRLAADFAMFLSILTSLIVIFCLVYSMYQLFKTPDEQSAYDPSTKPKTQEVK   1570
                                                      3A↓3B      3A↓3B

FMDV01K  1546  TVGFRERTLPGQKACDDVNSEPAQPVEEQPQAEGPYAGPLERQKPLKVRAKLPQQEGPYA   1605
               *. :* *
ERhV1    1571  TLKIR-------------------------------------------------------   1575
                                                                          3B↓
                                                                     3A↓

FIG. 3D
```

```
                             3A ↓ 3B                          3B ↓ 3C
FMDVO1K  1606 GPMERQKPLKVKAKAPVVKEGPYEGPVKKPVALKVKAKNLIVTESGAPPTDLQKMVMGNT 1665
                                                        **.*.*:****.  :* *.
ERhV1    1576 -----------------------------------------TETGVPATDLQQSIMKNV 1593
                                                              3B ↑ 3C

FMDVO1K  1666 KPVELILDGKTVAICCATGVFGTAYLVPRHLFAEKYDKIMVDGRAMTDSDYRVFEFEIKV 1725
               *:**.**..  *.  *:* **:::..**** ***.  .:*.*:::**   ...::  .***:.*
ERhV1    1594 QPIELYLDNELVTDCSALGVYDNSYLVPLHLFEFDFDTIVLGGRHYKKAECEKVEFELEV 1653

FMDVO1K  1726 KGQDMLSDAALMVLHRGNRVRDITKHFRDTARNKKGTPVVGVINNADVGRLIFSGEALTY 1785
               *: : ***.*:  :  .* :**:*..  *  :.   :** *.*.*::*.:.  :* :* *.  **
ERhV1    1654 NGDVVSSDACLLRVSSGPKVRNIVHLFTNEIELKKMTQVTGIMNSPHQARTVFFGSFLTV 1713

FMDVO1K  1786 KDIVVCMDGDTMPGLFAYRAATKAGYCGGAVLAKDGADTFIVGTHSAGGNGVGYCSCVSR 1845
              :. ::. **..**.::.* *.*. ****:*::*   *...  *:*.****..:*::** ***
ERhV1    1714 RKSILTSDGTVMPNVLSYAAQTSRGYCGAAIVA--GSPARIIGIHSAGTGSVAFCSLVSR 1771

3C ↓ 3D
FMDVO1K  1846 SMLLKMKAHIDPEPHHEGLIVDTRDVEERVHVMRKTKLAPTVAHGVFNPEFGPAALSNKD 1905
                *  .:.::  :.:          *.   *  : ** * *:.**...:*..:*.*::***:**.  *
ERhV1    1772 DALEQLWPQKQGN-------VSRLDDDVRVSVPRRSKLVKSLAYPIFKPDYGPAPLSQFD 1824
                        3C ↑ 3D

FMDVO1K  1906 PRLNEGVVLDEVIFSKHKGDTKMSEEDKALFRRCAADYASRLHSVLGTANAPLSIYEAIK 1965
               **.:** ****:*.**.**..:*.:*.  :: *.*   ** :: *  :* .*.:*.   ***
ERhV1    1825 KRLSDGVKLDEVVFAKHTGDKEISAQDQKWLLRAAHVYAQKVFSRIGFDNQALTEKEAIC 1884

FMDVO1K  1966 GVDGLDAMEPDTAPGLPWALQGKRRGALIDFENGTVGPEVEAALKLMEKREYKFVCQTFL 2025
              *:.*** **.*******:* *.***  .:.***:*  :  ..          ::*.      .:*:*.**
ERhV1    1885 GIPGLDKMEQDTAPGLPYAQQNKRRKDICDFEEGRLKGAELQKDRFMAGDYSNLVYQSFL 1944
```

FIG. 3E

```
FMDV01K  2026  KDEIRPLEKVRAGKTRIVDVLPVEHILYTRMMIGRFCAQMHSNNGPQIGSAVGCNPDVDW  2085
               ************::*:::..*.::::..*  :::..*  ..:::*  :*:****
ERhV1    1945  KDEIRPLEKVRAGKTRLIDVPPMPHVVVGRQLLGRFVAKFHEANGFDIGSAIGCDPDVDW  2004

FMDV01K  2086  QRFGTHFAQYRNVWDVDYSAFDANHCSDAMNIMFEEVFRTEFGFHPNAEWILKTLVNTEH  2145
               ***.:::*.**.:::***  *****.:***..*:::.*..*:..**:*
ERhV1    2005  TRFGLELERFRYVYACDYSRFDANHAADAMRVLNYFFSEDHGFDPGVPAFIESLVDSVH  2064

FMDV01K  2146  AYENKRITVGGGMPSGCSATSIINTILNNIYVLYALRRHYEGVELDTYTMISYGDDIVA  2205
               ****:.*.:.****.*.:****.:****:*****..*..*::*.:..*:****
ERhV1    2065  AYEEKRYNIYGGLPSGCSCTSILNTILNNVYILAAMMKAYENFEPDDIQVICYGDDCLIA  2124

FMDV01K  2206  SDYDLDFEALKPHFKSLGQTITPADKSDKGFVLGHSITDVTFLKRHFHMDYGTGFYKPVM  2265
               **:..:**.*  *  * ****.*..:*:****  ..:::******.**
ERhV1    2125  SDFEIDFQQLVPVFSSFGQVITTADKTD--FFKLTTLSEVTFLKRAFVL--TAFYKPVM  2179

FMDV01K  2266  ASKTLEAILSFARRGTIQEKLISVAGLAVHSGPDEYRRLFEPFQGLFEIPSYR  2318
               .**:****:***.**:*****.**:***::****  *:****:*****
ERhV1    2180  DVKTLEAILSFVRPGTQAEKLLSVAQLAGHCEPEQYERLFEPFAGMYFVPTWR  2232
```

FIG. 3F

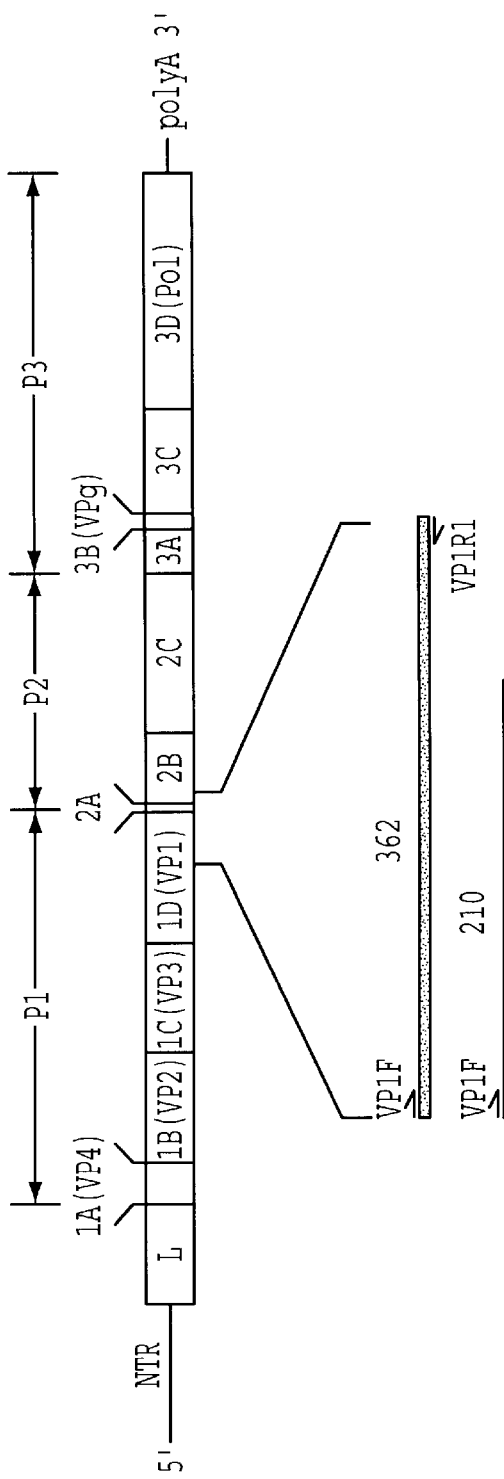

EQUINE RHINOVIRUS 1 PROTEINS

This application is a divisional of application Ser. No. 09/091,219, filed Oct. 5, 1998, now U.S. Pat. No. 6,171,592, which is a National Stage of PCT/AU06/00815, filed Dec. 18, 1996, based on Australian Application No. PN 7201, filed Dec. 18, 1995.

INTRODUCTION TO INVENTION

This invention relates to the equine rhinovirus 1 (ERhV1) which has been sequenced and characterized. In particular, the invention relates to nucleotide and protein sequences of ERhV1 and a range of clinical and diagnostic products derived from ERhV1.

BACKGROUND OF INVENTION

Equine rhinovuris 1 (ERhV1) was first isolated from horses in the United Kingdom and subsequently from horses in mainland Europe, the USA and Australia. Most isolates were from the nasopharynx of horses with an acute, febrile respiratory disease. Virions had the characteristic size and morphology of picornaviruses and were acid-labile. Two other serologically distinct, acid-labile picornaviruses, ERhV2 and ERhV3, have also been isolated from horses.

Considerable uncertainity has surrounded the classification of ERhV1. Physicochemical studies have shown that the nucleic acid density and base composition of ERhV1 differ from those of rhinoviruses. In contrast to rhinoviruses, ERhV1 has a broad host-cell range in vitro and in vivo and there is no evidence of extensive antigenic variation. Infection of horses with ERhV1 causes a disease characterized by an acute febrile respiratory disease accompanied by anemia, fecal and urine shredding and viral persistance. The signs of systemic infection and persistance are not characteristic of rhinovirus infections in other species. The known host range of ERhV1 is broad and includes rabbits, guinea pigs, monkeys and humans, although in these species the virus does not appear to spread horizontally. There is both experimental and epidemiological evidence of ERhV1 infection of humans. A human volunteer inoculated intranasally with ERhV1 developed severe pharyngitis, lymphadenities, fever and viremia, and high ERhV1 antibody titers were found in the sera of 3 of 12 stable workers whereas no ERhV1 antibody was found in the sera of 159 non-stable workers.

In order to clarify the taxonomic status of ERhV1, a detailed study was undertaken to determine the nucleotide and amino acid sequence of ERhV1. The resultant studies provided the complete nucleotide sequence of the gene encoding the ERhV1 polyprotein and the 3'-nontranslated region (NTR) as well as part of the nucleotide sequence of the 5'NTR. The amino acid sequence of the various ERhV1 proteins was deduced from the nucleotide sequence.

The analysis of the nucleotide sequence of ERhV1 confirmed previous studies which indicated that many properties of ERhV1 are not consistent with those of other members of the genus Rhinovirus. Indeed many of the physiochemical and biological properties of ERhV1 have suggested ERhV1 is more closely related to foot-and-mouth disease virus (FMDV) the sole member of the Alpthovirus genus. In addition to the overall sequence similarity, several features of the ERhV1 genome are similar to those of FMDV. The ERhV1 L protein is most similar to its counterpart in aphthoviruses in both length, 207 amino acids in ERhV1 and 201 and FMDV, and in amino acid sequence identity. In aphthoviruses, the L protein catalyses its own cleavage from the polyprotein, and mediates cleavage of the p220 component of the cap-binding complex leading to inhibition of translation of capped mRNAs. Cardiovirus L proteins are only 67–76 amino acids long and are not auto catalytic. In contrast to the cardioviruses, aphthoviruses utilize two distinct initiation codons, which results in different forms of the L protein, Lab and Lb, differing from each other by 28 amino acids at their N-termini.

The second initiation codon occurs in a more favourable contexts, which is presumably the reason why Lb, the smaller of the two proteins, is the predominant species. Thus far, differences in the function of the two FMDV L proteins have not been detected. ERhV1 also possesses a second ATG, 63 bases downstream from the first optimal ATG, which is also present in a context optimal for initiation of translation. Translation from this ATG would result in an L protein with 21 fewer amino acids at its N-terminus. Therefore, it is probable that ERhV1 possesses a second species of L protein similar to the FMDV Lb protein. If so, the reason for the existence and conservation of two forms of the L protein in ERhV1 and FMDV is an intriguing question. Curiously, ERhV1 has tandemly repeated ATG codons at each of the possible initiation sites, where the first ATG in each case does not occur in a context optimal for translation. The role of these ATGs may be to ensure that translation is initiated from both possible initiation sites.

The 2A protease is only 16 amino acids in length in both FMDV and ERhV1, compared to 142–149 amino acids in other picornaviruses. In FMDV 2A protease cleaves at its C-terminus but, unlike the 2A protease of other picornaviruses, appears not to have a role in shut down of host cell macromolecular synthesis. The high degree of conservation of the FMDV and ERhV1 2A proteins is intriguing and suggests an important role for this protein in the diseases produced by these viruses.

It may be expected that the tree derived from the complete polyprotein coding sequence would provide the most representative view of the taxonomic status of ERhV1 by reducing any bias imparted by using restricted parts of the genome with highly variable evolutionary rates. However, such analysis is restricted because there are only a few complete polyprotein sequences available. The polymerase genes are the most conserved genes in positive strand RNA viruses and they have been used to construct a taxonomy, and to predict the ancient roots, of these viruses. In contrast to the polymerase gene, the VPI gene encodes the major antigenic determinants of the virus and evolves more rapidly than other regions in the genome. The diversity of VP1 regions make them useful for the study of closely related picornaviruses. Thus, trees based on the polymerase and VP1 genes presumably reflect the extremes of evolutionary rates from which the taxonomic status and evolutionary origin of ERhV1 could be identified. The ERhV1 VP1 amino acid sequence was more similar to FMDV that to any other sequence in the data base; this was true even when representative segments across the entire sequence were separately analysed.

Therefore, we consider that the difference in the topology of the VP1, compared to the other two trees, is most unlikely to be a consequence of genetic recombination. The topographic differences between the three ERhV1 trees compared to those of aphthoviruses, particularly the VP1 derived trees, as well as the presence of only one VPg gene in ERhV1 genome, leads us to conclude that ERhV1 is probably a member of a distinct genus proposed to be called Equirhinovirus.

The reassessment of the taxonomic status of ERhV1 focuses on a requirement to reassess the biology of the virus particularly with respect to the nature of clinical disease as well as means for control by vaccination and improved methods of diagnosis. For example, cardioviruses and aphthoviruses cause viremic infections accompanied by myocarditis. Clinical disease caused by ERhV1 is generally considered to be confirmed to the respiratory tract even though there is a viremia and the virus is shed in faces and urine. Whether ERhV1 infection produces systemic disease similar to that observed in apthovirus or cardiovirus infections, including the production of myocarditis, needs to be investigated. There is serological evidence that the incidence of ERhV1 infection is as high as 50% in some horse populations however, the number of reported isolations of ERhV1 is very small. We have clear evidence that primary isolation of the virus from clinical specimens is known to be difficult, suggesting that the true incidence of ERhV1 disease is much greater than reported.

The determination of the complete nucleotide sequence of ERhV1 polyprotein has important practical applications in developing novel methods for the diagnosis and control of ERhV1 disease in horses and other species.

OBJECT AND STATEMENT OF INVENTION

In one aspect, the invention provides a substantially pure nucleotide sequence for ERhV1 being:

```
a substantially pure nucleotide
sequence for ERhVI (SEQ ID NO: 1) being:

CCGTCAAGCC CGTTGCCTGT ATAGCCAGGT AACCGGACAG CGGCTTGCTG GATTTTCCCG  -375

GTGCCATTGC TCTGGATGCT GTCACCAAGC TGACAAATGC GGAGTGAACC TCACAAAGCG  -315

ACACGCCTGT GGTAGCGCTG CCCAAAAGGG AGCGGAACTC CCCGCCGAGG CGGTCCTCTC  -255

TGGCCAAAAG CCCAGCGTTG ATAGCGCCTT TTGGGATGCA GGAACCCCAC CTGCCAGGTG  -195

TGAAGTGGAG TGAGCGGATC TCCAATTTGG TCTGTTCTGA ACTACACCAT TTACTGCTGT  -135

GAAGAATGCC CTGGAGGCAA GCTGGTTACA GCCCTGACCA GGCCCTGCCC GTGACTCTCG   -75

ACCGGCGCAG GGTCAAAAAT TGTCTAAGCA GCAGCAGGAA CGCGGGAGCG TTTCTTTTCC   -15

TTTTGTACTG ACATGATGGC GGCGTCTAAG GTGTATAGAG TTTGCGAGCA GACTCTGCTG    45

GCAGGTGCCG TTCGCATGAT GGACAAATTC TTGCAAAAGA GAACTGTTTT TGTCCCCCAT   105

CTTGACAAAA CAATTCGTTT GACTGGACTC CACAATTATG ACAATACTTG CTGGTTGAAT   165

GCCTTGACAC AACTGACACA GATTCTTGGA ATTCGGCTTT TTGATGAACA CTTCGGCAAT   225

AGAGGTCTGT TCACTCGGAA AACAATTGAT TGGGTGAGTG ACCAGACTGG TATAAAAGAT   285

CTAAAATCAG GAGCACCGCC ACTCGTGGTG GTGTACAAAC TGTGGCAACA TGGACACTTG   345

GATGTCGGTA CGATGGAGAA ACCCCGGTCG ATTACTCTAT GGTCTGGCCC CAAAGTGTGT   405

CTTTCTGATT TCTGGGCCTG TGTTTCGGCA AAACCGGGAC ATGCAGTATT CTACCTTCTC   465

ACAAGCGAGG GTTGGATCTG TGTTGATGAC AAGAAAATAT ACCCAGAAAC ACCCAAAACA   525

GAGGATGTAC TTGTTTTTGC GCCCTATGAC TTTGAGTCAC TGGGCAAGGA CCCACCAAAG   585

CTACACCAGA GATATGAAAA AGCATTTGAG CTCAGTGGCG GAGGTACATC CACTCCAACA   645

ACTGGCAACC AAAACATGTC CGGAAACAGT GGTTCAATTG TTCAAAATTT TTACATGCAA   705

CAGTACCAGA ATTCAATTGA CGCAGACCTC GGAGACAATG TGATTAGCCC TGAAGGCCAG   765

GGCAGCAACA CTAGTAGTTC AACCTCATCA AGCCAATCCT CTGGCTTGGG CGGGTGGTTC   825

TCTAGTTTGC TGAACCTTGG AACAAAACTA CTGGCTGACA AGAAGACAGA AGAGACTACA   885

AACATTGAAG ACAGAATTGA AACAACAGTG GTTGGAGTCA CTATTATTAA TTCACAAGGA   945

TCTGTTGGAA CAACCTACTG TTACTCCAAA CCGGATGGTA GACCACCATC CACAGTGTCA  1005

GACCCAGTTA CCAGACTTTG ACCCACGCTT TCCAGGCACT ACACATTTAA GGTAGGTGAG  1065

TGGCCCCATT CTCAATCACA TGGTCACGCA TGGATCTGTC CGTTGCCAGG TGACAAACTC  1125

AAGAAGATGG GCAGTTTTCA TGAGGTTGTC AAAGCCCACC ACCTGGTCAA GAACGGCTGG  1185

GATGTGGTTG TGCAGGTGAA TCCCTCATTT GCTCACTCCG GGCCGCTGTG TGTAGCAGCA  1245

GTGCCGGAGT ACGAACACAC ACATGAGAAA GCACTCAAGT GGTCTGAGCT TGAGGAACCA  1305

GCTTACACAT ACCAACAACT TTCAGTTTTT CCCCACCAGT TGCTAAATTT GAGGACAAAT  1365
```

-continued

```
TCATCAGTGC ATTTGGTGAT GCCCTACATT GGGCCAGGCC AACCAACAAA TCTGACTTTG    1435

CACAACCCGT GGACCATTGT TATTTTAATT TTGTCTGAAT TGACAGGACC TGGCCAAACT    1485

GTGCCTGTGA CCATGTCGGT GGCTCCCATC GATGCAATGG TTAATGGGCC TCTTCCAAAT    1545

CCAGAGGCAC CGATTAGAGT GGTGTCTGTG CCTGAATCAG ATTCTTTTAT GTCTTCAGTA    1605

CCTGATAATT CGACTCCACT ATACCCCAAG GTTGTGGTCC CACCGCGCCA AGTTCCTGGC    1665

CGGTTTACAA ATTTCATTGA TGTGGCAAAA CAGACATATT CATTTTGTTC CATTTCTGGA    1725

AAACCTTATT TTGAGGTTAC CAACACCTCT GGGGACGAGC CACTGTTTCA GATGGATGTG    1785

TCGCTCAGTG CGGCAGAGCT ACATGGCACT TACGTAGCTA GTTTGTCATC ATTTTTTGCA    1845

CAGTACAGAG GCTCACTTAA TTTCAACTTT ATTTTCACTG GTGCAGCAGC CACTAAGGCA    1905

AAGTTTCTGG TTGCTTTTGT GCCTCCCCAC AGTGCAGCGC CCAAAACGCG CGATGAAGCA    1965

ATGGCGTGCA TCCATGCCGT GTGGGATGTT GGCTTGAACT CAGCTTTTTC TTTTAATGTA    2025

CCTTATCCCT CCCCTGCTGA CTTCATGGCC GTTTATTCTG CGGAACGGAC GGTTGTGAAT    2085

GTCTCTGGAT GGCTTCAAGT TTATGCACTA ACAGCTCTAA CTTCAACTGA CATTGCCGTG    2145

AACAGTAAAG GCCGTGTGCT GGTTGCTGTT TCCGCCGGCC CAGACTTCTC CCTTCGTCAC    2205

CCGGCGGACC TGCCCGACAA GCAGGTTACC AATGTGGGAG AGGATGGTGA ACCCGGTGAG    2265

ACAGAGCCTC GTCATGCTTT GTCACCCGTG GACATGCACG TGCACACAGA TGTCAGTTTC    2325

TTGCTTGACC GGTTCTTTGA TGTTGAGACA CTTGAGCTTT CAAATTTGAC AGGTTCTCCT    2385

GCCACACATG TTCTGGATCC GTTTGGCTCG ACTGCCCAAC TGGCTTGGGC ACGTCTGCTA    2445

AACACTTGCA CCTACTTCTT TTCTGATTTG GAATTGTCAA TCCAGTTTAA ATTTACCACC    2505

ACTCCGTCCT CTGTTGGAGA GGGCTTTGTG TGGGTGAAGT GGCTCCCTGT TGGAGCACCA    2565

ACCAAGACCA CAGATGCTTG GCAGTTAGAA GGAGGTGGAA ATTCAGTTAG AATTCAAAAA    2625

TTGGCCGTTG CAGGGATGTG CCCCACTGTT GTGTTCAAGA TTGCAGGCTC CCGTTCACAA    2685

GCCTGTGCTT CAGCGTTGCC ATATACATCA ATGTGGCGTG TTGTGCCAGT CTTTTACAAT    2745

GGCTGGGGTG CACCTACCAA AGAAAAGGCA ACCTACAATT GGCTTCCTGG TGCACACTTT    2805

GGTTCCATCT TGCTGACTTC TGATGCGCAT GATAAAGGAG GGTGCTACTT GCGGTATGCT    2865

TTCCGCGCGC CAGCGATGTA TTGCCCTCGA CCCATTCCGC CGGCTTTTAC GCGTCCAGCG    2925

GACAAAACCA GACATAAATT TCCCACTAAC ATCAAGAAAC AGTGTACTAA TTACTCTCTC    2985

CTCAAATTGG CTGGAGATGT TGAGAGCAAC CCTGGCCCCA CTATTTTTTC CAAAGCATCA    3045

GCAGACCTGA ATGCCTTGTC AACGTCGCTA GGTGAATTGA CTGGCATGCT AAAAGATCTT    3105

AAAGCCAAGG CAGAAACTTA TTCCCCGTTT TACAAAATGG CCAAAATGCT TTTCAAACTT    3165

GCAACACTAG CTGTGGCAGC TATGAGGACA AAGGACCCAG TAGTGGTGGT TATGTTGATT    3225

GCTGATTTCG GATTGGAGGT CTTTGACACT GGGTTTTTCT TTTCCTACTT TCAAGAGAAG    3285

TTGCAGCCTT ATATGAAAAC TATTCCTGGT AAGATTTCTG ATTTGGTCAC TGATGCGGCT    3345

ACGGCTGCCG CCCAAATTCC AAAGGGAGTG TATTCTTTTG TGTCGTCATT TTTCGAAACG    3405

CCTGAAGGAG TGGTTGAGAA GCAGGTGTCT CTTCGGACAG TGAATGACAT ATTTGCTTTG    3465

CTTAAAAATT CTGATTGGTT CATAAAGACT CTTGTTGCCC TCAAGAAATG GCTGACATCC    3525

TGGTTTGCTC AAGAACAACA GGCAGATGAT GCGCTCTATT CAGAATTGGA AAAATATCCC    3565

TTGTACAAGT TAAAATTGAA GGAACCTGAT ACTCAAGAGG AAGCGCGCCA GTGGTTTAAA    3645

GACATGCAGC AGCGTGCTCT CGCTGTGAAG GACAAAGGTC TCTTTTCCCT CCTGCAAATT    3705

CCATTAGTTA ACTTGCCCCA GAGCCGTCCA GAGCCCGTTG TATGCGTCCT TCGGGGCGCA    3765
```

-continued

```
TCAGGGCAAG GCAAATCTTA TTTGGCAAAT CTGATGGCTC AAGCAATTTC GCTTCTCTTG    3825

GGTGGCAACC AGGACAGTGT GTGGAGTTGT CCTCCTGACC CCACATATTT TGATGGCTAT    3885

AACGGACAGG CTGTGGTGAT TATGGATGCA TTGGGCCAGG ATCCGAATGG TGCTGACTTT    3945

AAATATTTTT GCCAGATGGT CTCTACAACA GCTTTTGTAC CACCTATGGC CCATTTGGAT    4005

GATAAAGGCA TTCCATTTAC TTCTCCTGTT GTTATTTGTA CTACAAATTT GCATTCATCT    4065

TTTACCCCTA TTACTGTTTC TTGTCCTGAA GCTCTTAAGA GGAGGTTTCG GTTTGATGTG    4125

ACGGTGTCCG CTAAACCGGG CTTTGTGCGC ACTGTTGGTT CAAACCAGCT TTTGAATCTC    4185

CCACTTGCTC TTAAGCCAGC TGGTCTTCCC CCACACCCTA TCTTTGAAAA TGACATGCCC    4245

ATTATAAATG GGCAGGCTGT TAAATTGGCT CTTTCTGGTG GAGAAGTGAC AGCTTTTGAG    4305

CTTATTGAGA TGATACTGTC AGAAGTTCAA AACAGACAAG ACACACACAA AATGCCCATT    4365

TTTAAACAAT CATGGTCTGA TTTGTTCAGA AAGTGTACAA CTGATGAGGA ACAGAAAATG    4425

TTGCAGTTTT TAATTGACAA TAAAGATTCA GAAATTCTCA GGGCGTTTGT TTCAGAACGC    4485

TCCATTTTAC TACATGAAGA GTATCTTAAA TGGGAGTCAT ATATGACCAG GAGAGCCAAG    4545

TTTCACCGCC TGGCTGCTGA TTTTGCTATG TTTCTATCCA TTCTTACTTC ACTGATTGTT    4605

ATTTTTTGTT TAGTTTATTC TATGTATCAA CTTTTTAAGA CCCCTGACGA GCAATCAGCT    4665

TATGATCCTT CAACTAAGCC AAAACCAAAG ACCCAGGAAG TGAAAACACT GAAGATTAGG    4725

ACTGAGACTG GTGTACCAGC AACTGACTTG CAACAATCCA TCATGAAAAA TGTTCAGCCA    4785

ATTGAGCTTT ACCTTGACAA TGAATTGGTT ACTGACTGCT CTGCCTTGGG TGTTTATGAC    4845

AATTCATATT TGGTGCCCCT TCATTTGTTT GAATTTGATT TTGATACCAT TGTGCTTGGT    4905

GGACGTCATT ACAAGAAAGC TGAGTGTGAG AAGGTAGAGT TTGAGCTTGA AGTGAATGGA    4965

GACGTGGTGT CATCAGATGC GTGTCTACTT CGAGTGTCAT CGGGGCCTAA AGTTAGAAAT    5035

ATTGTTCATC TTTTTACAAA TGAAATTGAA TTGAAGAAAA TGACCCAAGT GACAGGAATC    5085

ATGAATTCAC CACACCAGGC ACGCACTGTG TTTTTTGGCA GTTTTTTGAC AGTGAGGAAG    5145

TCCATCTTAA CATCGGATGG GACTGTAATG CCCAATGTTT TGTCCTATGC CGCTCAGACC    5205

TCGCGTGGGT ATTGTGGCGC TGCAATTGTT GCTGGCTCAC CTGCCCGCAT AATTGGTATC    5265

CATTCAGCTG GCACTGGATC TGTTGCATTT TGCTCCCTGG TGTCCAGAGA CCAGCTGGAG    5325

CAACTCTGGC CCCAGAAACA GGGCAACGTT AGTCGCCTTG ATGACGATGT GAGGGTGTCT    5385

GTTCCGCGCC GCTCCAAATT GGTGAAATCA TTGGCTTACC CCATTTTCAA ACCTGACTAT    5445

GGCCCAGCGC CACTCTCTCA ATTTGACAAG CGCCTGTCAG ACGGCGTGAA GCTGGATGAA    5505

GTGGTTTTTG CTAAACATAC TGGAGACAAG GAGATTTCCG CACAGGACCA GAAATGGCTC    5565

TTGCGTGCGG CGCATGTATA CGCCCAGAAG GTTTTCTCCC GGATTGGATT TGACAACCAG    5625

GCTTTGACTG AAAAAGAGGC CATTTGTGGC ATTCCTGGCC TTGACAAGAT GGAGCAGGAC    5685

ACCGCTCCGG GGCTGCCCTA TGCTCAGCAA AATAAGAGAA GGAAAGACAT CTGTGATTTT    5745

GAAGAGGGCC GGCTGAAGGG CGCCGAACTC CAAAAGGACA GATTTATGGC TGGTGACTAC    5805

TCTAATTTGG TCTATCAATC ATTTTTGAAA GATGAGATCC GCCCACTTGA GAAAGTTAGG    5865

GCTGGAAAGA CCCGCCTGAT TGACGTGCCG CCGATGCCCC ATGTGGTGGT TGGTAGGCAG    5925

CTCTTGGGCC GGTTTGTGGC AAAATTTCAT GAAGCAAATG GATTTGACAT TGGCTCAGCC    5985

ATTGGATGTG ACCCAGATGT GGACTGGACT CGGTTTGGCC TCGAGTTGGA GCGTTTCAGG    6045

TATGTATATG CCTGTGACTA CTCACGGTTC GATGCCAACC ATGCAGCTGA TGCAATGAGA    6105

GTTGTGCTTA ACTACTTTTT CTCTGAGGAC CACGGTTTCG ACCCTGGTGT GCCTGCTTTT    6165
```

-continued

```
ATTGAGTCAC TGGTTGATTC AGTGCATGCC TATGAAGAGA AAAGGTATAA CATCTACGGT   6225

GGCTTGCCAT CCGGGTGTTC CTGCACATCA ATTTTGAATA CCATCTTGAA CAATGTTTAC   6285

ATTCTTGCAG CTATGATGAA GGCTTATGAG AATTTTGAGC CAGATGACAT TCAGGTCATT   6345

TGCTATGGGG ACGACTGCCT CATTGCTTCT GATTTTGAAA TTGATTTCCA ACAACTGGTG   6405

CCTGTCTTTT CTAGTTTTGG ACAGGTAATA ACTACAGCTG ACAAGACTGA TTTTTTTAAA   6465

CTGACAACCA TTTCGGAGGT GACCTTCCTT AAGCGCGCTT TTGTTCTGAC GGCCTTTTAC   6525

AAGCCAGTGA TGGATGTGAA GACCCTTGAA GCAATCTTAA GCTTTGTTCG CCCAGGCACA   6585

CAGGCTGAAA AGCTCCTGTC CGTGGCGCAG TTGGCAGGCC ACTGCGAACC GGAGCAGTAT   6645

GAGCGCCTGT TTGAGCCCTT TGCTGGGATG TATTTCGTCC CTACTTGGCG ACTTGCGCCT   6705

GCAGTGGTTG ATGAAGCTTG GTAGCTAAAT TCTTTTTGAC TTTGTTTTTC TTTGTTTTCT   6765

TTTAGGCTTT TAAGGTGTTA AGTTTAAAGG TTAAGAGTTT TTAGAAGTTA AGATAGAGTT   6825

TAGTTTTTAG TTTTGAGC-poly(A)
``` as disclosed in FIG. 2 and functional equivalents of said nucleotide sequence including naturally occurring derivatives, variants, degeneracy equivalents and deletion mutants thereof.

In another aspect, the invention provides a substantially pure amino acid sequence being:

a substantially pure amino acid sequence (SEQ ID NO:2) being:

| M | A | A | S | K | V | Y | R | V | C | E | Q | T | L | L | A | G | A | V | R | M | M | D | K | F |
| L | Q | K | R | T | V | F | V | P | H | L | D | K | T | I | R | L | T | G | L | H | N | Y | D | N |
| T | C | W | L | N | A | L | T | Q | L | T | Q | I | L | G | I | R | L | F | D | E | H | F | G | N |
| R | G | L | F | T | R | K | T | I | D | W | V | S | D | Q | T | G | I | K | D | L | K | S | G | A |
| P | P | L | V | V | V | Y | K | L | W | Q | H | G | H | L | D | V | G | T | M | E | K | P | R | S |
| I | T | L | W | S | G | P | K | V | C | L | S | D | F | W | A | C | V | S | A | K | P | G | H | A |
| V | F | Y | L | L | T | S | E | G | W | I | C | V | D | D | K | K | I | Y | P | E | T | P | K | T |
| E | D | V | L | V | F | A | P | Y | D | F | E | S | L | G | K | D | P | P | K | L | H | Q | R | Y |
|   |   |   |   |   | L ↓ VP4 | | | | | | | | | | | | | | | | | | | |
| E | K | A | F | E | L | S | G | G | G | T | S | P | T | T | G | N | Q | N | M | S | G | N | S |   |
| G | S | I | V | Q | N | F | Y | M | Q | Q | Y | Q | N | S | I | D | A | D | L | G | D | N | V | I |
| S | P | E | G | Q | G | S | N | T | S | S | S | T | S | S | S | Q | S | S | G | L | G | G | W | F |
|   |   |   |   |   |   |   |   | VP4 ↓ VP2 | | | | | | | | | | | | | | | | |
| S | S | L | L | N | L | G | T | K | L | L | A | D | K | K | T | E | E | T | T | N | I | E | D | R |
| I | E | T | T | V | V | G | V | T | I | I | N | S | Q | G | S | V | G | T | T | Y | C | Y | S | K |
| P | D | G | R | P | P | S | T | V | S | D | P | V | T | R | L | G | P | T | L | S | R | H | Y | T |
| F | K | V | G | E | W | P | H | S | Q | S | H | G | H | A | W | I | C | P | L | P | G | D | K | L |
| K | K | M | G | S | F | H | E | V | V | K | A | H | M | L | V | K | N | G | W | D | V | V | V | Q |
| V | N | P | S | F | A | H | S | G | P | L | C | V | A | A | V | P | E | Y | E | H | T | H | E | K |
| A | L | K | W | S | E | L | E | E | P | A | Y | T | Y | Q | Q | L | S | V | F | P | H | Q | L | L |
| N | L | R | T | N | S | S | V | H | L | V | M | P | Y | I | G | P | G | Q | P | T | N | L | T | L |
| H | N | P | W | T | I | V | I | L | I | L | S | E | L | T | G | P | G | Q | T | V | P | V | T | M |
|   |   |   |   |   |   |   |   |   |   |   |   |   |   |   |   |   | VP2 ↓ VP3 | | | | | | | |
| S | V | A | P | I | D | A | M | V | N | G | P | L | P | N | P | E | A | P | I | R | V | V | S | V |
| P | E | S | D | S | F | M | S | S | V | P | D | N | S | T | P | L | Y | P | K | V | V | V | P | P |
| R | Q | V | P | G | R | F | T | N | F | I | D | V | A | K | Q | T | Y | S | F | C | S | I | S | G |
| K | P | Y | F | E | V | T | N | T | S | G | D | E | P | L | F | Q | M | D | V | S | L | S | A | A |
| E | L | H | G | T | Y | V | A | S | L | S | S | F | F | A | Q | Y | R | G | S | L | N | F | N | F |
| I | F | T | G | A | A | A | T | K | A | K | F | L | V | A | F | V | P | P | H | S | A | A | P | K |
| T | R | D | E | A | M | A | C | I | H | A | V | N | D | V | G | L | N | S | A | F | S | F | N | V |
| P | Y | P | S | P | A | D | F | M | A | V | Y | S | A | E | R | T | V | N | V | S | G | W | L |   |
| Q | V | Y | A | L | T | A | L | T | S | T | D | I | A | V | N | S | K | G | R | V | L | V | A | V |
|   |   |   |   |   |   |   |   |   |   |   |   |   |   |   |   |   | VP3 ↓ VP2 | | | | | | | |
| S | A | G | P | D | F | S | L | R | H | P | A | D | L | P | D | K | Q | V | T | N | V | G | E | D |
| G | E | P | G | E | T | E | P | R | H | A | L | S | P | V | D | M | H | V | H | T | D | V | S | F |
| L | L | D | R | F | F | D | V | E | T | L | E | L | S | N | L | T | G | S | P | A | T | H | V | L |
| D | P | F | G | S | T | A | Q | L | A | W | A | R | L | L | N | T | C | T | Y | F | F | S | D | L |
| E | L | S | I | Q | F | K | F | T | T | T | P | S | S | V | G | E | G | F | V | W | V | K | W | L |
| P | V | G | A | P | T | K | T | T | D | A | W | Q | L | E | G | G | G | N | S | V | R | I | Q | K |
| L | A | V | A | G | M | C | P | T | V | V | F | K | I | A | G | S | R | S | Q | A | C | A | S | A | a substantially pure amino acid sequence (SEQ ID NO:2) being:

| | | | | | | | | | | | | | | | | | | | | |
|---|---|---|---|---|---|---|---|---|---|---|---|---|---|---|---|---|---|---|---|---|
| L | P | Y | T | S | M | W | R | V | V | P | V | F | Y | N | G | W | G | A | P | T | K | E | K | A |
| T | Y | N | W | L | P | G | A | H | F | G | S | I | L | L | T | S | D | A | H | D | K | G | G | C |
| Y | L | R | Y | A | F | R | A | P | A | M | Y | C | P | R | P | I | P | P | A | F | T | R | P | A |

VP1 ↓ 2A

| D | K | T | R | H | K | F | P | T | N | I | N | K | Q | C | T | N | Y | S | L | L | K | L | A | G |

2A ↓ 2B

| D | V | E | S | N | P | G | P | T | I | F | S | K | A | S | A | D | L | N | A | L | S | T | S | L |
| G | E | L | T | G | M | L | K | D | L | K | A | K | A | E | T | Y | S | P | F | Y | K | M | A | K |
| M | L | F | K | L | A | T | L | A | V | A | A | M | R | T | K | D | P | V | V | V | V | M | L | I |
| A | D | F | G | L | E | V | F | D | T | G | F | F | F | S | Y | F | Q | E | K | L | Q | P | Y | M |
| K | T | I | P | G | K | I | S | D | L | V | T | D | A | A | T | A | A | A | Q | I | P | K | G | V |

2B ↓ 2C

| Y | S | F | V | S | S | F | F | E | T | P | E | G | V | V | E | K | Q | V | S | L | R | T | V | N |
| D | I | F | A | L | L | K | N | S | D | W | F | I | K | T | L | V | A | L | K | K | W | L | T | S |
| W | F | A | Q | E | Q | Q | A | D | D | A | L | Y | S | E | L | E | K | Y | P | L | Y | K | L | K |
| L | K | E | P | D | T | Q | E | E | A | R | Q | W | F | K | D | M | Q | Q | R | A | L | A | V | K |
| D | K | G | L | F | S | L | L | Q | I | P | L | V | N | L | P | Q | S | R | P | E | P | V | V | C |
| V | L | R | G | A | S | G | Q | G | K | S | Y | L | A | N | L | M | A | Q | A | I | S | L | L | L |
| V | G | K | Q | D | S | V | W | S | C | P | P | D | P | T | Y | F | D | G | Y | N | G | Q | A | V |
| V | I | M | D | A | L | G | Q | D | P | N | G | A | D | F | K | Y | F | C | Q | M | V | S | T | T |
| A | F | V | P | P | M | A | H | L | D | D | K | G | I | P | F | T | S | P | V | V | I | C | T | T |
| N | L | H | S | S | F | T | P | I | T | V | S | C | P | E | A | L | K | R | R | F | R | F | D | V |
| T | V | S | A | K | P | G | F | V | R | T | V | G | S | N | Q | L | L | N | L | P | L | A | L | K |
| P | A | G | L | P | P | H | P | I | F | E | N | D | M | P | I | I | N | G | Q | A | V | K | L | A |
| L | S | G | G | E | V | T | A | F | E | L | I | E | M | I | L | S | E | V | Q | N | R | Q | D | T |

2C ↓ 3A

| H | K | M | P | I | F | K | Q | S | W | S | D | L | F | R | K | C | T | T | D | E | E | Q | K | M |
| L | Q | F | L | I | D | N | K | D | S | E | I | L | R | A | F | V | S | E | R | S | I | L | L | H |
| E | E | Y | L | K | W | E | S | Y | M | T | R | R | A | K | F | H | R | L | A | A | D | F | A | M |
| F | L | S | I | L | T | S | L | I | V | I | F | C | L | V | Y | S | M | Y | Q | L | F | K | T | P |

3A ↓ 3B

| D | E | Q | S | A | Y | D | P | S | T | K | P | K | P | K | T | Q | E | V | K | T | L | K | T | R |

3B ↓ 3C

| T | E | T | G | V | P | A | T | D | L | Q | Q | S | I | M | K | N | V | Q | P | I | E | L | Y | L |
| D | N | E | L | V | T | D | C | S | A | L | G | V | Y | D | N | S | Y | L | V | P | L | H | L | F |
| E | F | D | F | D | T | I | V | L | G | G | R | H | Y | K | K | A | E | C | E | K | V | E | F | E |
| L | E | V | N | G | D | V | V | S | S | D | A | C | L | L | R | V | S | S | G | P | K | V | R | N |
| I | V | K | L | F | T | N | E | I | E | L | K | K | M | T | Q | V | T | G | I | M | N | S | P | H |
| Q | A | R | T | V | F | F | G | S | F | L | T | V | R | K | S | I | L | T | S | D | G | T | V | M |
| P | N | V | L | S | Y | A | A | Q | T | S | R | G | Y | C | G | A | A | I | V | A | G | S | P | A |
| R | I | I | G | I | H | S | A | G | T | G | S | V | A | F | C | S | L | V | S | R | D | A | L | S |

3C ↓ 3D

| Q | L | W | P | Q | K | Q | G | N | V | S | R | L | D | D | V | R | V | S | V | P | R | R | S |
| K | L | V | K | S | L | A | Y | P | I | F | K | P | D | Y | G | P | A | P | L | S | Q | F | D | K |
| R | L | S | D | G | V | K | L | D | E | V | V | F | A | K | H | T | G | D | K | E | I | S | A | Q |
| D | Q | K | W | L | L | R | A | A | H | V | Y | A | Q | K | V | F | S | R | I | G | F | D | N | Q |
| A | L | T | E | K | E | A | I | C | G | I | P | G | L | D | K | M | E | Q | D | T | A | P | G | L |
| P | Y | A | Q | Q | N | K | R | R | K | D | I | C | D | F | E | E | G | R | L | K | G | A | E | L |
| Q | K | D | R | F | M | A | G | D | Y | S | N | L | V | Y | Q | S | F | L | K | D | E | I | R | P |
| L | E | K | V | R | A | G | K | T | R | L | I | D | V | P | P | M | P | H | V | V | V | G | R | Q |
| L | L | G | R | F | V | A | K | F | H | E | A | N | G | F | D | I | G | S | A | I | G | C | D | P |
| D | V | D | W | T | R | F | G | L | E | L | E | R | P | R | Y | V | Y | A | C | D | Y | S | R | F |
| D | A | N | H | A | A | D | A | M | R | V | V | L | N | Y | F | F | S | E | D | H | G | F | D | P |
| G | V | P | A | F | I | E | S | L | V | D | S | V | H | A | Y | E | E | K | R | Y | N | I | Y | G |
| G | L | P | S | G | C | S | C | T | S | I | L | N | T | I | L | N | N | V | Y | I | L | A | A | M |
| M | K | A | Y | E | N | F | E | P | D | D | I | Q | V | I | C | Y | G | D | D | C | L | I | A | S |
| D | F | E | I | D | F | Q | Q | L | V | P | V | F | S | S | F | G | Q | V | I | T | T | A | D | K |
| T | D | F | F | K | L | T | T | L | S | E | V | T | F | L | K | R | A | F | V | L | T | A | F | Y |
| K | P | V | M | D | V | K | T | L | E | A | I | L | S | F | V | R | P | G | T | Q | A | E | K | L |
| L | S | V | A | Q | L | A | G | H | C | E | P | E | Q | Y | E | R | L | F | E | P | F | A | G | M |

3D

| Y | F | V | P | T | W | R | L | A | P | A | V | V | D | E | A | W | M | L | N | S | F | as disclosed in FIG. 2.

In another aspect, the invention provides proteins derived from ERhV1 which exhibit virus like particles characteristics incorporating VP1 and having the following amino acid sequence:

a protein or virus like particle incorporating VP1, derived from ERhV1 and
having the following amino acid sequence (SEQ ID NO:3):

| V | T | N | V | G | E | D | G | E | P | G | E | T | E | P | R | H | A | L | S | P | V | D | M | H |
|---|---|---|---|---|---|---|---|---|---|---|---|---|---|---|---|---|---|---|---|---|---|---|---|---|
| V | H | T | D | V | S | F | L | L | D | R | F | F | D | V | E | T | L | E | L | S | N | L | T | G |
| S | P | A | T | H | V | L | D | P | F | G | S | T | A | Q | L | A | W | A | R | L | L | N | T | C |
| T | Y | F | F | S | D | L | E | L | S | I | Q | F | K | F | T | T | T | P | S | S | V | G | E | G |
| F | V | W | V | K | W | L | P | V | G | A | P | T | K | T | T | D | A | W | Q | L | E | G | G | G |
| N | S | V | R | I | Q | K | L | A | V | A | G | M | C | P | T | V | V | F | K | I | A | G | S | R |
| S | Q | A | C | A | S | A | L | P | Y | T | S | M | W | R | V | V | P | V | F | Y | N | G | W | G |
| A | P | T | K | E | K | A | T | Y | N | W | L | P | G | A | H | F | G | S | I | L | L | T | S | D |
| A | K | D | K | G | G | C | Y | L | R | Y | A | F | R | A | P | A | M | Y | C | P | R | P | I | P |
| P | A | F | T | R | P | A | D | K | T | R | H | K | F | P | T | N | I | N | K | Q | C | T |   |   |

15

In another aspect, the invention provides proteins derived from ERhV1 which exhibit virus like particle characteristics incorporating VP2 and having the following amino acid sequence:

a protein or virus like particle incorporating VP2 deived from ERhV1 and
having the following amino acid sequence (SEQ ID NO:4):

| D | K | K | T | E | E | T | T | N | I | E | D | R | I | E | T | T | V | V | G | V | T | I | I | N |
|---|---|---|---|---|---|---|---|---|---|---|---|---|---|---|---|---|---|---|---|---|---|---|---|---|
| S | Q | G | S | V | G | T | T | Y | C | Y | S | K | P | D | G | R | P | P | S | T | V | S | D | P |
| V | T | R | L | G | P | T | L | S | R | H | Y | T | F | K | V | G | E | W | P | H | S | Q | S | H |
| G | H | A | W | I | C | P | L | P | G | D | K | L | K | K | M | G | S | F | H | E | V | V | K | A |
| H | H | L | V | K | N | G | W | D | V | V | V | Q | V | N | P | S | F | A | H | S | G | P | L | C |
| V | A | A | V | P | E | Y | E | H | T | H | E | K | A | L | K | W | S | E | L | E | E | P | A | Y |
| T | Y | Q | Q | L | S | V | F | P | H | Q | L | L | N | L | R | T | N | S | S | V | H | L | V | M |
| P | Y | I | G | P | G | Q | P | T | N | L | T | L | H | N | P | W | T | I | V | I | L | I | L | S |
| E | L | T | G | P | G | Q | T | V | P | V | T | M | S | V | A | P | I | D | A | M | V | N | G | P |
| L | P | N | P | E |   |   |   |   |   |   |   |   |   |   |   |   |   |   |   |   |   |   |   |   |

In another aspect, the invention provides proteins derived from ERhV1 which exhibit virus like particle characteristics incorporating VP3 and having the following amino acid sequence:

a protein or virus like particle incorporating VP3; derived from ERhV1 and
having the following amino acid sequence (SEQ ID NO:5):

| A | P | I | R | V | V | S | V | P | E | S | D | S | F | M | S | S | V | P | D | N | S | T | P | L |
|---|---|---|---|---|---|---|---|---|---|---|---|---|---|---|---|---|---|---|---|---|---|---|---|---|
| Y | P | K | V | V | V | P | P | R | Q | V | P | G | R | F | T | N | F | I | D | V | A | K | Q | T |
| Y | S | F | C | S | I | S | G | K | P | Y | F | E | V | T | N | T | S | G | D | E | P | L | F | Q |
| M | D | V | S | L | S | A | A | E | L | H | G | T | Y | V | A | S | L | S | S | F | F | A | Q | Y |
| R | G | S | L | N | F | N | F | I | F | T | G | A | A | A | T | K | A | K | F | L | V | A | F | V |
| P | P | K | S | A | A | P | K | T | R | D | E | A | M | A | C | I | H | A | V | W | D | V | G | L |
| N | S | A | F | S | F | N | V | P | Y | P | S | P | A | D | F | M | A | V | Y | S | A | E | R | T |
| V | V | N | V | S | G | W | L | Q | V | Y | A | L | T | A | L | T | S | T | D | I | A | V | N | S |
| K | G | R | V | L | V | A | V | S | A | G | P | D | F | S | L | R | H | P | A | D | L | P | D | K |
| O |   |   |   |   |   |   |   |   |   |   |   |   |   |   |   |   |   |   |   |   |   |   |   |   |

In another aspect, the invention provides proteins derived from ERhV1 which exhibit virus like particle characteristics incorporating VP4 and having the following amino acid sequence:

a protein or virus like particle incorporating VP4, derived from ErhV1 and having the following amino acid sequence (SEQ ID NO:6):

```
G G G T S T P T T G N Q N M S G N S G S I V Q N F
Y M Q Q Y Q N S I D A D L G D N V I S P E G Q G S
N T S S S T S S S Q S S G L G G W F S S L L N L G
T K L L A
```

The invention also provides a virus like particle comprising any one or a combination of VP1, VP2, VP3 and VP4.

In another aspect, the invention provides a substantially pure nucleotide sequence for VPI (SEQ ID NO:7) being:

GTTACCAATG TGGGAGAGGA TGGTGAACCC GGTGAGACAG AGCCTCGTCA TGCTTTGTCA

CCCGTGGACA TGCACGTGCA CACAGATGTC AGTTTCTTGC TTGACCGGTT CTTTGATGTT

GAGACACTTG AGCTTTCAAA TTTGACAGGT TCTCCTGCCA CACATGTTCT GGATCCGTTT

GGCTCGACTG CCCAACTGGC TTGGGCACGT CTGCTAAACA CTTGCACCTA CTTCTTTTCT

GATTTGGAAT TGTCAATCCA GTTTAAATTT ACCACCACTC CGTCCTCCGT TGGAGAGGGC

TTTGTGTGGG TGAAGTGGCT CCCTGTTGGA GCACCAACCA AGACCACAGA TGCTTGGCAG

TTAGAAGGAG GTGGAAATTC AGTTAGAATT CAAAAATTGG CCGTTGCAGG GATCTGCCCC

ACTGTTGTGT TCAAGATTGC AGGCTCCCGT TCACAAGCCT GTGCTTCAGC GTTGCCATAT

ACATCAATGT GGCGTGTTGT GCCAGTCTTT TACAATGGCT GGGGTGCACC TACCAAAGAA

AAGGCAACCT ACAATTGGCT TCCTGGTGCA CACTTTGGTT CCATCTTGCT GACTTCTGAT

GCGCATGATA AAGGAGGGTG CTACTTGCGG TATGCTTTCC GCGCGCCAGC GATGTATTGC

CCTCGACCCA TTCCGCCGGC TTTTACGCGT CCAGCGGACA AAACCAGACA TAAATTTCCC

ACTAACATCA ACAAACAGTG TACT and functional equivalents of said nucleotide sequence including naturally occurring derivatives, variants and degeneracy equivalents.

In another aspect, the invention provides a substantially pure nucleotide sequence for VP2 (SEQ ID NO:8) being:

GACAAGAAGA CAGAAGAGAC TACAAACATT GAAGACACAA TTGAAACAAC AGTGGTTGGA

GTCACTATTA TTAATTCACA AGGATCTGTT GGAACAACCT ACTGTTACTC CAAACCGGAT

GGTAGACCAC CATCCACAGT GTCAGACCCA GTTACCAGAC TTGGACCCAC GCTTTCCAGG

CACTACACAT TTAAGGTAGG TGAGTGGCCC CATTCTCAAT CACATGGTCA CGCATGGATC

TGTCCGTTGC CAGGTGACAA ACTCAAGAAG ATGGGCAGTT TCATGAGGT TGTCAAAGCC

CACCACCTGG TCAAGAACGG CTGGGATGTG GTTGTGCAGG TGAATCCCTC ATTTGCTCAC

TCCGGGCCGC TGTGTGTAGC AGCAGTGCCG GAGTACGAAC ACACACATGA GAAAGCACTC

AAGTGGTCTG AGCTTGAGGA ACCAGCTTAC ACATACCAAC AACTTTCAGT TTTTCCCCAC

CAGTTGCTAA ATTTGAGGAC AAATTCATCA GTGCATTTGG TGATGCCCTA CATTGGGCCA

GGCCAACCAA CAAATCTGAC TTTGCACAAC CCGTGGACCA TTGTTATTTT AATTTTGTCT

GAATTGACAG GACCTGGCCA AACTGTGCCT GTGACCATGT CGGTGGCTCC CATCGATGCA

ATGGTTAATG GGCCTCTTCC AAATCCAGAG and functional equivalents of said nucleotide sequence including naturally occurring derivatives, variants and degeneracy equivalents.

```
In another aspect, the invention provides a substantially
pure nucleotide sequence for VP3 (SEQ ID NO:9) being:

GCACCGATTA GAGTGGTGTC TGTGCCTGAA TCAGATTCTT TTATGTCTTC AGTACCTGAT

AATTCGACTC CACTATACCC CAAGGTTGTG GTCCCACCGC GCCAAGTTCC TGGCCGGTTT

ACAAATTTCA TTGATGTGGC AAAACAGACA TATTCATTTT GTTCCATTTC TGGAAAACCT

TATTTTGAGG TTACCAACAC CTCTGGGGAC GAGCCACTGT TTCAGATGGA TGTGTCGCTC

AGTGCGGCAG AGCTACATGG CACTTACGTA GCTAGTTTGT CATCATTTTT TGCACAGTAC

AGAGGCTCAC TTAATTTCAA CTTTATTTTC ACTGGTGCAG CAGCCACTAA GGCAAAGTTT

CTGCTTCCTT TTGTGCCTCC CCACAGTGCA GCGCCCAAAA CGCGCGATGA AGCAATGGCG

TGCATCCATG CCGTGTGGGA TGTTGGCTTG AACTCAGCTT TTTCTTTTAA TGTACCTTAT

CCCTCCCCTG CTGACTTCAT GGCCGTTTAT TCTGCGGAAC GGACGGTTGT GAATGTCTCT

GGATGGCTTC AAGTTTATGC ACTAACAGCT CTAACTTCAA CTGACATTGC CGTGAACAGT

AAAGGCCGTG TGCTGGTTGC TGTTTCCGCC GGCCCAGACT TCTCCCTTCG TCACCCGGCG

GACCTGCCCG ACAACCAG
``` and functional equivalents of said nucleotide sequence including naturally occurring derivatives, variants and degeneracy equivalents.

```
In another aspect, the invention provides a substantially
pure nucleotide sequence for VP4 (SEQ ID NO:10) being:

GGCGGAGGTA CATCCACTCC AACAACTGGC AACCAAAACA TGTCCGGAAA CAGTGGTTCA

ATTGTTCAAA ATTTTTACAT GCAACAGTAC CAGAATTCAA TTGACGCAGA CCTGGGAGAC

AATGTGATTA GCCCTGAAGG CCAGGGCAGC AACACTAGTA GTTCAACCTC ATCAAGCCAA

TCCTCTGGCT TGGGCGGGTG GTTCTCTAGT TTGCTGAACC TTGGAACAAA ACTACTGGCT
``` and functional equivalents of said nucleotide sequence including naturally occurring derivatives, variants and degeneracy equivalents.

In another aspect, the invention provides oligonucleotide primers derived from the nucleotide sequence of FIG. 2 being highly specific for ERhV1 or cross reactive with other ERhV types.

The oligonucleotide primers may have any one of the following nucleotide sequences:

```
VP1F    (SEQ ID NO: 11)5'  GTTGTGTTCAAGATTGCAGGC    3'

VP1R1   (SEQ ID NO: 12)5'  TTGCTCTCAACATCTCCAGC     3'

VP1R2   (SEQ ID NO: 13)5'  TAGCACCCTCCTTTATCATGCG   3'
```

In another aspect, the invention provides an oligonucleotide probe derived from the sequence of FIG. 2.

In another aspect, the invention provides diagnostic reagents, methods and kits characterised by the aforesaid oligonucleotide primers and probes.

In another aspect, the invention provides antigens comprising any one or a combination of the non-capsid proteins, being other than the individual VP1 to VP4 proteins, that are cleaved products of the polypeptide of FIG. 2.

In another aspect, the invention provides vaccines and vectors incorporating any one or a combination of virion proteins VP1 to VP4.

In another aspect, the invention provides diagnostic tests for the detection of antibodies to ERhV1 in blood of horses or other animals characterised by the use of the aforesaid antigens. Such diagnostic tests may be ELISA based.

In a particularly preferred embodiment, the invention provides a test to distinguish horses infected with ERhV1 in which said virus had replicated from horses which have been vaccinated with the vaccine incorporating any one or a combination of virion proteins VP1 to VP4; comprising the steps of applying an antigen being any one of a combination of non-capsid proteins being other than VP1 to VP4, that are cleavage products of the polypeptide of FIG. 2 to a horse and testing for an immunoreaction thereto, wherein a positive immunoreaction would indicate that said horse had been infected with ERhV1 and a negative immunoreaction would indicate that said horse has not been infected with ERhV1.

In another aspect, the invention provides recombinant plasmids incorporating nucleotide sequences and subsequences derived from the nucleotide sequences of FIG. 2. The recombinant plasmid may comprise the P1-2A-3C region of the ERhV1 genome.

In another aspect, the invention provides a host system characterised by incorporating the nucleoside sequence of FIG. 2 or part thereof. The host may be *E.coli,* vaccinia virus, baculovirus or yeast.

In another aspect, the invention provides a process for producing a protein product derived from ERhV1 comprising the shape of selecting out a gene of interest from the ERhV1 nucleotide sequence of FIG. 2 and expressing said protein product in a suitable host system.

SUMMARY OF THE DRAWINGS

The invention will now be described in detail with reference to FIGS. 1 to 6:

FIGS. 2A1–2A7 Nucleotide and predicted amino acid sequence of the ERhV1 polyprotein (SEQ ID NOS 1 & 2). The nucleotide sequences of the 3'-NTR and part of the 5'-NTR are also shown. Numbering is from the first ATG codon that occurs in a context optimal for translational initiation (Kozak, 1989). A polypyrimidine tract upstream of the putative insulating ATG and the two pairs of in-frame ATG codons are underlined. The predicted proteolytic cleavage sites are indicated by arrows.

FIG. 2B Nucleotide sequence of the ERhV1 5'-nontranslated region (SEQ ID NO:22). The polyC tract (dotted underline), polypyrimidine tract (underline) and potential initiation codons (double underline) are indicated. Predicted coding sequence is shown in bold type (SEQ ID NO:23). Numbering is from the ATG considered most likely to be used for translation initiation.

FIGS. 3A–3F Alignment of the predicted amino acid sequences of ERhV1.393/76 (SEQ ID NO:25) and FMDV.O1K (SEQ ID NO:24) polyprotein. Proteolytic cleavage sites, which are predicted in the case of ERhV1, are indicated by the arrows. Identical residues (*), highly conserved residues (:), and less conserved residues (.), are indicated.

Note: The branch lengths represent proportionate change only within each tree; they do not allow direct comparisons to be made between the three trees.

FIGS. 5A and 5B Diagram outlining the strategy for nested, reverse transcription-polymerase chain reaction (RT-PCR) for the detection of ERhV genome. The genome structure of ERhV1 is shown schematically (top), and the first round PCR product (352 bp), corresponding to VP1 and 2A regions, and the second round PCR product (210 bp), corresponding to part of VP1, are represented as black lines.

(B) the sequence of specific oligonucleotide primers used for RT-PCR are shown (SEQ ID NOS 11, 12 & 13). VP1R1 was used for the RT reaction.

Figure 6:
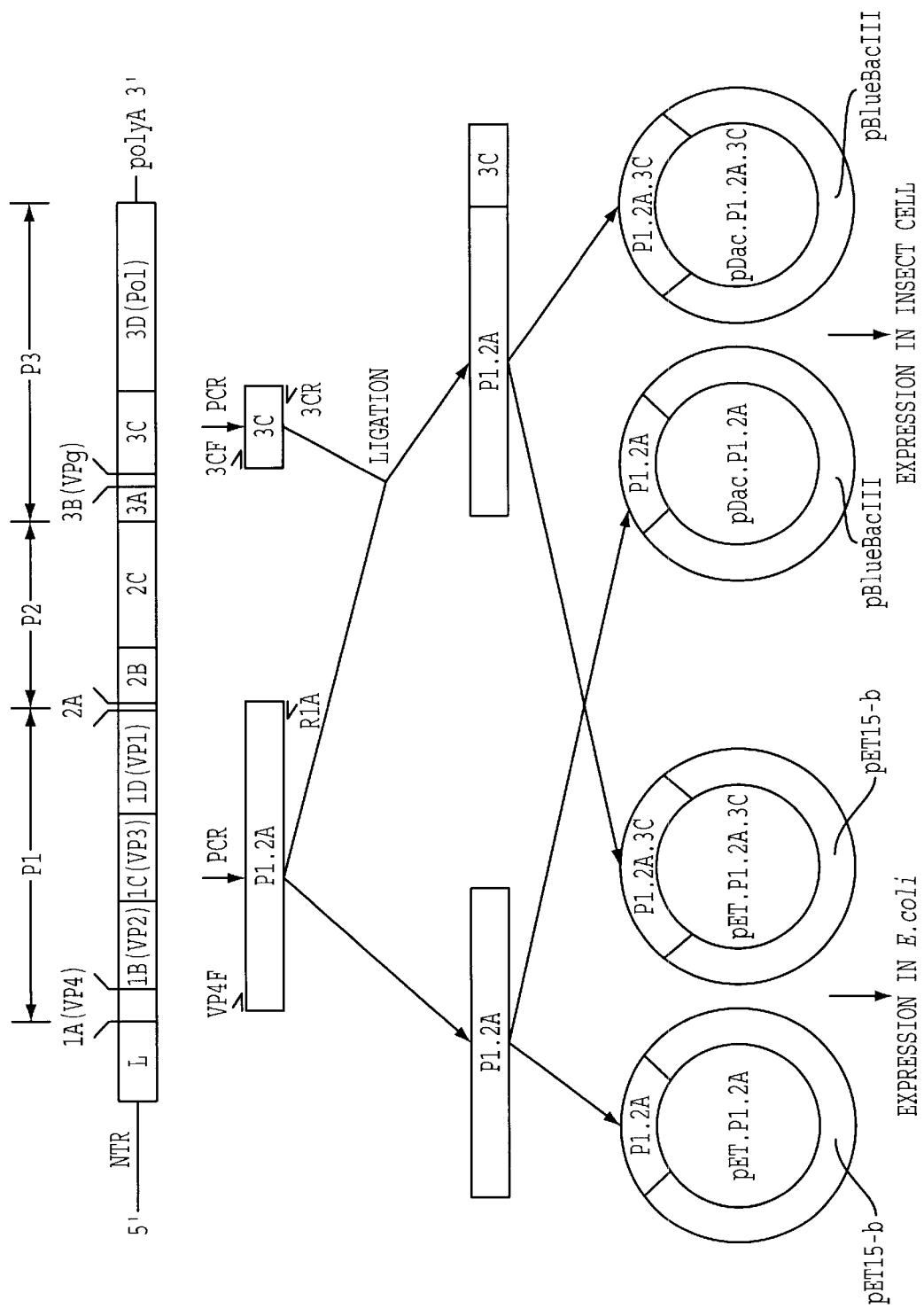

FIG. 6 Construction of ERhV1 expression plasmid for *E. coli* and baculovirus transfer vector for insect cells. The ERhV1 genome is shown (top) and oligonucleotide primers used to amplify P1.2A and 3C regions are depicted as arrows. The P1.2A fragment and subsequently the P1.2A.3C fragment, obtained through the ligation of P1.2A and 3C, were cloned separately into the multiple cloning sites of the pET15b and pBacbluII plasmid vectors to construct pET.P1.2A and pET.P1.2A.3C respectively for expression in *E. coli* an pBac.P1.2A and pBac.P1.2A.3C respectively for expression in insect cells.

DETAILED DESCRIPTION OF INVENTION

The sequence of specific oligonucleotide primers used for the construction of expression plasmids are:

```
VP4F (SEQ ID NO:14)   5' GCTGGATCCATGAGTGGCGGAGGTACATCCACT 3'

R2A  (SEQ ID NO: 15)  5' GCTCTGCAGCAGGTCTGCTGATGCTTTGGA     3'

3CF  (SEQ ID NO: 16)  5' GCTCTGCAGATGATTAGGACTGAGACTGGTGT   3'

3CR  (SEQ ID NO: 17)  5' GCTGGATCCTTAGCCATAGTCAGGTTTGAA     3'
```

Virus growth and purification

ERhV1 strain 393/76 was isolated from a nasal swab taken from a thoroughbred horse in South Australia while it was being held in quarantine following importation from the United Kingdom. The mare had an acute, systemic febrile illness. The virus was passaged 14 times in quine fetal kidney (EFK) monolayer cell cultures and then once in Vero cells. ERhV1 virions were purified by a modification of the procedure described by Abraham and Colonno. Cells were harvested 48 hours after infection. The infected cells and supernatant fluid were frozen and thawed three times and clarified by centrifuging at 2,000× g for 20 min at 4 C. Polyethylene glycol 6000 and NaCl were added to the supernatant to final concentrations of 7% and 380 mM, respectively, and the mixture was stirred overnight at 4 C. The precipitated virions were recovered by centrifuging at 10,000× g for 15 min at 4 C and resuspended in 200–400 µl TNE buffer (10 mM Tris-HCl pH 8.0, 100 mM NaCl, 1 mM EDTA) containing 1% NP40. The suspension was clarified by centrifuging at 12,000× g for 3 min before layering onto 15% to 45% (wt/vol) linear sucrose gradients (35 ml) in TNE buffer and centrifuging at 100,000× g for 4 h at 4 C. Gradients were fractioned and the fractions analyzed by SDS-PAGE. Viral fractions were pooled, centrifuged at 200,000× g for 2 h at 4 C, and the viral pellet was resuspended in a small volume of TNE buffer, cDNA synthesis and cloning. Viral RNA was reverse transcribed using an oligo-dT primer (Amersham) or ERhV1 specific primers P1 (SEQ ID NO:18) (5'-ATCCAGCAAGCCGCTGTCCGGTTAC-3') and P5 (SEQ ID NO:19) (5'-CGAAGAGACACCTGCTTC-3'). Viral RNA was prepared as described in (1987) Anal-Biochem. 162, 156–159.

Viral RNA and 100 pmol of primer were mixed, boiled for 2 min and cooled at room temperature. Fist strand cDNA was synthesized using 200 U of Maloney murine leukemia virus reverse transcriptase (Promega) in the presence of 0.8 mM dNTPs and 30 U of human placental RNAse inhibitor (Pharmacia) in a reaction volume of 25 µl. Second strand cDNA was synthesized using a cDNA synthesis kit (Amersham). The cDNA fragments were ligated into pUC18, either as blunt ended fragments or after ligating BamH I adaptors (Pharmacia), and the lighted products used to transform E. coli strain DH5α (Stratagene). Colonies were selected by hybridization, initially with an [32P]-dCTP-labelled cDNA probe derived from reverse transcribed viral RNA, and subsequently with [32P]-dCTP-labelled cloned viral cDNA (16). The sequence between two cDNA clones was obtained using the oligonucleotide primers P6 (SEQ ID NO: 20) (5'-TTCTGGTGGAGAAGTGACAGC-3') and P7 (SEQ ID NO: 21) (5'-GTGAGCCAGCAACAATTGC-3') in a polymerase chain reaction (PCR; 17) using the polymerase, Vent Exo+ (New England Biolabs).

DNA sequencing and analyses

Double-stranded DNA was prepared using the alkaline lysis method and sequenced by dideoxy chain termination using modified T7 DNA polymerase (Pharmacia) and [35S]-dATP (Amersham). Sequence was read and analyzed using the GeneWorks software package (IntelliGenetics, Mountain View, Calif.). The GenBank database was searched using the FASTA searching and comparison program. The protein alignment shown in FIG. 3 was performed using the Genetics Computer Group, Inc. (Madison, Wis., USA, 1994) GAP program with a gap creation penalty (GCP) of 3.0 and a gap extension penalty (GEP) of 0.1. The multiple alignments of nucleotide sequences were performed using ClustalW. For pairwise alignments the slow method was used with a GCP of 10 and a GEP of 0.1. For multiple alignments a GCP of 10 and a GEP of 0.05 was used with alignment of sequences which were more than 60% divergent delayed and using weighted transitions. Phylogenetic relationships were examined using the maximum likelihood method with the DNAML program of the Phylogeny Inference Package (Phylip) version 3.5c (1993, J. Felsenstein, Department of Genetics, University of Washington, Seattle). The model used allowed for unequal expected frequencies of the four nucleotides, with the frequencies determined empirically from those present in the sequences analysed, and unequal rates of transitions and transversions. A single rate of change was assumed for all sites. The program was allowed to perform global rearrangements to optimize the tree. Initial analyses were performed on polymerase sequences using a range of transition/transversion ratios to determine that which gave the maximal log likelihood. A ratio of 2.0 gave the maximal log likelihood and thus this ratio was used for all subsequent analyses of other sequences.

Cloning and Sequencing of the ERhV1 Genome

Figure 1A:
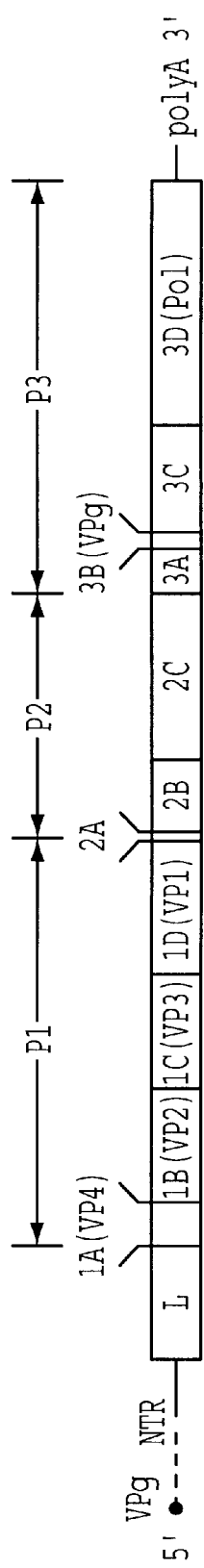
FIGS. 1(A) and (B) (A) Schematic representation of the ERhV1 genome and (B) comparison of the genomic structures of picornaviruses showing the predicted proteolytic cleavage pattern of the polyprotein,. The length of individual regions are drawn approximately to scale. The dashed line represents the unsequenced region of the ERhV1 5'-NTR.
Figure 1B:
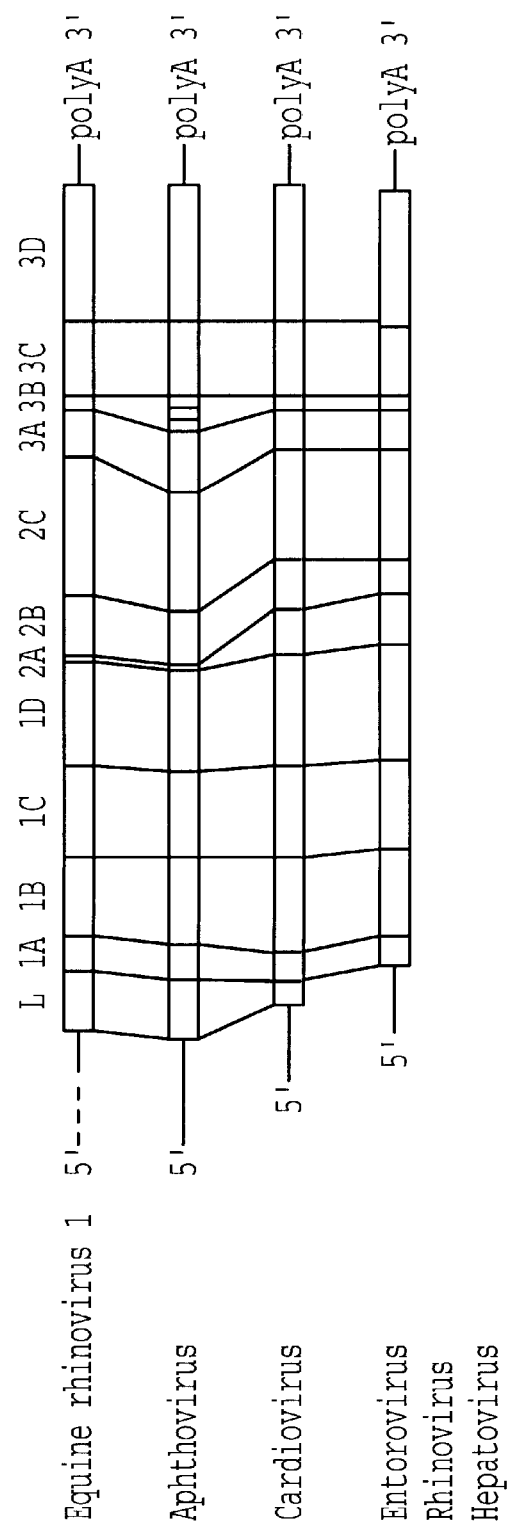

Sixty seven overlapping cDNA clones and one PCR product clone were obtained and sequenced from both ends. The nucleotide in each position was determine at least twice, and 95% of the sequence was obtained by sequencing in both directions. The predicted genomic structure of ERhV1 was characteristic of picornaviruses, possessing one long open reading frame (ORF) flanked by 5'- and 3'-NTR's (FIG. 1).

Figure 2A-3:
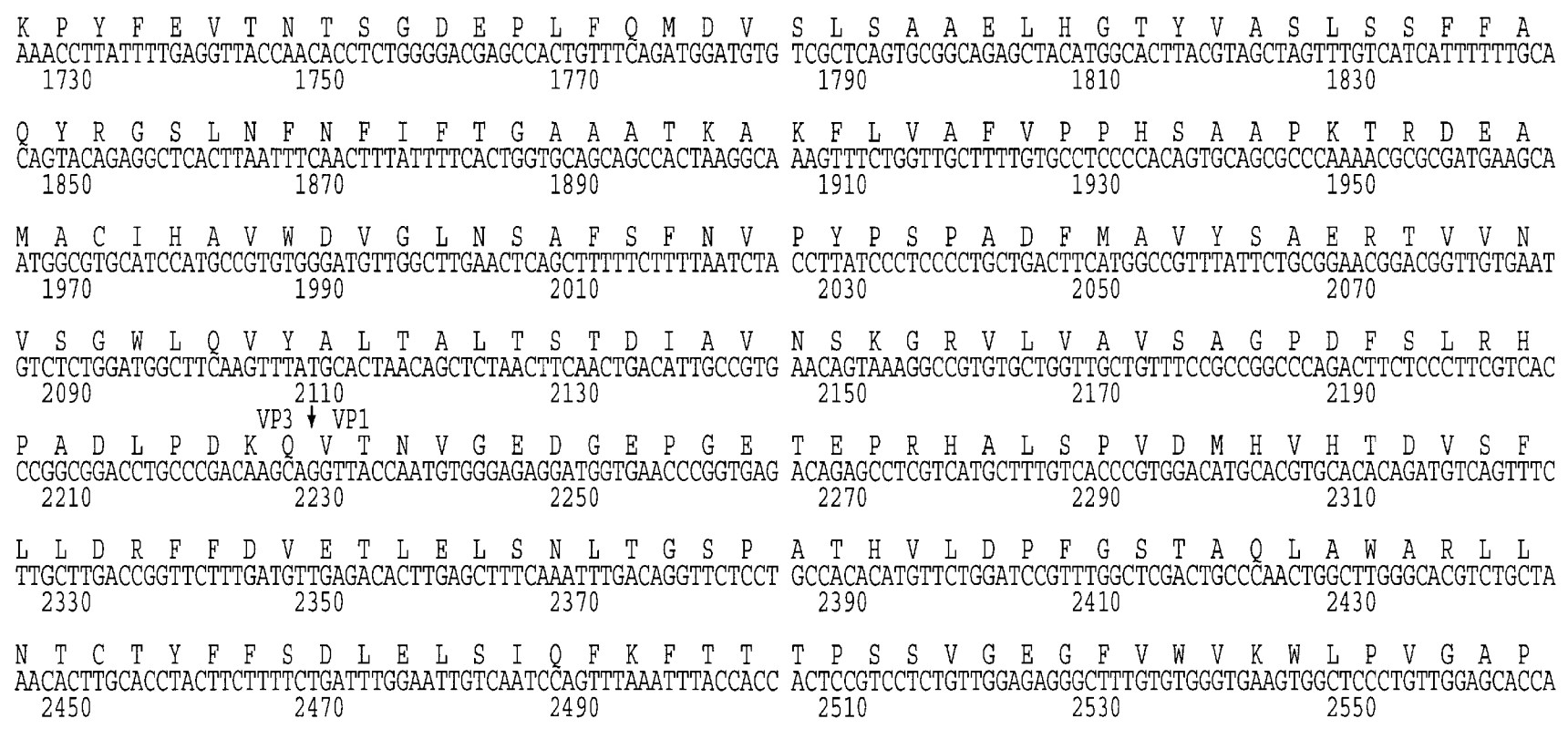
Figure 2A-6:
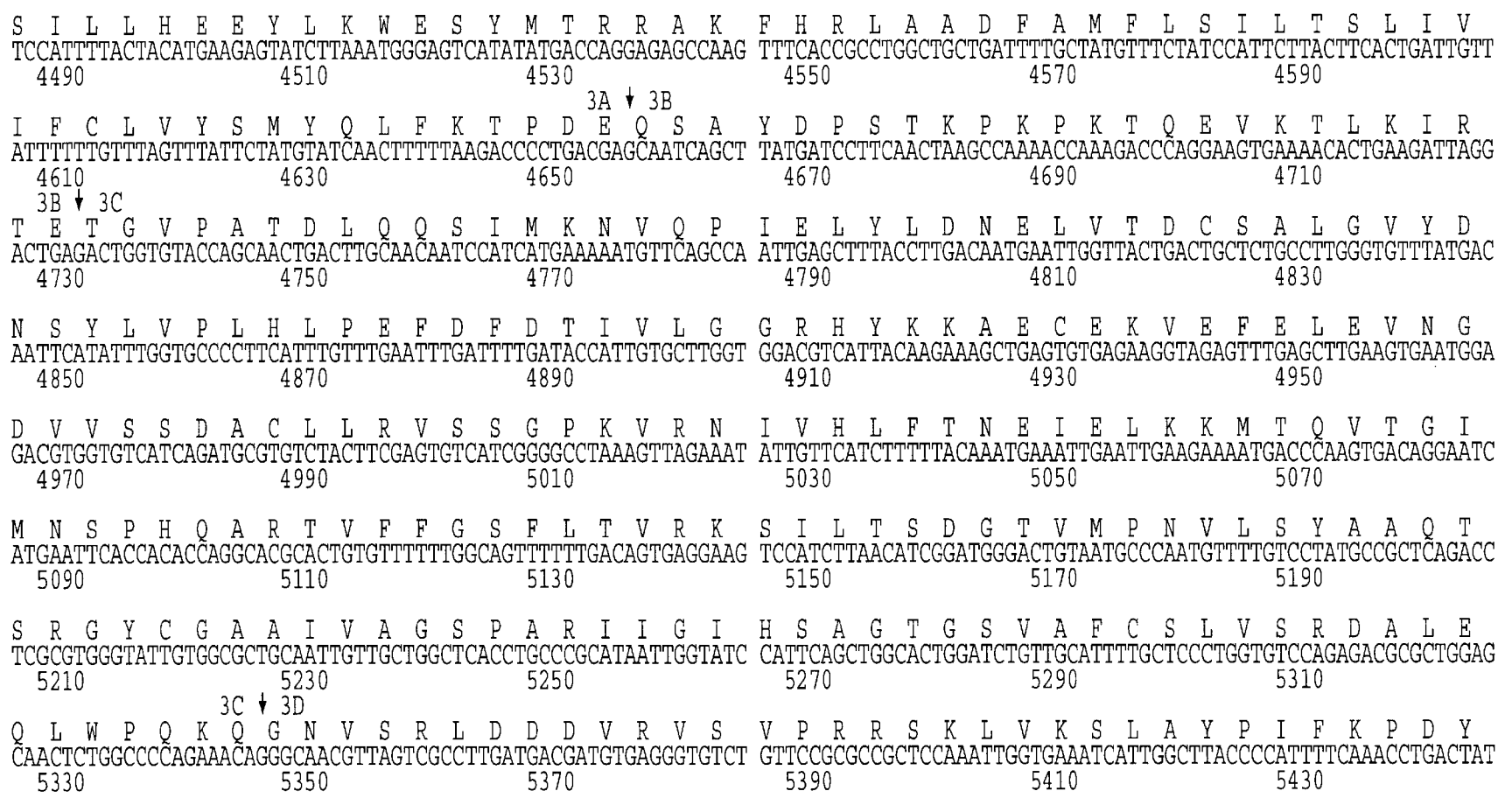
Figure 2A-7:
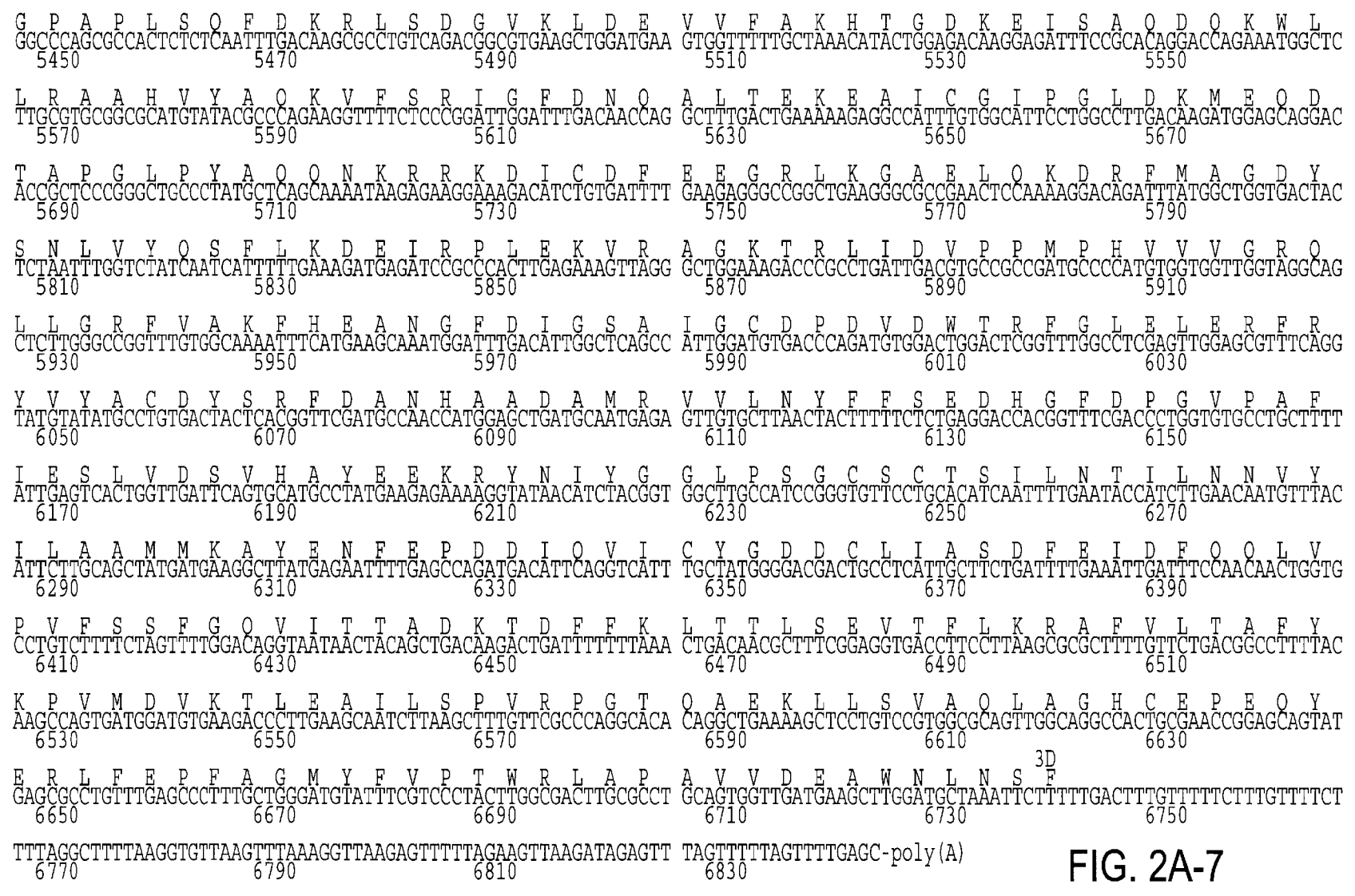

The nucleotide and predicted amino acid sequences of the ERhV1 polyprotein are shown in FIG. 2a. Partial sequence of the 5'-NTR (433 bases) was also obtained FIG. 2b. There was a tract of 9 Cs at position −550 to −542. PolyC tracts of various lengths have been observed in similar locations in FMDV and EMCV. The actual length of the ERhV1 polyC tract is uncertain as these sequences are known to be unstable when propagated in E. coli. A 14 nucleotide polypyrimidine tract, which possessed the TTTC motif common to all picornaviruses, was present near the potential translation initiation codons. A region of 450 nucleotides upstream of the most likely initiation codon is predicted to contain an internal ribosome entry site (IRES). This region showed most sequence identity (48–50%) with corresponding sequences in FMDV and EMCV. The 3'-NTR of ERhV1 was 102 nucleotides excluding the polyA tail (data not shown).

In picornaviruses, there are two factors that influence which ATG codon initiates translation, a requirement for the ATG to be located at the 3'-end of the IRES, and that this ATG occurs in a sequence optimal for initiating translation, that is, a purine at position −3 and a G in position +4. Two pairs of in-frame ATG codons were identified in the ERhV1 genome. The second ATG of the first pair is separated by 25 nucleotides from the beginning of the polypyrimidine tract (FIG. 2b), similar to the distance (25 to 27 nucleotides) found in the corresponding regions in FMDV and EMCV (24). The second ATG of each pair occurs in an optimal context. Therefore, the second ATG of the first pair is most likely to be the translation initiation codon but it is possible that translation is also initiated from the second optimal ATG, by a process of leaky scanning, or even from the other two, non-optimal ATG codons. The predicted ERhV1 coding sequence, beginning at the most likely initiation ATG, extended for 6,741 bases and would encode a polyprotein of 2,247 amino acids.

Alignment of the ERhV1 amino acid sequence with those of other picornaviruses showed that it was most similar to aphthoviruses and, to a lesser extent, to cardioviruses in all regions of the genome (data not shown). FIG. 3 shows a comparison of the predicted amino acid sequence of ERhV1 with that of FMDV.O1K. The two sequences were 40% identical. The more conserved regions include: the 3D/polymerase (50% identity), VP4 (49% identity) and some regions of the 2C protein. ERhV1 encodes a 2A protein of 16 amino acids, 14 of which were identical with those of FMDV 2A. ERhV1 possessed only one copy of the VPg sequence. This is in contrast to FMDV which has 3 tandemly repeated, non-identical VPg sequences (27–29).

Table 1 shows the proteolytic cleavage sites of ERhV1 predicted from the amino acid alignment (FIG. 3), and compares these with those of FMDV, EMCV and Theiler's murine encephalomyelitis virus (TMEV). Most of the ERhV1 cleavage sites could be assigned with reasonable confidence because of significant amino acid similarity with FMDV in the regions flanking the predicted cleavage site; an exception was the 3A/3B cleavage site where there was less sequence similarity. As is the case with FMDV, the predicted ERhV1 3C protease cleavage sites were more variable than those of the cardioviruses. EMCV and TMEV.

TABLE 1

Comparison of the predicted proteolytic cleavage sites of the ERhVI polyprotein with those of FMDV, EMCV and TMEV.

| Proteins | Cleavage sites* | | | |
| --- | --- | --- | --- | --- |
| | ERhV1 | FMDV | EMCV | TMEV |
| Leader/1A(VP4) | S/G | K/G | Q/G | Q/G |
| 1A(VP4)/1B(VP2) | A/D | A/D | A/D | L/D |

TABLE 1-continued

Comparison of the predicted proteolytic cleavage sites of the ERhVI polyprotein with those of FMDV, EMCV and TMEV.

| Proteins | Cleavage sites* | | | |
| --- | --- | --- | --- | --- |
|  | ERhV1 | FMDV | EMCV | TMEV |
| 1B(VP2)/1C(VP3) | E/A | E/G | Q/S | Q/S |
| 1C(VP3)/1D(VP1) | Q/V | E/T | Q/G | Q/G |
| 1D(VP1)/2A | T/N | L/N | E/S | E/N |
| 2A/2B | NPG/P | NPG/P | NPG/P | NPG/P |
| 2B/2C | Q/V | Q/L | Q/S | Q/G |
| 2C/3A | Q/S | Q/I | Q/G | Q/S |
| 3A/3B | Q/S | E/G | Q/G | Q/G |
| 3B/3C | E/T | E/S | Q/G | Q/G |
| 3C/3D | Q/G | E/G | Q/G | Q/G |

*Cleavage data from: FMDV.O1K (Forss et al. 1984), TMEV (Pevear et al. 1987) and EMCV (Palmenberg et al. 1984). The single amino acid code is used.

Phylogenetic analyses

Figure 4A:
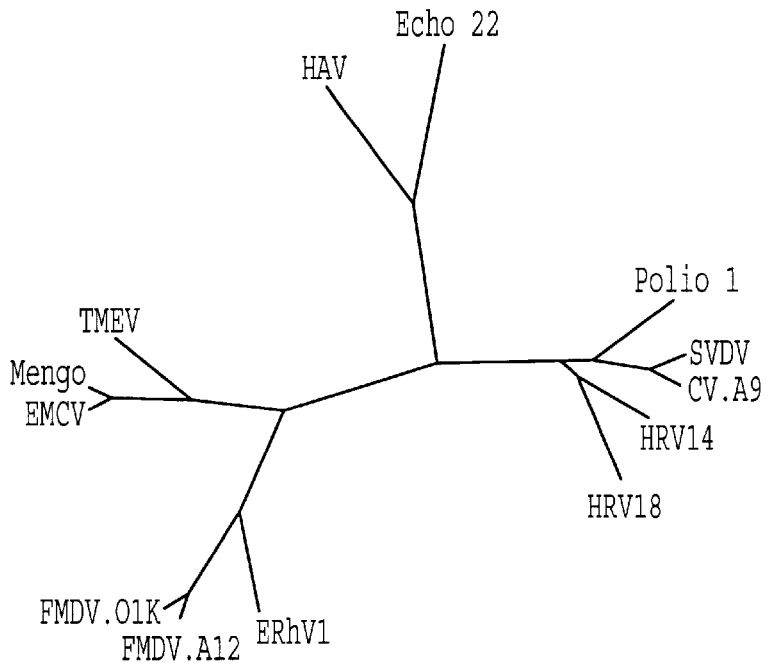
FIGS. 4A–4C Unrooted phylogenic trees inferred using the picornavirus nucleotide sequences of (A) the complete polyprotein gene, (B) the polymerase gene and (C) VP1 gene of viruses representing the five recognised genera of the family Picornaviridae. The viruses used were: FMDV.A10, FMDV.O1K, FMDV.A12, FMDV.C3, FMDV.SAT3, EMCV, TMEV, Mengovirus, poliovirus 1 Mahoney (Polio 1), poliovirus 2.SAbin (Polio 2), poliovirus 3.Leon (Polio 2), coxsackievirus A9 (CV.A9), CV.B3, echovirus 22 (Echo 22), swine vesicular disease virus (SVDV), bovine enterovirus (BEV) heptatitis A virus (HAV) human rhinovirus 1B (HRV1B), HRV89 and HRV14.
Figure 4B:
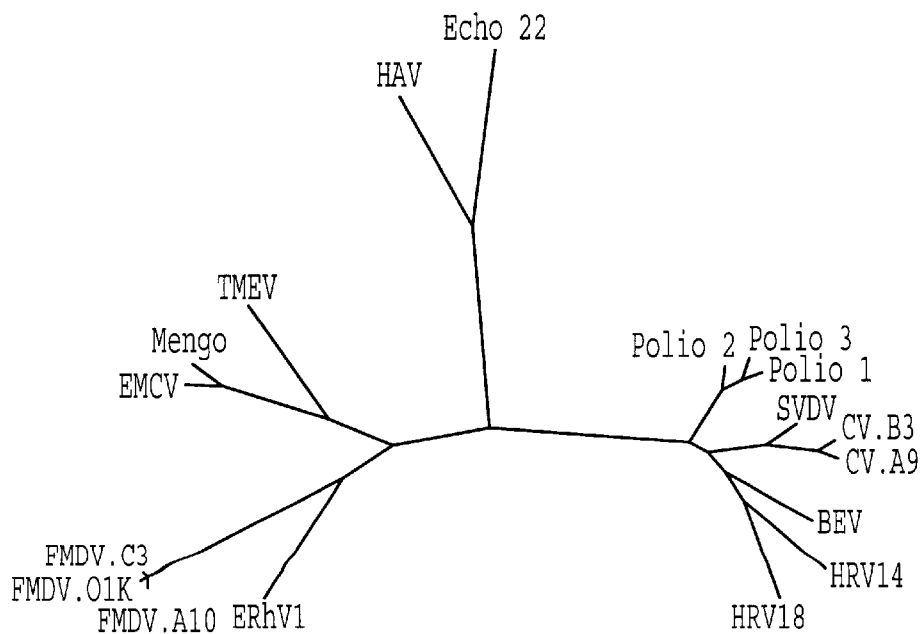
Figure 4C:
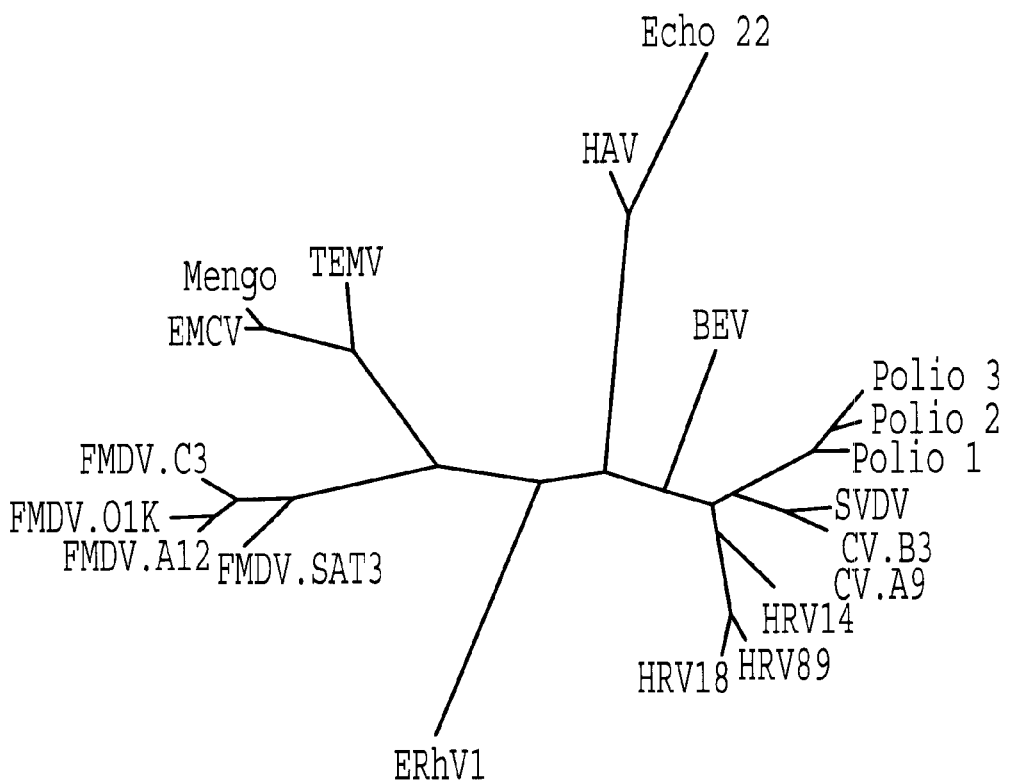

A phylogenetic tree was derived from the nucleotide sequences of complete picornavirus polyproteins (FIG. 4a). Each branch of this tree was statistically, highly significant ($P<0.01$), with the 95% confidence limits ranging from ±7% to ±15% of branch lengths. ERhV1 was found to be most closely related to the aphthoviruses, although it was clear that ERhV1 was considerably more distant from individual members of this genus than the aphthoviruses were from each other. A phylogenetic tree was also derived from the nucleotide sequences of picornavirus polymerase genes (FIG. 4b). Each branch of this tree was statistically, highly significant ($P<0.01$) with 95% confidence limits ranging from ±14% to ±38% of the branch lengths. Again, ERhV1 grouped with the aphthoviruses and the topology of the tree was the same as that obtained using data of the entire polyprotein (FIG. 4a). The VP1 nucleotide sequences were also similarly analyzed (FIG. 4c). Most branches were statistically, highly significant ($P<0.01$), although, that between the ERhV1 branch point and the branch point for the echovirus 22-hepatovirus cluster was less so ($P<0.05$). The 95% confidence limits of the branch lengths of this tree were considerable greater than for the other two trees, ranging from ±18% to ±69%. This tree did not group ERhV1 with the aphthoviruses. With the exception of bovine enterovirus (BEV), the tree had the same topology as those derived from the complete polyprotein and the polymerase sequences. It was also apparent that picornaviruses formed three clusters: enteroviruses-rhinoviruses, echovirus 22-hepatovirus and cardioviruses-aphthoviruses-ERhV1.

(1) Diagnostic Reagents

Oligonucleotide primers: We have designed short oligonucleotide primers and used them in polymerase chain reactions (PCR) for the diagnosis of ERhV infected horses. Any of the ERhV nucleotide sequences may be used for the design primer sets for use as diagnostic reagents. They may be highly specific for ERhV1 or they may be designed to be more cross reactive so as to amplify single strand RNA template from other ERhV types e.g., ERhV 2, 3 and 4. As a specific example we have used the primer set shown in FIG. 5 to diagnose ERhV disease in several groups of seriously ill horses in circumstances in which, despite exhaustive efforts, we could not isolate the virus using conventional cell culture procedures. We no consider ERhV a very under reported disease simply because, most of the time, nasal samples collected from horses experiencing severe, systemic clinical disease because of ERhV infection do not yield the virus in cell culture. In one particular group of horses, we detected the presence of ERhV by PCR and confirmed that the horses were both actively infected and seriously ill with ERhV by use of paired serum samples which showed that there was a concomitant rise in ERhV1 serum neutralising antibody. Vigorous attempts to isolate the virus in cell cultures yielded negative results.

Oligonucleotide probes: Virus specific oligonucleotides are used as probes to detect the presence of the virus in infected samples from diseased horses and other animals. This may be especially important given the systemic nature of the illness, i.e., it is a foot-and-mouth-like, generalized disease with virus distributed throughout the body in many organs and tissues; it is not just a simple "common cold-like" illness as the name rhinovirus implies. The significance of the sequence in moving the virus out of the Rhinovirus genus and into a new genus proposed to be called "Equirhinovirus" in the Picornaviridae family does not represent merely a taxonomic change but represents a paradigm shift in how ERhV1 and related viruses must now be regarded as pathogens for the horse and other animal species.

Diagnostic antigens: Individual virion proteins, in particular VP1, VP2 and VP3, can be expressed in any one of a number of heterologous expression systems to provide antigens to detect specific antibody to ERhV1 present in blood. Such expression systems, which are well established for E. coli, yeast, vaccinia virus and baculovirus, allow for the production of large quantities of protein to a high degree of purity. The expressed virion proteins may be used in simple immunoassays, such as ELISA, to detect ERhV1 specific antibody. Virion proteins expressed in this way also serve as effective vaccines against ERhV1 disease.

(2) Vaccines

Production of virus like particles (VLPs): We have used the sequence information to construct recombinant plasmids containing the P1-2A-3C region of the genome (see FIG. 1a and FIG. 6). These plasmid constructions are of course critically dependent on the ERhV1 sequence that has been determined although the strategy that we are adopting, in general, is similar to that described in J. Virol 66, 4557–4564. Some early plasmid constructions have been inserted into E. coli and baculovirus expression systems based on prior art with similar viruses such as poliomyelitis of humans and foot-and-mouth disease virus of cattle and other cloven hoofed animals. The RT PCR double stranded DNA of the P1-2A-3C region of the ERhV1 genome is transcribed, within the transformed E. coli or insect cell for baculovirus, into messenger RNA as a single transcript which is then translated into a mini polyprotein. The 3C protease activity results in the cleavage of the mini polyprotein into its constituent parts namely 1A (VP4), 1B (VP2), 1C (VP3) and 1D(VP1), 2A and 3C (see FIG. 1a and FIG. 6) and that the VP component parts then self assemble into VLPs i.e., virus particles that lack nucleic acid and are therefore non infectious i.e., are unstable to cause disease. Two important applications of ERhV VLPs are as follows:

(a) The VLPs are very useful as highly effective, safe, high antigen-mass vaccines for the control ERhV1 disease. If ERhV1 disease is confirmed, as we believe to be the case, as significant and responsible for much hither to undiagnosed illness that results in many lost training days, many expensive treatments, much serious illness because of secondary infections following on the primary ERhV1 infection, and much poor performance, then the utility of the vaccine based on the VLPs that are the subject of this invention will be very great and likely to have world-wide application.

With improved methods for the diagnosis of ERhV1 infection such as by PCR and ELISA as described herein, it is likely that other members of the proposed new Equirhinovirus genus within the family Picornaviridae including for example ERhV2, ERhV3, may be similarly diagnosed. Indeed suitably selected PCR primer sets based on the ERhV1 sequence could be used to detect these other equine rhinoviruses. The sequencing of these genomes could provide a basis for their specific diagnosis. It is also evident that the construction of VLP's based on expression plasmids similar to those described herein for ERhV1, could be readily adapted to these other equine rhinoviruses leading for example to production of combined ERhV vaccines to cover all antigenic types as may be extant or as may emerge by antigenic variation, as is very much a part of the biology of FMDV, in the future. Polyvalent VLP vaccines incorporating a range of ERhV antigenic types are obvious extensions based on the work described herein.

(b) ERhV VLPs can be used as a delivery vector that will provide not only protection against ERhV disease but will be used to deliver other therapeutic and useful substances to the horses following administration by parenteral or other routes. Such delivery vectors can be produced by inserting into, for example the P1 region at some appropriate site, double stranded DNA coding for antigenic epitopes of other virus and infections agents of horse as well as epitopes derived from other non infectious sources for example reproductive hormones.

ERhV1 Diagnostic Tests

For the detection of ERhV1 antibodies in infected or vaccinated horses various stranded tests can be used. VLP's may be used in such test for example in an ELISA test for antibody.

Other diagnostic tests based on recombinant antigens derived from the ERhV1 sequence can be devised along similar lines to those reported for FMDV in which the absence of protein 2C from clarified inactivated whole virus FMD, FMDV or FMDV VLP vaccines may be used as the basis for distinguishing infected from vaccinated animals where the vaccine is a non-replicating form of ERhV1 or a deletion mutant of ERhV1 in which a particular non-structural protein gene has been deleted. Precedent for this comes from studies of FMDV as reported in for example Lubroth, Grubman, Burrage, Newman & Brown, 1996, Absence of protein 2C from clarified foot-and-mouth disease virus vaccines provides the basis for distinguishing convalescent from vaccinated animals, Vaccine 14(5), 419–427.

Preparation and Use of Virus-Like Particles and Other Proteins Based on ERhV1 Sequence From the sequence of ERhV1 it is possible to clone certain segments of the viral genome into a variety of vectors for expression in a variety of different expression systems. There is a straight forward and storing literature for FMDV that provides a very clear precedent for what can be done for ERhV1. Examples include the expression of FMDV P1-2A in a baculovirus (Abrams C C & Belsham G J, 1994, The antigenicity of foot-and-mouth disease virus P1-2A polyprotein and empty capsids produced in vaccinia virus and baculovirus expression systems. In VIIth Meeting of the European Study Group on the Molecular Biology of Picornaviruses, Aug. 6–11, 1994, Korpilampi, Finland) or vaccina virus systems (Abrams C C, King A M Q & Belsham G J, 1995, Assembly of foot-and-mouth disease virus empty capsids synthesized by a vaccinia virus expression system. Journal of General Virology 76:3089–3098) to obtain VLPs or viral proteins. We have prepared similar plasmids in which P1-2A, P1-2A-3C and these two sequences in a myristolated form have been inserted into p fastbac 1 baculovirus vector (Gibco/BRL) and into a PET vector (Novogene) for expression in insect cells and *E. coli* respectively.

These expressed products either as protein antigens or as VLPs, have utility as the basis for diagnostic tests or vaccines.

Accordingly, such references are herein incorporated in support of the full description and enablement of the invention where the disclosed methods of preparing diagnostics, vaccines, vectors, host systems and kits are fully described and applicable to the like aspects of the current invention.

(3) Applications in human medicine:

ERhV is also a human pathogen. We have unpublished data to confirm that humans have serum neutralising antibody to ERhV1 that is indicative of infection. One of the laboratory workers connected with the conduct of the sequencing and who handled infections virus has specific antibody in high amounts (serum neutralising antibody titre 1:640 to ERhV1). We are currently extending these studies and anticipate finding a significant incidence of infection in humans world wide particularly among those humans who work with horses. The improved diagnostic methods outlined above, perhaps also the vaccine, are expected to have application in human medicine.

What is claimed is:

1. An isolated polynucleotide comprising the nucleotide sequence of SEQ ID NO: 1.

2. A recombinant plasmid comprising the polynucleotide of claim 1.

3. A recombinant plasmid according to claim 2 comprising the P1-2A-3C region of the ERhV1 genome.

4. A host system comprising the polynucleotide of claim 1.

5. A process for producing a polypeptide, comprising expressing a polypeptide from the polynucleotide of claim 1 in a host system.

* * * * *

SEQUENCE LISTING

<160> NUMBER OF SEQ ID NOS: 25

<210> SEQ ID NO 1
<211> LENGTH: 7278
<212> TYPE: DNA
<213> ORGANISM: equine rhinovirus 1
<220> FEATURE:
<221> NAME/KEY: CDS
<222> LOCATION: (436)..(7176)

<400> SEQUENCE: 1

```
ccgtcaagcc cgttgcctgt atagccaggt aaccggacag cggcttgctg gattttcccg      60
gtgccattgc tctggatggt gtcaccaagc tgacaaatgc ggagtgaacc tcacaaagcg     120
acacgcctgt ggtagcgctg cccaaaaggg agcggaactc cccgccgagg cggtcctctc     180
```

```
tggccaaaag cccagcgttg atagcgcctt tgggatgca ggaacccac  ctgccaggtg    240 tgaagtggag tgagcggatc tccaatttgg tctgttctga actacaccat ttactgctgt    300
gaagaatgcc ctggaggcaa gctggttaca gccctgacca ggccctgccc gtgactctcg    360
accggcgcag gtcaaaaat tgtctaagca gcagcaggaa cgcgggagcg tttcttttcc    420
ttttgtactg acatg atg gcg gcg tct aag gtg tat aga gtt tgc gag cag      471
             Met Ala Ala Ser Lys Val Tyr Arg Val Cys Glu Gln
              1               5                  10
```

```
act ctg ctg gca ggt gcc gtt cgc atg atg gac aaa ttc ttg caa aag      519
Thr Leu Leu Ala Gly Ala Val Arg Met Met Asp Lys Phe Leu Gln Lys
         15                  20                  25
```

```
aga act gtt ttt gtc ccc cat ctt gac aaa aca att cgt ttg act gga      567
Arg Thr Val Phe Val Pro His Leu Asp Lys Thr Ile Arg Leu Thr Gly
    30                  35                  40
```

```
ctc cac aat tat gac aat act tgc tgg ttg aat gcc ttg aca caa ctg      615
Leu His Asn Tyr Asp Asn Thr Cys Trp Leu Asn Ala Leu Thr Gln Leu
45                  50                  55                  60
```

```
aca cag att ctt gga att cgg ctt ttt gat gaa cac ttc ggc aat aga      663
Thr Gln Ile Leu Gly Ile Arg Leu Phe Asp Glu His Phe Gly Asn Arg
                65                  70                  75
```

```
ggt ctg ttc act cgg aaa aca att gat tgg gtg agt gac cag act ggt      711
Gly Leu Phe Thr Arg Lys Thr Ile Asp Trp Val Ser Asp Gln Thr Gly
            80                  85                  90
```

```
ata aaa gat cta aaa tca gga gca ccg cca ctc gtg gtg gtg tac aaa      759
Ile Lys Asp Leu Lys Ser Gly Ala Pro Pro Leu Val Val Val Tyr Lys
                95                  100                 105
```

```
ctg tgg caa cat gga cac ttg gat gtc ggt acg atg gag aaa ccc cgg      807
Leu Trp Gln His Gly His Leu Asp Val Gly Thr Met Glu Lys Pro Arg
110                 115                 120
```

```
tcg att act cta tgg tct ggc ccc aaa gtg tgt ctt tct gat ttc tgg      855
Ser Ile Thr Leu Trp Ser Gly Pro Lys Val Cys Leu Ser Asp Phe Trp
125                 130                 135                 140
```

```
gcc tgt gtt tcg gca aaa ccg gga cat gca gta ttc tac ctt ctc aca      903
Ala Cys Val Ser Ala Lys Pro Gly His Ala Val Phe Tyr Leu Leu Thr
                145                 150                 155
```

```
agc gag ggt tgg atc tgt gtt gat gac aag aaa ata tac cca gaa aca      951
Ser Glu Gly Trp Ile Cys Val Asp Asp Lys Lys Ile Tyr Pro Glu Thr
            160                 165                 170
```

```
ccc aaa aca gag gat gta ctt gtt ttt gcg ccc tat gac ttt gag tca      999
Pro Lys Thr Glu Asp Val Leu Val Phe Ala Pro Tyr Asp Phe Glu Ser
175                 180                 185
```

```
ctg ggc aag gac cca cca aag cta cac cag aga tat gaa aaa gca ttt     1047
Leu Gly Lys Asp Pro Pro Lys Leu His Gln Arg Tyr Glu Lys Ala Phe
    190                 195                 200
```

```
gag ctc agt ggc gga ggt aca tcc act cca aca act ggc aac caa aac     1095
Glu Leu Ser Gly Gly Gly Thr Ser Thr Pro Thr Thr Gly Asn Gln Asn
205                 210                 215                 220
```

```
atg tcc gga aac agt ggt tca att gtt caa aat ttt tac atg caa cag     1143
Met Ser Gly Asn Ser Gly Ser Ile Val Gln Asn Phe Tyr Met Gln Gln
                225                 230                 235
```

```
tac cag aat tca att gac gca gac ctg gga gac aat gtg att agc cct     1191
Tyr Gln Asn Ser Ile Asp Ala Asp Leu Gly Asp Asn Val Ile Ser Pro
            240                 245                 250
```

```
gaa ggc cag ggc agc aac act agt agt tca acc tca tca agc caa tcc     1239
Glu Gly Gln Gly Ser Asn Thr Ser Ser Ser Thr Ser Ser Ser Gln Ser
255                 260                 265
```

```
tct ggc ttg ggc ggg tgg ttc tct agt ttg ctg aac ctt gga aca aaa     1287
Ser Gly Leu Gly Gly Trp Phe Ser Ser Leu Leu Asn Leu Gly Thr Lys
```

```
                     270                 275                 280
cta ctg gct gac aag aag aca gaa gag act aca aac att gaa gac aga    1335
Leu Leu Ala Asp Lys Lys Thr Glu Glu Thr Thr Asn Ile Glu Asp Arg
285                 290                 295                 300 att gaa aca aca gtg gtt gga gtc act att att aat tca caa gga tct    1383
Ile Glu Thr Thr Val Val Gly Val Thr Ile Ile Asn Ser Gln Gly Ser
                305                 310                 315 gtt gga aca acc tac tgt tac tcc aaa ccg gat ggt aga cca cca tcc    1431
Val Gly Thr Thr Tyr Cys Tyr Ser Lys Pro Asp Gly Arg Pro Pro Ser
        320                 325                 330 aca gtg tca gac cca gtt acc aga ctt gga ccc acg ctt tcc agg cac    1479
Thr Val Ser Asp Pro Val Thr Arg Leu Gly Pro Thr Leu Ser Arg His
            335                 340                 345 tac aca ttt aag gta ggt gag tgg ccc cat tct caa tca cat ggt cac    1527
Tyr Thr Phe Lys Val Gly Glu Trp Pro His Ser Gln Ser His Gly His
        350                 355                 360 gca tgg atc tgt ccg ttg cca ggt gac aaa ctc aag aag atg ggc agt    1575
Ala Trp Ile Cys Pro Leu Pro Gly Asp Lys Leu Lys Lys Met Gly Ser
365                 370                 375                 380 ttt cat gag gtt gtc aaa gcc cac cac ctg gtc aag aac ggc tgg gat    1623
Phe His Glu Val Val Lys Ala His His Leu Val Lys Asn Gly Trp Asp
                385                 390                 395 gtg gtt gtg cag gtg aat ccc tca ttt gct cac tcc ggg ccg ctg tgt    1671
Val Val Val Gln Val Asn Pro Ser Phe Ala His Ser Gly Pro Leu Cys
        400                 405                 410 gta gca gca gtg ccg gag tac gaa cac aca cat gag aaa gca ctc aag    1719
Val Ala Ala Val Pro Glu Tyr Glu His Thr His Glu Lys Ala Leu Lys
            415                 420                 425 tgg tct gag ctt gag gaa cca gct tac aca tac caa caa ctt tca gtt    1767
Trp Ser Glu Leu Glu Glu Pro Ala Tyr Thr Tyr Gln Gln Leu Ser Val
        430                 435                 440 ttt ccc cac cag ttg cta aat ttg agg aca aat tca tca gtg cat ttg    1815
Phe Pro His Gln Leu Leu Asn Leu Arg Thr Asn Ser Ser Val His Leu
445                 450                 455                 460 gtg atg ccc tac att ggg cca ggc caa cca aca aat ctg act ttg cac    1863
Val Met Pro Tyr Ile Gly Pro Gly Gln Pro Thr Asn Leu Thr Leu His
                465                 470                 475 aac ccg tgg acc att gtt att tta att ttg tct gaa ttg aca gga cct    1911
Asn Pro Trp Thr Ile Val Ile Leu Ile Leu Ser Glu Leu Thr Gly Pro
        480                 485                 490 ggc caa act gtg cct gtg acc atg tcg gtg gct ccc atc gat gca atg    1959
Gly Gln Thr Val Pro Val Thr Met Ser Val Ala Pro Ile Asp Ala Met
            495                 500                 505 gtt aat ggg cct ctt cca aat cca gag gca ccg att aga gtg gtg tct    2007
Val Asn Gly Pro Leu Pro Asn Pro Glu Ala Pro Ile Arg Val Val Ser
        510                 515                 520 gtg cct gaa tca gat tct ttt atg tct tca gta cct gat aat tcg act    2055
Val Pro Glu Ser Asp Ser Phe Met Ser Ser Val Pro Asp Asn Ser Thr
525                 530                 535                 540 cca cta tac ccc aag gtt gtg gtc cca ccg cgc caa gtt cct ggc cgg    2103
Pro Leu Tyr Pro Lys Val Val Val Pro Pro Arg Gln Val Pro Gly Arg
                545                 550                 555 ttt aca aat ttc att gat gtg gca aaa cag aca tat tca ttt tgt tcc    2151
Phe Thr Asn Phe Ile Asp Val Ala Lys Gln Thr Tyr Ser Phe Cys Ser
        560                 565                 570 att tct gga aaa cct tat ttt gag gtt acc aac acc tct ggg gac gag    2199
Ile Ser Gly Lys Pro Tyr Phe Glu Val Thr Asn Thr Ser Gly Asp Glu
            575                 580                 585 cca ctg ttt cag atg gat gtg tcg ctc agt gcg gca gag cta cat ggc    2247
```

```
                        -continued

Pro Leu Phe Gln Met Asp Val Ser Leu Ser Ala Ala Glu Leu His Gly
    590                 595                 600 act tac gta gct agt ttg tca tca ttt ttt gca cag tac aga ggc tca    2295
Thr Tyr Val Ala Ser Leu Ser Ser Phe Phe Ala Gln Tyr Arg Gly Ser
605                 610                 615                 620 ctt aat ttc aac ttt att ttc act ggt gca gca gcc act aag gca aag    2343
Leu Asn Phe Asn Phe Ile Phe Thr Gly Ala Ala Ala Thr Lys Ala Lys
                625                 630                 635 ttt ctg gtt gct ttt gtg cct ccc cac agt gca gcg ccc aaa acg cgc    2391
Phe Leu Val Ala Phe Val Pro Pro His Ser Ala Ala Pro Lys Thr Arg
            640                 645                 650 gat gaa gca atg gcg tgc atc cat gcc gtg tgg gat gtt ggc ttg aac    2439
Asp Glu Ala Met Ala Cys Ile His Ala Val Trp Asp Val Gly Leu Asn
        655                 660                 665 tca gct ttt tct ttt aat gta cct tat ccc tcc cct gct gac ttc atg    2487
Ser Ala Phe Ser Phe Asn Val Pro Tyr Pro Ser Pro Ala Asp Phe Met
670                 675                 680 gcc gtt tat tct gcg gaa cgg acg gtt gtg aat gtc tct gga tgg ctt    2535
Ala Val Tyr Ser Ala Glu Arg Thr Val Val Asn Val Ser Gly Trp Leu
685                 690                 695                 700 caa gtt tat gca cta aca gct cta act tca act gac att gcc gtg aac    2583
Gln Val Tyr Ala Leu Thr Ala Leu Thr Ser Thr Asp Ile Ala Val Asn
                705                 710                 715 agt aaa ggc cgt gtg ctg gtt gct gtt tcc gcc ggc cca gac ttc tcc    2631
Ser Lys Gly Arg Val Leu Val Ala Val Ser Ala Gly Pro Asp Phe Ser
            720                 725                 730 ctt cgt cac ccg gcg gac ctg ccc gac aag cag gtt acc aat gtg gga    2679
Leu Arg His Pro Ala Asp Leu Pro Asp Lys Gln Val Thr Asn Val Gly
        735                 740                 745 gag gat ggt gaa ccc ggt gag aca gag cct cgt cat gct ttg tca ccc    2727
Glu Asp Gly Glu Pro Gly Glu Thr Glu Pro Arg His Ala Leu Ser Pro
750                 755                 760 gtg gac atg cac gtg cac aca gat gtc agt ttc ttg ctt gac cgg ttc    2775
Val Asp Met His Val His Thr Asp Val Ser Phe Leu Leu Asp Arg Phe
765                 770                 775                 780 ttt gat gtt gag aca ctt gag ctt tca aat ttg aca ggt tct cct gcc    2823
Phe Asp Val Glu Thr Leu Glu Leu Ser Asn Leu Thr Gly Ser Pro Ala
                785                 790                 795 aca cat gtt ctg gat ccg ttt ggc tcg act gcc caa ctg gct tgg gca    2871
Thr His Val Leu Asp Pro Phe Gly Ser Thr Ala Gln Leu Ala Trp Ala
            800                 805                 810 cgt ctg cta aac act tgc acc tac ttc ttt tct gat ttg gaa ttg tca    2919
Arg Leu Leu Asn Thr Cys Thr Tyr Phe Phe Ser Asp Leu Glu Leu Ser
        815                 820                 825 atc cag ttt aaa ttt acc acc act ccg tcc tct gtt gga gag ggc ttt    2967
Ile Gln Phe Lys Phe Thr Thr Thr Pro Ser Ser Val Gly Glu Gly Phe
830                 835                 840 gtg tgg gtg aag tgg ctc cct gtt gga gca cca acc aag acc aca gat    3015
Val Trp Val Lys Trp Leu Pro Val Gly Ala Pro Thr Lys Thr Thr Asp
845                 850                 855                 860 gct tgg cag tta gaa gga ggt gga aat tca gtt aga att caa aaa ttg    3063
Ala Trp Gln Leu Glu Gly Gly Gly Asn Ser Val Arg Ile Gln Lys Leu
                865                 870                 875 gcc gtt gca ggg atg tgc ccc act gtt gtg ttc aag att gca ggc tcc    3111
Ala Val Ala Gly Met Cys Pro Thr Val Val Phe Lys Ile Ala Gly Ser
            880                 885                 890 cgt tca caa gcc tgt gct tca gcg ttg cca tat aca tca atg tgg cgt    3159
Arg Ser Gln Ala Cys Ala Ser Ala Leu Pro Tyr Thr Ser Met Trp Arg
        895                 900                 905
```

```
gtt gtg cca gtc ttt tac aat ggc tgg ggt gca cct acc aaa gaa aag    3207
Val Val Pro Val Phe Tyr Asn Gly Trp Gly Ala Pro Thr Lys Glu Lys
    910                 915                 920 gca acc tac aat tgg ctt cct ggt gca cac ttt ggt tcc atc ttg ctg    3255
Ala Thr Tyr Asn Trp Leu Pro Gly Ala His Phe Gly Ser Ile Leu Leu
925                 930                 935                 940 act tct gat gcg cat gat aaa gga ggg tgc tac ttg cgg tat gct ttc    3303
Thr Ser Asp Ala His Asp Lys Gly Gly Cys Tyr Leu Arg Tyr Ala Phe
                945                 950                 955 cgc gcg cca gcg atg tat tgc cct cga ccc att ccg ccg gct ttt acg    3351
Arg Ala Pro Ala Met Tyr Cys Pro Arg Pro Ile Pro Pro Ala Phe Thr
            960                 965                 970 cgt cca gcg gac aaa acc aga cat aaa ttt ccc act aac atc aac aaa    3399
Arg Pro Ala Asp Lys Thr Arg His Lys Phe Pro Thr Asn Ile Asn Lys
        975                 980                 985 cag tgt act aat tac tct ctc ctc aaa ttg gct gga gat gtt gag agc    3447
Gln Cys Thr Asn Tyr Ser Leu Leu Lys Leu Ala Gly Asp Val Glu Ser
    990                 995                 1000 aac cct ggc ccc act att ttt tcc aaa gca tca gca gac ctg aat gcc    3495
Asn Pro Gly Pro Thr Ile Phe Ser Lys Ala Ser Ala Asp Leu Asn Ala
1005                1010                1015                1020 ttg tca acg tcg cta ggt gaa ttg act ggc atg cta aaa gat ctt aaa    3543
Leu Ser Thr Ser Leu Gly Glu Leu Thr Gly Met Leu Lys Asp Leu Lys
                1025                1030                1035 gcc aag gca gaa act tat tcc ccg ttt tac aaa atg gcc aaa atg ctt    3591
Ala Lys Ala Glu Thr Tyr Ser Pro Phe Tyr Lys Met Ala Lys Met Leu
            1040                1045                1050 ttc aaa ctt gca aca cta gct gtg gca gct atg agg aca aag gac cca    3639
Phe Lys Leu Ala Thr Leu Ala Val Ala Ala Met Arg Thr Lys Asp Pro
        1055                1060                1065 gta gtg gtg gtt atg ttg att gct gat ttc gga ttg gag gtc ttt gac    3687
Val Val Val Val Met Leu Ile Ala Asp Phe Gly Leu Glu Val Phe Asp
    1070                1075                1080 act ggg ttt ttc ttt tcc tac ttt caa gag aag ttg cag cct tat atg    3735
Thr Gly Phe Phe Phe Ser Tyr Phe Gln Glu Lys Leu Gln Pro Tyr Met
1085                1090                1095                1100 aaa act att cct ggt aag att tct gat ttg gtc act gat gcg gct acg    3783
Lys Thr Ile Pro Gly Lys Ile Ser Asp Leu Val Thr Asp Ala Ala Thr
                1105                1110                1115 gct gcc gcc caa att cca aag gga gtg tat tct ttt gtg tcg tca ttt    3831
Ala Ala Ala Gln Ile Pro Lys Gly Val Tyr Ser Phe Val Ser Ser Phe
            1120                1125                1130 ttc gaa acg cct gaa gga gtg gtt gag aag cag gtg tct ctt cgg aca    3879
Phe Glu Thr Pro Glu Gly Val Val Glu Lys Gln Val Ser Leu Arg Thr
        1135                1140                1145 gtg aat gac ata ttt gct ttg ctt aaa aat tct gat tgg ttc ata aag    3927
Val Asn Asp Ile Phe Ala Leu Leu Lys Asn Ser Asp Trp Phe Ile Lys
    1150                1155                1160 act ctt gtt gcc ctc aag aaa tgg ctg aca tcc tgg ttt gct caa gaa    3975
Thr Leu Val Ala Leu Lys Lys Trp Leu Thr Ser Trp Phe Ala Gln Glu
1165                1170                1175                1180 caa cag gca gat gat gcg ctc tat tca gaa ttg gaa aaa tat ccc ttg    4023
Gln Gln Ala Asp Asp Ala Leu Tyr Ser Glu Leu Glu Lys Tyr Pro Leu
                1185                1190                1195 tac aag tta aaa ttg aag gaa cct gat act caa gag gaa gcg cgc cag    4071
Tyr Lys Leu Lys Leu Lys Glu Pro Asp Thr Gln Glu Glu Ala Arg Gln
            1200                1205                1210 tgg ttt aaa gac atg cag cag cgt gct ctc gct gtg aag gac aaa ggt    4119
Trp Phe Lys Asp Met Gln Gln Arg Ala Leu Ala Val Lys Asp Lys Gly
        1215                1220                1225
```

-continued

```
ctc ttt tcc ctc ctg caa att cca tta gtt aac ttg ccc cag agc cgt       4167
Leu Phe Ser Leu Leu Gln Ile Pro Leu Val Asn Leu Pro Gln Ser Arg
    1230                1235                1240 cca gag ccc gtt gta tgc gtc ctt cgg ggc gca tca ggg caa ggc aaa       4215
Pro Glu Pro Val Val Cys Val Leu Arg Gly Ala Ser Gly Gln Gly Lys
1245                1250                1255                1260 tct tat ttg gca aat ctg atg gct caa gca att tcg ctt ctc ttg gtt       4263
Ser Tyr Leu Ala Asn Leu Met Ala Gln Ala Ile Ser Leu Leu Leu Val
        1265                1270                1275 ggc aag cag gac agt gtg tgg agt tgt cct cct gac ccc aca tat ttt       4311
Gly Lys Gln Asp Ser Val Trp Ser Cys Pro Pro Asp Pro Thr Tyr Phe
            1280                1285                1290 gat ggc tat aac gga cag gct gtg gtg att atg gat gca ttg ggc cag       4359
Asp Gly Tyr Asn Gly Gln Ala Val Val Ile Met Asp Ala Leu Gly Gln
                1295                1300                1305 gat ccg aat ggt gct gac ttt aaa tat ttt tgc cag atg gtc tct aca       4407
Asp Pro Asn Gly Ala Asp Phe Lys Tyr Phe Cys Gln Met Val Ser Thr
    1310                1315                1320 aca gct ttt gta cca cct atg gcc cat ttg gat gat aaa ggc att cca       4455
Thr Ala Phe Val Pro Pro Met Ala His Leu Asp Asp Lys Gly Ile Pro
1325                1330                1335                1340 ttt act tct cct gtt gtt att tgt act aca aat ttg cat tca tct ttt       4503
Phe Thr Ser Pro Val Val Ile Cys Thr Thr Asn Leu His Ser Ser Phe
        1345                1350                1355 acc cct att act gtt tct tgt cct gaa gct ctt aag agg agg ttt cgg       4551
Thr Pro Ile Thr Val Ser Cys Pro Glu Ala Leu Lys Arg Arg Phe Arg
            1360                1365                1370 ttt gat gtg acg gtg tcc gct aaa ccg ggc ttt gtg cgc act gtt ggt       4599
Phe Asp Val Thr Val Ser Ala Lys Pro Gly Phe Val Arg Thr Val Gly
                1375                1380                1385 tca aac cag ctt ttg aat ctc cca ctt gct ctt aag cca gct ggt ctt       4647
Ser Asn Gln Leu Leu Asn Leu Pro Leu Ala Leu Lys Pro Ala Gly Leu
    1390                1395                1400 ccc cca cac cct atc ttt gaa aat gac atg ccc att ata aat ggg cag       4695
Pro Pro His Pro Ile Phe Glu Asn Asp Met Pro Ile Ile Asn Gly Gln
1405                1410                1415                1420 gct gtt aaa ttg gct ctt tct ggt gga gaa gtg aca gct ttt gag ctt       4743
Ala Val Lys Leu Ala Leu Ser Gly Gly Glu Val Thr Ala Phe Glu Leu
        1425                1430                1435 att gag atg ata ctg tca gaa gtt caa aac aga caa gac aca cac aaa       4791
Ile Glu Met Ile Leu Ser Glu Val Gln Asn Arg Gln Asp Thr His Lys
            1440                1445                1450 atg ccc att ttt aaa caa tca tgg tct gat ttg ttc aga aag tgt aca       4839
Met Pro Ile Phe Lys Gln Ser Trp Ser Asp Leu Phe Arg Lys Cys Thr
                1455                1460                1465 act gat gag gaa cag aaa atg ttg cag ttt tta att gac aat aaa gat       4887
Thr Asp Glu Glu Gln Lys Met Leu Gln Phe Leu Ile Asp Asn Lys Asp
    1470                1475                1480 tca gaa att ctc agg gcg ttt gtt tca gaa cgc tcc att tta cta cat       4935
Ser Glu Ile Leu Arg Ala Phe Val Ser Glu Arg Ser Ile Leu Leu His
1485                1490                1495                1500 gaa gag tat ctt aaa tgg gag tca tat atg acc agg aga gcc aag ttt       4983
Glu Glu Tyr Leu Lys Trp Glu Ser Tyr Met Thr Arg Arg Ala Lys Phe
        1505                1510                1515 cac cgc ctg gct gct gat ttt gct atg ttt cta tcc att ctt act tca       5031
His Arg Leu Ala Ala Asp Phe Ala Met Phe Leu Ser Ile Leu Thr Ser
            1520                1525                1530 ctg att gtt att ttt tgt tta gtt tat tct atg tat caa ctt ttt aag       5079
Leu Ile Val Ile Phe Cys Leu Val Tyr Ser Met Tyr Gln Leu Phe Lys
```

-continued

```
                    1535                1540                1545 acc cct gac gag caa tca gct tat gat cct tca act aag cca aaa cca    5127
Thr Pro Asp Glu Gln Ser Ala Tyr Asp Pro Ser Thr Lys Pro Lys Pro
    1550                1555                1560 aag acc cag gaa gtg aaa aca ctg aag att agg act gag act ggt gta    5175
Lys Thr Gln Glu Val Lys Thr Leu Lys Ile Arg Thr Glu Thr Gly Val
1565                1570                1575                1580 cca gca act gac ttg caa caa tcc atc atg aaa aat gtt cag cca att    5223
Pro Ala Thr Asp Leu Gln Gln Ser Ile Met Lys Asn Val Gln Pro Ile
        1585                1590                1595 gag ctt tac ctt gac aat gaa ttg gtt act gac tgc tct gcc ttg ggt    5271
Glu Leu Tyr Leu Asp Asn Glu Leu Val Thr Asp Cys Ser Ala Leu Gly
    1600                1605                1610 gtt tat gac aat tca tat ttg gtg ccc ctt cat ttg ttt gaa ttt gat    5319
Val Tyr Asp Asn Ser Tyr Leu Val Pro Leu His Leu Phe Glu Phe Asp
        1615                1620                1625 ttt gat acc att gtg ctt ggt gga cgt cat tac aag aaa gct gag tgt    5367
Phe Asp Thr Ile Val Leu Gly Gly Arg His Tyr Lys Lys Ala Glu Cys
    1630                1635                1640 gag aag gta gag ttt gag ctt gaa gtg aat gga gac gtg gtg tca tca    5415
Glu Lys Val Glu Phe Glu Leu Glu Val Asn Gly Asp Val Val Ser Ser
1645                1650                1655                1660 gat gcg tgt cta ctt cga gtg tca tcg ggg cct aaa gtt aga aat att    5463
Asp Ala Cys Leu Leu Arg Val Ser Ser Gly Pro Lys Val Arg Asn Ile
        1665                1670                1675 gtt cat ctt ttt aca aat gaa att gaa ttg aag aaa atg acc caa gtg    5511
Val His Leu Phe Thr Asn Glu Ile Glu Leu Lys Lys Met Thr Gln Val
    1680                1685                1690 aca gga atc atg aat tca cca cac cag gca cgc act gtg ttt ttt ggc    5559
Thr Gly Ile Met Asn Ser Pro His Gln Ala Arg Thr Val Phe Phe Gly
        1695                1700                1705 agt ttt ttg aca gtg agg aag tcc atc tta aca tcg gat ggg act gta    5607
Ser Phe Leu Thr Val Arg Lys Ser Ile Leu Thr Ser Asp Gly Thr Val
    1710                1715                1720 atg ccc aat gtt ttg tcc tat gcc gct cag acc tcg cgt ggg tat tgt    5655
Met Pro Asn Val Leu Ser Tyr Ala Ala Gln Thr Ser Arg Gly Tyr Cys
1725                1730                1735                1740 ggc gct gca att gtt gct ggc tca cct gcc cgc ata att ggt atc cat    5703
Gly Ala Ala Ile Val Ala Gly Ser Pro Ala Arg Ile Ile Gly Ile His
        1745                1750                1755 tca gct ggc act gga tct gtt gca ttt tgc tcc ctg gtg tcc aga gac    5751
Ser Ala Gly Thr Gly Ser Val Ala Phe Cys Ser Leu Val Ser Arg Asp
    1760                1765                1770 gcg ctg gag caa ctc tgg ccc cag aaa cag ggc aac gtt agt cgc ctt    5799
Ala Leu Glu Gln Leu Trp Pro Gln Lys Gln Gly Asn Val Ser Arg Leu
        1775                1780                1785 gat gac gat gtg agg gtg tct gtt ccg cgc cgc tcc aaa ttg gtg aaa    5847
Asp Asp Asp Val Arg Val Ser Val Pro Arg Arg Ser Lys Leu Val Lys
    1790                1795                1800 tca ttg gct tac ccc att ttc aaa cct gac tat ggc cca gcg cca ctc    5895
Ser Leu Ala Tyr Pro Ile Phe Lys Pro Asp Tyr Gly Pro Ala Pro Leu
1805                1810                1815                1820 tct caa ttt gac aag cgc ctg tca gac ggc gtg aag ctg gat gaa gtg    5943
Ser Gln Phe Asp Lys Arg Leu Ser Asp Gly Val Lys Leu Asp Glu Val
        1825                1830                1835 gtt ttt gct aaa cat act gga gac aag gag att tcc gca cag gac cag    5991
Val Phe Ala Lys His Thr Gly Asp Lys Glu Ile Ser Ala Gln Asp Gln
    1840                1845                1850 aaa tgg ctc ttg cgt gcg gcg cat gta tac gcc cag aag gtt ttc tcc    6039
```

```
Lys Trp Leu Leu Arg Ala Ala His Val Tyr Ala Gln Lys Val Phe Ser
        1855                1860                1865 cgg att gga ttt gac aac cag gct ttg act gaa aaa gag gcc att tgt    6087
Arg Ile Gly Phe Asp Asn Gln Ala Leu Thr Glu Lys Glu Ala Ile Cys
    1870                1875                1880 ggc att cct ggc ctt gac aag atg gag cag gac acc gct ccc ggg ctg    6135
Gly Ile Pro Gly Leu Asp Lys Met Glu Gln Asp Thr Ala Pro Gly Leu
1885                1890                1895                1900 ccc tat gct cag caa aat aag aga agg aaa gac atc tgt gat ttt gaa    6183
Pro Tyr Ala Gln Gln Asn Lys Arg Arg Lys Asp Ile Cys Asp Phe Glu
            1905                1910                1915 gag ggc cgg ctg aag ggc gcc gaa ctc caa aag gac aga ttt atg gct    6231
Glu Gly Arg Leu Lys Gly Ala Glu Leu Gln Lys Asp Arg Phe Met Ala
        1920                1925                1930 ggt gac tac tct aat ttg gtc tat caa tca ttt ttg aaa gat gag atc    6279
Gly Asp Tyr Ser Asn Leu Val Tyr Gln Ser Phe Leu Lys Asp Glu Ile
    1935                1940                1945 cgc cca ctt gag aaa gtt agg gct gga aag acc cgc ctg att gac gtg    6327
Arg Pro Leu Glu Lys Val Arg Ala Gly Lys Thr Arg Leu Ile Asp Val
1950                1955                1960 ccg ccg atg ccc cat gtg gtg gtt ggt agg cag ctc ttg ggc cgg ttt    6375
Pro Pro Met Pro His Val Val Val Gly Arg Gln Leu Leu Gly Arg Phe
1965                1970                1975                1980 gtg gca aaa ttt cat gaa gca aat gga ttt gac att ggc tca gcc att    6423
Val Ala Lys Phe His Glu Ala Asn Gly Phe Asp Ile Gly Ser Ala Ile
            1985                1990                1995 gga tgt gac cca gat gtg gac tgg act cgg ttt ggc ctc gag ttg gag    6471
Gly Cys Asp Pro Asp Val Asp Trp Thr Arg Phe Gly Leu Glu Leu Glu
        2000                2005                2010 cgt ttc agg tat gta tat gcc tgt gac tac tca cgg ttc gat gcc aac    6519
Arg Phe Arg Tyr Val Tyr Ala Cys Asp Tyr Ser Arg Phe Asp Ala Asn
    2015                2020                2025 cat gca gct gat gca atg aga gtt gtg ctt aac tac ttt ttc tct gag    6567
His Ala Ala Asp Ala Met Arg Val Val Leu Asn Tyr Phe Phe Ser Glu
2030                2035                2040 gac cac ggt ttc gac cct ggt gtg cct gct ttt att gag tca ctg gtt    6615
Asp His Gly Phe Asp Pro Gly Val Pro Ala Phe Ile Glu Ser Leu Val
2045                2050                2055                2060 gat tca gtg cat gcc tat gaa gag aaa agg tat aac atc tac ggt ggc    6663
Asp Ser Val His Ala Tyr Glu Glu Lys Arg Tyr Asn Ile Tyr Gly Gly
            2065                2070                2075 ttg cca tcc ggg tgt tcc tgc aca tca att ttg aat acc atc ttg aac    6711
Leu Pro Ser Gly Cys Ser Cys Thr Ser Ile Leu Asn Thr Ile Leu Asn
        2080                2085                2090 aat gtt tac att ctt gca gct atg atg aag gct tat gag aat ttt gag    6759
Asn Val Tyr Ile Leu Ala Ala Met Met Lys Ala Tyr Glu Asn Phe Glu
    2095                2100                2105 cca gat gac att cag gtc att tgc tat ggg gac gac tgc ctc att gct    6807
Pro Asp Asp Ile Gln Val Ile Cys Tyr Gly Asp Asp Cys Leu Ile Ala
2110                2115                2120 tct gat ttt gaa att gat ttc caa caa ctg gtg cct gtc ttt tct agt    6855
Ser Asp Phe Glu Ile Asp Phe Gln Gln Leu Val Pro Val Phe Ser Ser
2125                2130                2135                2140 ttt gga cag gta ata act aca gct gac aag act gat ttt ttt aaa ctg    6903
Phe Gly Gln Val Ile Thr Thr Ala Asp Lys Thr Asp Phe Phe Lys Leu
            2145                2150                2155 aca acg ctt tcg gag gtg acc ttc ctt aag cgc gct ttt gtt ctg acg    6951
Thr Thr Leu Ser Glu Val Thr Phe Leu Lys Arg Ala Phe Val Leu Thr
        2160                2165                2170
```

```
gcc ttt tac aag cca gtg atg gat gtg aag acc ctt gaa gca atc tta    6999
Ala Phe Tyr Lys Pro Val Met Asp Val Lys Thr Leu Glu Ala Ile Leu
         2175                2180                2185 agc ttt gtt cgc cca ggc aca cag gct gaa aag ctc ctg tcc gtg gcg    7047
Ser Phe Val Arg Pro Gly Thr Gln Ala Glu Lys Leu Leu Ser Val Ala
    2190                2195                2200 cag ttg gca ggc cac tgc gaa ccg gag cag tat gag cgc ctg ttt gag    7095
Gln Leu Ala Gly His Cys Glu Pro Glu Gln Tyr Glu Arg Leu Phe Glu
2205                2210                2215                2220 ccc ttt gct ggg atg tat ttc gtc cct act tgg cga ctt gcc cct gca    7143
Pro Phe Ala Gly Met Tyr Phe Val Pro Thr Trp Arg Leu Ala Pro Ala
                2225                2230                2235 gtg gtt gat gaa gct tgg atg cta aat tct ttt tgactttgtt tttctttgtt  7196
Val Val Asp Glu Ala Trp Met Leu Asn Ser Phe
            2240                2245 ttcttttagg cttttaaggt gttaagttta aaggttaaga gttttagaa gttaagatag    7256 agtttagttt ttagttttga gc                                            7278

<210> SEQ ID NO 2
<211> LENGTH: 2247
<212> TYPE: PRT
<213> ORGANISM: equine rhinovirus 1

<400> SEQUENCE: 2

Met Ala Ala Ser Lys Val Tyr Arg Val Cys Glu Gln Thr Leu Leu Ala
 1               5                  10                  15

Gly Ala Val Arg Met Met Asp Lys Phe Leu Gln Lys Arg Thr Val Phe
            20                  25                  30

Val Pro His Leu Asp Lys Thr Ile Arg Leu Thr Gly Leu His Asn Tyr
        35                  40                  45

Asp Asn Thr Cys Trp Leu Asn Ala Leu Thr Gln Leu Thr Gln Ile Leu
    50                  55                  60

Gly Ile Arg Leu Phe Asp Glu His Phe Gly Asn Arg Gly Leu Phe Thr
65                  70                  75                  80

Arg Lys Thr Ile Asp Trp Val Ser Asp Gln Thr Gly Ile Lys Asp Leu
                85                  90                  95

Lys Ser Gly Ala Pro Pro Leu Val Val Tyr Lys Leu Trp Gln His
            100                 105                 110

Gly His Leu Asp Val Gly Thr Met Glu Lys Pro Arg Ser Ile Thr Leu
        115                 120                 125

Trp Ser Gly Pro Lys Val Cys Leu Ser Asp Phe Trp Ala Cys Val Ser
    130                 135                 140

Ala Lys Pro Gly His Ala Val Phe Tyr Leu Leu Thr Ser Glu Gly Trp
145                 150                 155                 160

Ile Cys Val Asp Asp Lys Lys Ile Tyr Pro Glu Thr Pro Lys Thr Glu
                165                 170                 175

Asp Val Leu Val Phe Ala Pro Tyr Asp Phe Glu Ser Leu Gly Lys Asp
            180                 185                 190

Pro Pro Lys Leu His Gln Arg Tyr Glu Lys Ala Phe Glu Leu Ser Gly
        195                 200                 205

Gly Gly Thr Ser Thr Pro Thr Thr Gly Asn Gln Asn Met Ser Gly Asn
    210                 215                 220

Ser Gly Ser Ile Val Gln Asn Phe Tyr Met Gln Gln Tyr Gln Asn Ser
225                 230                 235                 240

Ile Asp Ala Asp Leu Gly Asp Asn Val Ile Ser Pro Glu Gly Gln Gly
                245                 250                 255
```

-continued

```
Ser Asn Thr Ser Ser Thr Ser Ser Gln Ser Ser Gly Leu Gly
        260             265             270

Gly Trp Phe Ser Ser Leu Leu Asn Leu Gly Thr Lys Leu Leu Ala Asp
        275             280             285

Lys Lys Thr Glu Glu Thr Thr Asn Ile Glu Asp Arg Ile Glu Thr Thr
        290             295             300

Val Val Gly Val Thr Ile Ile Asn Ser Gln Gly Ser Val Gly Thr Thr
305             310             315             320

Tyr Cys Tyr Ser Lys Pro Asp Gly Arg Pro Pro Ser Thr Val Ser Asp
            325             330             335

Pro Val Thr Arg Leu Gly Pro Thr Leu Ser Arg His Tyr Thr Phe Lys
            340             345             350

Val Gly Glu Trp Pro His Ser Gln Ser His Gly His Ala Trp Ile Cys
            355             360             365

Pro Leu Pro Gly Asp Lys Leu Lys Lys Met Gly Ser Phe His Glu Val
            370             375             380

Val Lys Ala His His Leu Val Lys Asn Gly Trp Asp Val Val Gln
385             390             395             400

Val Asn Pro Ser Phe Ala His Ser Gly Pro Leu Cys Val Ala Ala Val
            405             410             415

Pro Glu Tyr Glu His Thr His Glu Lys Ala Leu Lys Trp Ser Glu Leu
            420             425             430

Glu Glu Pro Ala Tyr Thr Tyr Gln Gln Leu Ser Val Phe Pro His Gln
            435             440             445

Leu Leu Asn Leu Arg Thr Asn Ser Ser Val His Leu Val Met Pro Tyr
            450             455             460

Ile Gly Pro Gly Gln Pro Thr Asn Leu Thr Leu His Asn Pro Trp Thr
465             470             475             480

Ile Val Ile Leu Ile Leu Ser Glu Leu Thr Gly Pro Gly Gln Thr Val
            485             490             495

Pro Val Thr Met Ser Val Ala Pro Ile Asp Ala Met Val Asn Gly Pro
            500             505             510

Leu Pro Asn Pro Glu Ala Pro Ile Arg Val Val Ser Val Pro Glu Ser
            515             520             525

Asp Ser Phe Met Ser Ser Val Pro Asp Asn Ser Thr Pro Leu Tyr Pro
            530             535             540

Lys Val Val Val Pro Pro Arg Gln Val Pro Gly Arg Phe Thr Asn Phe
545             550             555             560

Ile Asp Val Ala Lys Gln Thr Tyr Ser Phe Cys Ser Ile Ser Gly Lys
            565             570             575

Pro Tyr Phe Glu Val Thr Asn Thr Ser Gly Asp Glu Pro Leu Phe Gln
            580             585             590

Met Asp Val Ser Leu Ser Ala Glu Leu His Gly Thr Tyr Val Ala
            595             600             605

Ser Leu Ser Ser Phe Phe Ala Gln Tyr Arg Gly Ser Leu Asn Phe Asn
            610             615             620

Phe Ile Phe Thr Gly Ala Ala Thr Lys Ala Lys Phe Leu Val Ala
625             630             635             640

Phe Val Pro Pro His Ser Ala Ala Pro Lys Thr Arg Asp Glu Ala Met
            645             650             655

Ala Cys Ile His Ala Val Trp Asp Val Gly Leu Asn Ser Ala Phe Ser
            660             665             670
```

-continued

Phe Asn Val Pro Tyr Pro Ser Pro Ala Asp Phe Met Ala Val Tyr Ser
        675                 680                 685

Ala Glu Arg Thr Val Val Asn Val Ser Gly Trp Leu Gln Val Tyr Ala
    690                 695                 700

Leu Thr Ala Leu Thr Ser Thr Asp Ile Ala Val Asn Ser Lys Gly Arg
705                 710                 715                 720

Val Leu Val Ala Val Ser Ala Gly Pro Asp Phe Ser Leu Arg His Pro
                725                 730                 735

Ala Asp Leu Pro Asp Lys Gln Val Thr Asn Val Gly Glu Asp Gly Glu
            740                 745                 750

Pro Gly Glu Thr Glu Pro Arg His Ala Leu Ser Pro Val Asp Met His
        755                 760                 765

Val His Thr Asp Val Ser Phe Leu Leu Asp Arg Phe Phe Asp Val Glu
    770                 775                 780

Thr Leu Glu Leu Ser Asn Leu Thr Gly Ser Pro Ala Thr His Val Leu
785                 790                 795                 800

Asp Pro Phe Gly Ser Thr Ala Gln Leu Ala Trp Ala Arg Leu Leu Asn
                805                 810                 815

Thr Cys Thr Tyr Phe Phe Ser Asp Leu Glu Leu Ser Ile Gln Phe Lys
            820                 825                 830

Phe Thr Thr Thr Pro Ser Ser Val Gly Glu Gly Phe Val Trp Val Lys
        835                 840                 845

Trp Leu Pro Val Gly Ala Pro Thr Lys Thr Thr Asp Ala Trp Gln Leu
    850                 855                 860

Glu Gly Gly Gly Asn Ser Val Arg Ile Gln Lys Leu Ala Val Ala Gly
865                 870                 875                 880

Met Cys Pro Thr Val Val Phe Lys Ile Ala Gly Ser Arg Ser Gln Ala
                885                 890                 895

Cys Ala Ser Ala Leu Pro Tyr Thr Ser Met Trp Arg Val Val Pro Val
            900                 905                 910

Phe Tyr Asn Gly Trp Gly Ala Pro Thr Lys Glu Lys Ala Thr Tyr Asn
        915                 920                 925

Trp Leu Pro Gly Ala His Phe Gly Ser Ile Leu Leu Thr Ser Asp Ala
    930                 935                 940

His Asp Lys Gly Gly Cys Tyr Leu Arg Tyr Ala Phe Arg Ala Pro Ala
945                 950                 955                 960

Met Tyr Cys Pro Arg Pro Ile Pro Pro Ala Phe Thr Arg Pro Ala Asp
                965                 970                 975

Lys Thr Arg His Lys Phe Pro Thr Asn Ile Asn Lys Gln Cys Thr Asn
            980                 985                 990

Tyr Ser Leu Leu Lys Leu Ala Gly Asp Val Glu Ser Asn Pro Gly Pro
        995                 1000                1005

Thr Ile Phe Ser Lys Ala Ser Ala Asp Leu Asn Ala Leu Ser Thr Ser
    1010                1015                1020

Leu Gly Glu Leu Thr Gly Met Leu Lys Asp Leu Lys Ala Lys Ala Glu
1025                1030                1035                1040

Thr Tyr Ser Pro Phe Tyr Lys Met Ala Lys Met Leu Phe Lys Leu Ala
                1045                1050                1055

Thr Leu Ala Val Ala Ala Met Arg Thr Lys Asp Pro Val Val Val Val
            1060                1065                1070

Met Leu Ile Ala Asp Phe Gly Leu Glu Val Phe Asp Thr Gly Phe Phe
        1075                1080                1085

Phe Ser Tyr Phe Gln Glu Lys Leu Gln Pro Tyr Met Lys Thr Ile Pro

-continued

```
            1090                1095                1100

Gly Lys Ile Ser Asp Leu Val Thr Asp Ala Ala Thr Ala Ala Ala Gln
1105                1110                1115                1120

Ile Pro Lys Gly Val Tyr Ser Phe Val Ser Ser Phe Phe Glu Thr Pro
            1125                1130                1135

Glu Gly Val Val Glu Lys Gln Val Ser Leu Arg Thr Val Asn Asp Ile
            1140                1145                1150

Phe Ala Leu Leu Lys Asn Ser Asp Trp Phe Ile Lys Thr Leu Val Ala
            1155                1160                1165

Leu Lys Lys Trp Leu Thr Ser Trp Phe Ala Gln Glu Gln Gln Ala Asp
1170                1175                1180

Asp Ala Leu Tyr Ser Glu Leu Glu Lys Tyr Pro Leu Tyr Lys Leu Lys
1185                1190                1195                1200

Leu Lys Glu Pro Asp Thr Gln Glu Glu Ala Arg Gln Trp Phe Lys Asp
            1205                1210                1215

Met Gln Gln Arg Ala Leu Ala Val Lys Asp Lys Gly Leu Phe Ser Leu
            1220                1225                1230

Leu Gln Ile Pro Leu Val Asn Leu Pro Gln Ser Arg Pro Glu Pro Val
            1235                1240                1245

Val Cys Val Leu Arg Gly Ala Ser Gly Gln Gly Lys Ser Tyr Leu Ala
            1250                1255                1260

Asn Leu Met Ala Gln Ala Ile Ser Leu Leu Val Gly Lys Gln Asp
1265                1270                1275                1280

Ser Val Trp Ser Cys Pro Pro Asp Pro Thr Tyr Phe Asp Gly Tyr Asn
            1285                1290                1295

Gly Gln Ala Val Val Ile Met Asp Ala Leu Gly Gln Asp Pro Asn Gly
            1300                1305                1310

Ala Asp Phe Lys Tyr Phe Cys Gln Met Val Ser Thr Thr Ala Phe Val
            1315                1320                1325

Pro Pro Met Ala His Leu Asp Asp Lys Gly Ile Pro Phe Thr Ser Pro
            1330                1335                1340

Val Val Ile Cys Thr Thr Asn Leu His Ser Ser Phe Thr Pro Ile Thr
1345                1350                1355                1360

Val Ser Cys Pro Glu Ala Leu Lys Arg Arg Phe Arg Phe Asp Val Thr
            1365                1370                1375

Val Ser Ala Lys Pro Gly Phe Val Arg Thr Val Gly Ser Asn Gln Leu
            1380                1385                1390

Leu Asn Leu Pro Leu Ala Leu Lys Pro Ala Gly Leu Pro Pro His Pro
            1395                1400                1405

Ile Phe Glu Asn Asp Met Pro Ile Ile Asn Gly Gln Ala Val Lys Leu
            1410                1415                1420

Ala Leu Ser Gly Gly Glu Val Thr Ala Phe Glu Leu Ile Glu Met Ile
1425                1430                1435                1440

Leu Ser Glu Val Gln Asn Arg Gln Asp Thr His Lys Met Pro Ile Phe
            1445                1450                1455

Lys Gln Ser Trp Ser Asp Leu Phe Arg Lys Cys Thr Thr Asp Glu Glu
            1460                1465                1470

Gln Lys Met Leu Gln Phe Leu Ile Asp Asn Lys Asp Ser Glu Ile Leu
            1475                1480                1485

Arg Ala Phe Val Ser Glu Arg Ser Ile Leu Leu His Glu Glu Tyr Leu
            1490                1495                1500

Lys Trp Glu Ser Tyr Met Thr Arg Arg Ala Lys Phe His Arg Leu Ala
1505                1510                1515                1520
```

```
Ala Asp Phe Ala Met Phe Leu Ser Ile Leu Thr Ser Leu Ile Val Ile
            1525                1530                1535

Phe Cys Leu Val Tyr Ser Met Tyr Gln Leu Phe Lys Thr Pro Asp Glu
            1540                1545                1550

Gln Ser Ala Tyr Asp Pro Ser Thr Lys Pro Lys Pro Lys Thr Gln Glu
            1555                1560                1565

Val Lys Thr Leu Lys Ile Arg Thr Glu Thr Gly Val Pro Ala Thr Asp
1570                1575                1580

Leu Gln Gln Ser Ile Met Lys Asn Val Gln Pro Ile Glu Leu Tyr Leu
1585                1590                1595                1600

Asp Asn Glu Leu Val Thr Asp Cys Ser Ala Leu Gly Val Tyr Asp Asn
            1605                1610                1615

Ser Tyr Leu Val Pro Leu His Leu Phe Glu Phe Asp Phe Asp Thr Ile
            1620                1625                1630

Val Leu Gly Gly Arg His Tyr Lys Lys Ala Glu Cys Glu Lys Val Glu
            1635                1640                1645

Phe Glu Leu Glu Val Asn Gly Asp Val Val Ser Ser Asp Ala Cys Leu
            1650                1655                1660

Leu Arg Val Ser Ser Gly Pro Lys Val Arg Asn Ile Val His Leu Phe
1665                1670                1675                1680

Thr Asn Glu Ile Glu Leu Lys Lys Met Thr Gln Val Thr Gly Ile Met
            1685                1690                1695

Asn Ser Pro His Gln Ala Arg Thr Val Phe Phe Gly Ser Phe Leu Thr
            1700                1705                1710

Val Arg Lys Ser Ile Leu Thr Ser Asp Gly Thr Val Met Pro Asn Val
            1715                1720                1725

Leu Ser Tyr Ala Ala Gln Thr Ser Arg Gly Tyr Cys Gly Ala Ala Ile
            1730                1735                1740

Val Ala Gly Ser Pro Ala Arg Ile Ile Gly Ile His Ser Ala Gly Thr
1745                1750                1755                1760

Gly Ser Val Ala Phe Cys Ser Leu Val Ser Arg Asp Ala Leu Glu Gln
            1765                1770                1775

Leu Trp Pro Gln Lys Gln Gly Asn Val Ser Arg Leu Asp Asp Asp Val
            1780                1785                1790

Arg Val Ser Val Pro Arg Arg Ser Lys Leu Val Lys Ser Leu Ala Tyr
            1795                1800                1805

Pro Ile Phe Lys Pro Asp Tyr Gly Pro Ala Pro Leu Ser Gln Phe Asp
            1810                1815                1820

Lys Arg Leu Ser Asp Gly Val Lys Leu Asp Glu Val Phe Ala Lys
1825                1830                1835                1840

His Thr Gly Asp Lys Glu Ile Ser Ala Gln Asp Gln Lys Trp Leu Leu
            1845                1850                1855

Arg Ala Ala His Val Tyr Ala Gln Lys Val Phe Ser Arg Ile Gly Phe
            1860                1865                1870

Asp Asn Gln Ala Leu Thr Glu Lys Glu Ala Ile Cys Gly Ile Pro Gly
            1875                1880                1885

Leu Asp Lys Met Glu Gln Asp Thr Ala Pro Gly Leu Pro Tyr Ala Gln
            1890                1895                1900

Gln Asn Lys Arg Arg Lys Asp Ile Cys Asp Phe Glu Glu Gly Arg Leu
1905                1910                1915                1920

Lys Gly Ala Glu Leu Gln Lys Asp Arg Phe Met Ala Gly Asp Tyr Ser
            1925                1930                1935
```

-continued

```
Asn Leu Val Tyr Gln Ser Phe Leu Lys Asp Glu Ile Arg Pro Leu Glu
            1940                1945                1950

Lys Val Arg Ala Gly Lys Thr Arg Leu Ile Asp Val Pro Pro Met Pro
        1955                1960                1965

His Val Val Gly Arg Gln Leu Leu Gly Arg Phe Val Ala Lys Phe
    1970                1975                1980

His Glu Asn Gly Phe Asp Ile Gly Ser Ala Ile Gly Cys Asp Pro
1985                1990                1995                2000

Asp Val Asp Trp Thr Arg Phe Gly Leu Glu Leu Glu Arg Phe Arg Tyr
            2005                2010                2015

Val Tyr Ala Cys Asp Tyr Ser Arg Phe Asp Ala Asn His Ala Ala Asp
        2020                2025                2030

Ala Met Arg Val Val Leu Asn Tyr Phe Ser Glu Asp His Gly Phe
    2035                2040                2045

Asp Pro Gly Val Pro Ala Phe Ile Glu Ser Leu Val Asp Ser Val His
        2050                2055                2060

Ala Tyr Glu Glu Lys Arg Tyr Asn Ile Tyr Gly Gly Leu Pro Ser Gly
2065                2070                2075                2080

Cys Ser Cys Thr Ser Ile Leu Asn Thr Ile Leu Asn Asn Val Tyr Ile
            2085                2090                2095

Leu Ala Ala Met Met Lys Ala Tyr Glu Asn Phe Glu Pro Asp Asp Ile
            2100                2105                2110

Gln Val Ile Cys Tyr Gly Asp Asp Cys Leu Ile Ala Ser Asp Phe Glu
        2115                2120                2125

Ile Asp Phe Gln Gln Leu Val Pro Val Phe Ser Ser Phe Gly Gln Val
    2130                2135                2140

Ile Thr Thr Ala Asp Lys Thr Asp Phe Phe Lys Leu Thr Thr Leu Ser
2145                2150                2155                2160

Glu Val Thr Phe Leu Lys Arg Ala Phe Val Leu Thr Ala Phe Tyr Lys
            2165                2170                2175

Pro Val Met Asp Val Lys Thr Leu Glu Ala Ile Leu Ser Phe Val Arg
        2180                2185                2190

Pro Gly Thr Gln Ala Glu Lys Leu Leu Ser Val Ala Gln Leu Ala Gly
    2195                2200                2205

His Cys Glu Pro Glu Gln Tyr Glu Arg Leu Phe Glu Pro Phe Ala Gly
    2210                2215                2220

Met Tyr Phe Val Pro Thr Trp Arg Leu Ala Pro Ala Val Val Asp Glu
2225                2230                2235                2240

Ala Trp Met Leu Asn Ser Phe
            2245

<210> SEQ ID NO 3
<211> LENGTH: 248
<212> TYPE: PRT
<213> ORGANISM: equine rhinovirus 1

<400> SEQUENCE: 3

Val Thr Asn Val Gly Glu Asp Gly Glu Pro Gly Glu Thr Glu Pro Arg
  1               5                  10                  15

His Ala Leu Ser Pro Val Asp Met His Val His Thr Asp Val Ser Phe
            20                  25                  30

Leu Leu Asp Arg Phe Phe Asp Val Glu Thr Leu Glu Leu Ser Asn Leu
        35                  40                  45

Thr Gly Ser Pro Ala Thr His Val Leu Asp Pro Phe Gly Ser Thr Ala
    50                  55                  60
```

```
Gln Leu Ala Trp Ala Arg Leu Leu Asn Thr Cys Thr Tyr Phe Phe Ser
 65                  70                  75                  80

Asp Leu Glu Leu Ser Ile Gln Phe Lys Phe Thr Thr Thr Pro Ser Ser
                 85                  90                  95

Val Gly Glu Gly Phe Val Trp Val Lys Trp Leu Pro Val Gly Ala Pro
            100                 105                 110

Thr Lys Thr Thr Asp Ala Trp Gln Leu Glu Gly Gly Asn Ser Val
        115                 120                 125

Arg Ile Gln Lys Leu Ala Val Ala Gly Met Cys Pro Thr Val Val Phe
130                 135                 140

Lys Ile Ala Gly Ser Arg Ser Gln Ala Cys Ala Ser Ala Leu Pro Tyr
145                 150                 155                 160

Thr Ser Met Trp Arg Val Val Pro Val Phe Tyr Asn Gly Trp Gly Ala
                165                 170                 175

Pro Thr Lys Glu Lys Ala Thr Tyr Asn Trp Leu Pro Gly Ala His Phe
            180                 185                 190

Gly Ser Ile Leu Leu Thr Ser Asp Ala His Asp Lys Gly Gly Cys Tyr
        195                 200                 205

Leu Arg Tyr Ala Phe Arg Ala Pro Ala Met Tyr Cys Pro Arg Pro Ile
210                 215                 220

Pro Pro Ala Phe Thr Arg Pro Ala Asp Lys Thr Arg His Lys Phe Pro
225                 230                 235                 240

Thr Asn Ile Asn Lys Gln Cys Thr
                245

<210> SEQ ID NO 4
<211> LENGTH: 230
<212> TYPE: PRT
<213> ORGANISM: equine rhinovirus 1

<400> SEQUENCE: 4

Asp Lys Lys Thr Glu Glu Thr Thr Asn Ile Glu Asp Arg Ile Glu Thr
 1               5                  10                  15

Thr Val Val Gly Val Thr Ile Ile Asn Ser Gln Gly Ser Val Gly Thr
                20                  25                  30

Thr Tyr Cys Tyr Ser Lys Pro Asp Gly Arg Pro Pro Ser Thr Val Ser
            35                  40                  45

Asp Pro Val Thr Arg Leu Gly Pro Thr Leu Ser Arg His Tyr Thr Phe
        50                  55                  60

Lys Val Gly Glu Trp Pro His Ser Gln Ser His Gly His Ala Trp Ile
 65                  70                  75                  80

Cys Pro Leu Pro Gly Asp Lys Leu Lys Met Gly Ser Phe His Glu
                 85                 90                  95

Val Val Lys Ala His His Leu Val Lys Asn Gly Trp Asp Val Val Val
            100                 105                 110

Gln Val Asn Pro Ser Phe Ala His Ser Gly Pro Leu Cys Val Ala Ala
        115                 120                 125

Val Pro Glu Tyr Glu His Thr His Glu Lys Ala Leu Lys Trp Ser Glu
130                 135                 140

Leu Glu Glu Pro Ala Tyr Thr Tyr Gln Gln Leu Ser Val Phe Pro His
145                 150                 155                 160

Gln Leu Leu Asn Leu Arg Thr Asn Ser Ser Val His Leu Val Met Pro
                165                 170                 175

Tyr Ile Gly Pro Gly Gln Pro Thr Asn Leu Thr Leu His Asn Pro Trp
```

```
                    180                 185                 190
Thr Ile Val Ile Leu Ile Leu Ser Glu Leu Thr Gly Pro Gly Gln Thr
                195                 200                 205
Val Pro Val Thr Met Ser Val Ala Pro Ile Asp Ala Met Val Asn Gly
            210                 215                 220
Pro Leu Pro Asn Pro Glu
225                 230

<210> SEQ ID NO 5
<211> LENGTH: 226
<212> TYPE: PRT
<213> ORGANISM: equine rhinovirus 1

<400> SEQUENCE: 5

Ala Pro Ile Arg Val Val Ser Val Pro Glu Ser Asp Ser Phe Met Ser
 1               5                  10                  15
Ser Val Pro Asp Asn Ser Thr Pro Leu Tyr Pro Lys Val Val Pro
            20                  25                  30
Pro Arg Gln Val Pro Gly Arg Phe Thr Asn Phe Ile Asp Val Ala Lys
        35                  40                  45
Gln Thr Tyr Ser Phe Cys Ser Ile Ser Gly Lys Pro Tyr Phe Glu Val
    50                  55                  60
Thr Asn Thr Ser Gly Asp Glu Pro Leu Phe Gln Met Asp Val Ser Leu
65                  70                  75                  80
Ser Ala Ala Glu Leu His Gly Thr Tyr Val Ala Ser Leu Ser Ser Phe
                85                  90                  95
Phe Ala Gln Tyr Arg Gly Ser Leu Asn Phe Asn Phe Ile Phe Thr Gly
            100                 105                 110
Ala Ala Ala Thr Lys Ala Lys Phe Leu Val Ala Phe Val Pro Pro His
        115                 120                 125
Ser Ala Ala Pro Lys Thr Arg Asp Glu Ala Met Ala Cys Ile His Ala
    130                 135                 140
Val Trp Asp Val Gly Leu Asn Ser Ala Phe Ser Phe Asn Val Pro Tyr
145                 150                 155                 160
Pro Ser Pro Ala Asp Phe Met Ala Val Tyr Ser Ala Glu Arg Thr Val
                165                 170                 175
Val Asn Val Ser Gly Trp Leu Gln Val Tyr Ala Leu Thr Ala Leu Thr
            180                 185                 190
Ser Thr Asp Ile Ala Val Asn Ser Lys Gly Arg Val Leu Val Ala Val
        195                 200                 205
Ser Ala Gly Pro Asp Phe Ser Leu Arg His Pro Ala Asp Leu Pro Asp
    210                 215                 220
Lys Gln
225

<210> SEQ ID NO 6
<211> LENGTH: 80
<212> TYPE: PRT
<213> ORGANISM: equine rhinovirus 1

<400> SEQUENCE: 6

Gly Gly Gly Thr Ser Thr Pro Thr Gly Asn Gln Asn Met Ser Gly
 1               5                  10                  15
Asn Ser Gly Ser Ile Val Gln Asn Phe Tyr Met Gln Gln Tyr Gln Asn
            20                  25                  30
Ser Ile Asp Ala Asp Leu Gly Asp Asn Val Ile Ser Pro Glu Gly Gln
```

-continued

```
        35                  40                  45

Gly Ser Asn Thr Ser Ser Ser Thr Ser Ser Ser Gln Ser Ser Gly Leu
     50                  55                  60

Gly Gly Trp Phe Ser Ser Leu Leu Asn Leu Gly Thr Lys Leu Leu Ala
 65                  70                  75                  80

<210> SEQ ID NO 7
<211> LENGTH: 744
<212> TYPE: DNA
<213> ORGANISM: equine rhinovirus 1

<400> SEQUENCE: 7
gttaccaatg tgggagagga tggtgaaccc ggtgagacag agcctcgtca tgctttgtca     60
cccgtggaca tgcacgtgca cacagatgtc agtttcttgc ttgaccggtt ctttgatgtt    120
gagacacttg agctttcaaa tttgacaggt tctcctgcca cacatgttct ggatccgttt    180
ggctcgactg cccaactggc ttgggcacgt ctgctaaaca cttgcaccta cttcttttct    240
gatttggaat tgtcaatcca gtttaaattt accaccactc cgtcctctgt tggagagggc    300
tttgtgtggg tgaagtggct ccctgttgga gcaccaacca agaccacaga tgcttggcag    360
ttagaaggag gtggaaattc agttagaatt caaaaattgg ccgttgcagg gatgtgcccc    420
actgttgtgt tcaagattgc aggctcccgt tcacaagcct gtgcttcagc gttgccatat    480
acatcaatgt ggcgtgttgt gccagtcttt tacaatggct ggggtgcacc taccaaagaa    540
aaggcaacct acaattggct tcctggtgca cactttggtt ccatcttgct gacttctgat    600
gcgcatgata aaggagggtg ctacttgcgg tatgctttcc gcgcgccagc gatgtattgc    660
cctcgaccca ttccgccggc ttttacgcgt ccagcggaca aaaccagaca taaatttccc    720
actaacatca acaaacagtg tact                                           744

<210> SEQ ID NO 8
<211> LENGTH: 690
<212> TYPE: DNA
<213> ORGANISM: equine rhinovirus 1

<400> SEQUENCE: 8
gacaagaaga cagaagagac tacaaacatt gaagacagaa ttgaaacaac agtggttgga     60
gtcactatta ttaattcaca aggatctgtt ggaacaacct actgttactc caaaccggat    120
ggtagaccac catccacagt gtcagaccca gttaccagac ttggacccac gctttccagg    180
cactacacat ttaaggtagg tgagtggccc cattctcaat cacatggtca cgcatggatc    240
tgtccgttgc caggtgacaa actcaagaag atgggcagtt ttcatgaggt tgtcaaagcc    300
caccacctgg tcaagaacgg ctgggatgtg gttgtgcagg tgaatccctc atttgctcac    360
tccgggccgc tgtgtgtagc agcagtgccg gagtacgaac acacacatga gaaagcactc    420
aagtggtctg agcttgagga accagcttac acataccaac aactttcagt ttttccccac    480
cagttgctaa atttgaggac aaattcatca gtgcatttgg tgatgcccta cattgggcca    540
ggccaaccaa caaatctgac tttgcacaac ccgtggacca ttgttatttt aattttgtct    600
gaattgacag gacctggcca aactgtgcct gtgaccatgt cggtggctcc catcgatgca    660
atggttaatg ggcctcttcc aaatccagag                                     690

<210> SEQ ID NO 9
<211> LENGTH: 678
<212> TYPE: DNA
<213> ORGANISM: equine rhinovirus 1
```

<400> SEQUENCE: 9

| | | | | | |
|---|---|---|---|---|---|
| gcaccgatta | gagtggtgtc | tgtgcctgaa | tcagattctt | ttatgtcttc | agtacctgat | 60 |
| aattcgactc | cactataccc | caaggttgtg | gtcccaccgc | gccaagttcc | tggccggttt | 120 |
| acaaatttca | ttgatgtggc | aaaacagaca | tattcattt | gttccatttc | tggaaaacct | 180 |
| tattttgagg | ttaccaacac | ctctggggac | gagccactgt | tcagatgga | tgtgtcgctc | 240 |
| agtgcggcag | agctacatgg | cacttacgta | gctagtttgt | catcattttt | tgcacagtac | 300 |
| agaggctcac | ttaatttcaa | ctttattttc | actggtgcag | cagccactaa | ggcaaagttt | 360 |
| ctggttgctt | ttgtgcctcc | ccacagtgca | gcgcccaaaa | cgcgcgatga | agcaatggcg | 420 |
| tgcatccatg | ccgtgtggga | tgttggcttg | aactcagctt | tttctttaa | tgtaccttat | 480 |
| ccctcccctg | ctgacttcat | ggccgtttat | tctgcggaac | ggacggttgt | gaatgtctct | 540 |
| ggatggcttc | aagtttatgc | actaacagct | ctaacttcaa | ctgacattgc | cgtgaacagt | 600 |
| aaaggccgtg | tgctggttgc | tgtttccgcc | ggcccagact | tctcccttcg | tcacccggcg | 660 |
| gacctgcccg | acaagcag | | | | | 678 |

<210> SEQ ID NO 10
<211> LENGTH: 240
<212> TYPE: DNA
<213> ORGANISM: equine rhinovirus 1

<400> SEQUENCE: 10

| | | | | | |
|---|---|---|---|---|---|
| ggcggaggta | catccactcc | aacaactggc | aaccaaaaca | tgtccggaaa | cagtggttca | 60 |
| attgttcaaa | attttacat | gcaacagtac | cagaattcaa | ttgacgcaga | cctgggagac | 120 |
| aatgtgatta | gccctgaagg | ccagggcagc | aacactagta | gttcaacctc | atcaagccaa | 180 |
| tcctctggct | tgggcgggtg | gttctctagt | ttgctgaacc | ttggaacaaa | actactggct | 240 |

<210> SEQ ID NO 11
<211> LENGTH: 21
<212> TYPE: DNA
<213> ORGANISM: equine rhinovirus 1

<400> SEQUENCE: 11
gttgtgttca agattgcagg c           21

<210> SEQ ID NO 12
<211> LENGTH: 20
<212> TYPE: DNA
<213> ORGANISM: equine rhinovirus 1

<400> SEQUENCE: 12
ttgctctcaa catctccagc           20

<210> SEQ ID NO 13
<211> LENGTH: 22
<212> TYPE: DNA
<213> ORGANISM: equine rhinovirus 1

<400> SEQUENCE: 13
tagcaccctc ctttatcatg cg           22

<210> SEQ ID NO 14
<211> LENGTH: 33
<212> TYPE: DNA
<213> ORGANISM: equine rhinovirus 1

-continued

```
<400> SEQUENCE: 14
gctggatcca tgagtggcgg aggtacatcc act                              33

<210> SEQ ID NO 15
<211> LENGTH: 30
<212> TYPE: DNA
<213> ORGANISM: equine rhinovirus 1

<400> SEQUENCE: 15
gctctgcagc aggtctgctg atgctttgga                                  30

<210> SEQ ID NO 16
<211> LENGTH: 32
<212> TYPE: DNA
<213> ORGANISM: equine rhinovirus 1

<400> SEQUENCE: 16
gctctgcaga tgattaggac tgagactggt gt                               32

<210> SEQ ID NO 17
<211> LENGTH: 30
<212> TYPE: DNA
<213> ORGANISM: equine rhinovirus 1

<400> SEQUENCE: 17
gctggatcct tagccatagt caggtttgaa                                  30

<210> SEQ ID NO 18
<211> LENGTH: 25
<212> TYPE: DNA
<213> ORGANISM: equine rhinovirus 1

<400> SEQUENCE: 18
atccagcaag ccgctgtccg gttac                                       25

<210> SEQ ID NO 19
<211> LENGTH: 18
<212> TYPE: DNA
<213> ORGANISM: equine rhinovirus 1

<400> SEQUENCE: 19
cgaagagaca cctgcttc                                               18

<210> SEQ ID NO 20
<211> LENGTH: 21
<212> TYPE: DNA
<213> ORGANISM: equine rhinovirus 1

<400> SEQUENCE: 20
ttctggtgga gaagtgacag c                                           21

<210> SEQ ID NO 21
<211> LENGTH: 19
<212> TYPE: DNA
<213> ORGANISM: equine rhinovirus 1

<400> SEQUENCE: 21
gtgagccagc aacaattgc                                              19

<210> SEQ ID NO 22
<211> LENGTH: 865
<212> TYPE: DNA
<213> ORGANISM: equine rhinovirus 1
```

```
<220> FEATURE:
<221> NAME/KEY: CDS
<222> LOCATION: (794)..(865)

<400> SEQUENCE: 22
taagtaaaac gctgtaactg catgatttgc gcctgtagcg ccagtaaaac gcagaaacca      60
caagcaaaaa cctgtagcgt cagtaaaacg cgcacattca catacagagc ttcccggctt     120
taagggttac tgctcgtaat gagagcacat gacaacttgt cgagattacg caactgtca     180 cgggagagag gagcccgttt tcgggcactt gtctcctaaa caatgttggc gcgcatttgc     240
gcgccccccc ccttttttcag cccccctgtca ttgactggtc gaagcgttcg caataagact     300
ggtcgtcact tggctgttct atcgtttcag gctttagcgc gcccttgcgc ggcgggccgt     360
caagcccgtg cgctgtatag cgccaggtaa ccggacagcg gcgtgctgga ttttcccggt     420
gccattgctc tggatggtgt caccaagctg acaaatgcgg agtgaacctc acaaagcgac     480
acgcctgtgg tagcgctgcc caaaagggag cggaactccc cgccgaggcg gtcctctctg     540
gccaaaagcc cagcgttgat agcgcctttt gggatgcagg aaccccacct gccaggtgtg     600
aagtggagtg agcggatctc caatttggtc tgttctgaac tacaccatttt actgctgtga     660 agaatgccct ggaggcaagc tggttacagc cctgaccagg ccctgcccgt gactctcgac     720
cggcgcaggg tcaaaaattg tctaagcagc agcaggaacg cgggagcgtt tcttttcctt     780
ttgtactgac atg atg gcg gcg tct aag gtg tat aga gtt tgc gag cag         829
            Met Ala Ala Ser Lys Val Tyr Arg Val Cys Glu Gln
              1               5                  10 act ctg ctg gca ggt gcc gtt cgc atg atg gac aaa                        865
Thr Leu Leu Ala Gly Ala Val Arg Met Met Asp Lys
         15                  20

<210> SEQ ID NO 23
<211> LENGTH: 24
<212> TYPE: PRT
<213> ORGANISM: equine rhinovirus 1

<400> SEQUENCE: 23

Met Ala Ala Ser Lys Val Tyr Arg Val Cys Glu Gln Thr Leu Leu Ala
  1               5                  10                  15

Gly Ala Val Arg Met Met Asp Lys
             20

<210> SEQ ID NO 24
<211> LENGTH: 2318
<212> TYPE: PRT
<213> ORGANISM: Foot-and-mouth disease virus

<400> SEQUENCE: 24

Met Asn Thr Thr Asp Cys Phe Ile Ala Leu Val Gln Ala Ile Arg Glu
  1               5                  10                  15

Ile Lys Ala Leu Phe Leu Ser Arg Thr Thr Gly Lys Met Glu Leu Thr
             20                  25                  30

Leu Tyr Asn Gly Glu Lys Lys Thr Phe Tyr Ser Arg Pro Asn Asn His
         35                  40                  45

Asp Asn Cys Trp Leu Asn Ala Ile Leu Gln Leu Phe Arg Tyr Val Glu
     50                  55                  60

Glu Pro Phe Phe Asp Trp Val Tyr Ser Ser Pro Glu Asn Leu Thr Leu
 65                  70                  75                  80

Glu Ala Ile Lys Gln Leu Glu Asp Leu Thr Gly Leu Glu Leu His Glu
                 85                  90                  95
```

-continued

```
Gly Gly Pro Pro Ala Leu Val Ile Trp Asn Ile Lys His Leu Leu His
            100                 105                 110
Thr Gly Ile Gly Thr Ala Ser Arg Pro Ser Glu Val Cys Met Val Asp
            115                 120                 125
Gly Thr Asp Met Cys Leu Ala Asp Phe His Ala Gly Ile Phe Leu Lys
130                 135                 140
Gly Gln Glu His Ala Val Phe Ala Cys Val Thr Ser Asn Gln Trp Tyr
145                 150                 155                 160
Ala Ile Asp Asp Glu Asp Phe Tyr Pro Trp Thr Pro Asp Pro Ser Asp
                165                 170                 175
Val Leu Val Phe Val Pro Tyr Asp Gln Glu Pro Leu Asn Gly Glu Trp
            180                 185                 190
Lys Ala Lys Val Gln Arg Lys Leu Lys Gly Ala Gly Gln Ser Ser Pro
            195                 200                 205
Ala Thr Gly Ser Gln Asn Gln Ser Gly Asn Thr Gly Ser Ile Ile Asn
            210                 215                 220
Asn Tyr Tyr Met Gln Gln Tyr Gln Asn Ser Met Asp Thr Gln Leu Gly
225                 230                 235                 240
Asp Asn Ala Ile Ser Gly Gly Ser Asn Glu Gly Ser Thr Asp Thr Thr
                245                 250                 255
Ser Thr His Thr Thr Asn Thr Gln Asn Asn Asp Trp Phe Ser Lys Leu
            260                 265                 270
Ala Ser Ser Ala Phe Ser Gly Leu Phe Gly Ala Leu Leu Ala Asp Lys
            275                 280                 285
Lys Thr Glu Glu Thr Thr Leu Leu Glu Asp Arg Ile Leu Thr Thr Arg
            290                 295                 300
Asn Gly His Thr Thr Ser Thr Thr Gln Ser Ser Val Gly Val Thr Tyr
305                 310                 315                 320
Gly Tyr Ala Thr Ala Glu Asp Phe Val Ser Gly Pro Asn Thr Ser Gly
                325                 330                 335
Leu Glu Thr Arg Val Val Gln Ala Glu Arg Phe Phe Lys Thr His Leu
            340                 345                 350
Phe Asp Trp Val Thr Ser Asp Ser Phe Gly Arg Cys His Leu Leu Glu
            355                 360                 365
Leu Pro Thr Asp His Lys Gly Val Tyr Gly Ser Leu Thr Asp Ser Tyr
370                 375                 380
Ala Tyr Met Arg Asn Gly Trp Asp Val Glu Val Thr Ala Val Gly Asn
385                 390                 395                 400
Gln Phe Asn Gly Gly Cys Leu Leu Val Ala Met Val Pro Glu Leu Tyr
                405                 410                 415
Ser Ile Gln Lys Arg Glu Leu Tyr Gln Leu Thr Leu Phe Pro His Gln
            420                 425                 430
Phe Ile Asn Pro Arg Thr Asn Met Thr Ala His Ile Thr Val Pro Phe
            435                 440                 445
Val Gly Val Asn Arg Tyr Asp Gln Tyr Lys Val His Lys Pro Trp Thr
            450                 455                 460
Leu Val Val Met Val Val Ala Pro Leu Thr Val Asn Thr Glu Gly Ala
465                 470                 475                 480
Pro Gln Ile Lys Val Tyr Ala Asn Ile Ala Pro Thr Asn Val His Val
                485                 490                 495
Ala Gly Glu Phe Pro Ser Lys Glu Gly Ile Phe Pro Val Ala Cys Ser
            500                 505                 510
```

-continued

```
Asp Gly Tyr Gly Gly Leu Val Thr Thr Asp Pro Lys Thr Ala Asp Pro
            515                 520                 525

Val Tyr Gly Lys Val Phe Asn Pro Pro Arg Asn Gln Leu Pro Gly Arg
    530                 535                 540

Phe Thr Asn Leu Leu Asp Val Ala Glu Ala Cys Pro Thr Phe Leu Arg
545                 550                 555                 560

Phe Glu Gly Gly Val Pro Tyr Val Thr Thr Lys Thr Asp Ser Asp Arg
                565                 570                 575

Val Leu Ala Gln Phe Asp Met Ser Leu Ala Ala Lys Gln Met Ser Asn
            580                 585                 590

Thr Phe Leu Ala Gly Leu Ala Gln Tyr Tyr Thr Gln Tyr Ser Gly Thr
        595                 600                 605

Ile Asn Leu His Phe Met Phe Thr Gly Pro Thr Asp Ala Lys Ala Arg
    610                 615                 620

Tyr Met Val Ala Tyr Ala Pro Pro Gly Met Glu Pro Pro Lys Thr Pro
625                 630                 635                 640

Glu Ala Ala His Cys Ile His Ala Glu Trp Asp Thr Gly Leu Asn
                645                 650                 655

Ser Lys Phe Thr Phe Ser Ile Pro Tyr Leu Ser Ala Ala Asp Tyr Ala
            660                 665                 670

Tyr Thr Ala Ser Gly Val Ala Glu Thr Thr Asn Val Gln Gly Trp Val
        675                 680                 685

Cys Leu Phe Gln Ile Thr His Gly Lys Ala Asp Gly Asp Ala Leu Val
690                 695                 700

Val Leu Ala Ser Ala Gly Lys Asp Phe Glu Leu Arg Leu Pro Val Asp
705                 710                 715                 720

Ala Arg Ala Glu Thr Thr Ser Ala Gly Glu Ser Ala Asp Pro Val Thr
                725                 730                 735

Thr Thr Val Glu Asn Tyr Gly Gly Glu Thr Gln Ile Gln Arg Arg Gln
            740                 745                 750

His Thr Asp Val Ser Phe Ile Met Asp Arg Phe Val Lys Val Thr Pro
        755                 760                 765

Gln Asn Gln Ile Asn Ile Leu Asp Leu Met Gln Ile Pro Ser His Thr
770                 775                 780

Leu Val Gly Ala Leu Leu Arg Ala Ser Thr Tyr Tyr Phe Ser Asp Leu
785                 790                 795                 800

Glu Ile Ala Val Lys His Glu Gly Asp Leu Thr Trp Val Pro Asn Gly
                805                 810                 815

Ala Pro Glu Lys Ala Leu Asp Asn Thr Thr Asn Pro Thr Ala Tyr His
            820                 825                 830

Lys Ala Pro Leu Thr Arg Leu Ala Leu Pro Tyr Thr Ala Pro His Arg
        835                 840                 845

Val Leu Ala Thr Val Tyr Asn Gly Glu Cys Arg Tyr Asn Arg Asn Ala
    850                 855                 860

Val Pro Asn Leu Arg Gly Asp Leu Gln Val Leu Ala Gln Lys Val Ala
865                 870                 875                 880

Arg Thr Leu Pro Thr Ser Phe Asn Tyr Gly Ala Ile Lys Ala Thr Arg
                885                 890                 895

Val Thr Glu Leu Leu Tyr Arg Met Lys Arg Ala Glu Thr Tyr Cys Pro
            900                 905                 910

Arg Pro Leu Leu Ala Ile His Pro Thr Glu Ala Arg His Lys Gln Lys
        915                 920                 925

Ile Val Ala Pro Val Lys Gln Thr Leu Asn Phe Asp Leu Leu Lys Leu
```

-continued

```
          930              935              940
Ala Gly Asp Val Glu Ser Asn Pro Gly Pro Phe Phe Ser Asp Val
945              950              955              960
Arg Ser Asn Phe Ser Lys Leu Val Glu Thr Ile Asn Gln Met Gln Glu
             965              970              975
Asp Met Ser Thr Lys His Gly Pro Asp Phe Asn Arg Leu Val Ser Ala
             980              985              990
Phe Glu Glu Leu Ala Ile Gly Val Lys Ala Ile Arg Thr Gly Leu Asp
             995              1000             1005
Glu Ala Lys Pro Trp Tyr Lys Leu Ile Lys Leu Leu Ser Arg Leu Ser
1010             1015             1020
Cys Met Ala Ala Val Ala Ala Arg Ser Lys Asp Pro Val Leu Val Ala
1025             1030             1035             1040
Ile Met Leu Ala Asp Thr Gly Leu Glu Ile Leu Asp Ser Thr Phe Val
             1045             1050             1055
Val Lys Lys Ile Ser Asp Ser Leu Ser Ser Leu Phe His Val Pro Ala
             1060             1065             1070
Pro Val Phe Ser Phe Gly Ala Pro Val Leu Leu Ala Gly Leu Val Lys
             1075             1080             1085
Val Ala Ser Ser Phe Phe Arg Ser Thr Pro Glu Asp Leu Glu Arg Ala
             1090             1095             1100
Glu Lys Gln Leu Lys Ala Arg Asp Ile Asn Asp Ile Phe Ala Ile Leu
1105             1110             1115             1120
Lys Asn Gly Glu Trp Leu Val Lys Leu Ile Leu Ala Ile Arg Asp Trp
             1125             1130             1135
Ile Lys Ala Trp Ile Ala Ser Glu Glu Lys Phe Val Thr Met Thr Asp
             1140             1145             1150
Leu Val Pro Gly Ile Leu Glu Lys Gln Arg Asp Leu Asn Asp Pro Ser
             1155             1160             1165
Lys Tyr Lys Glu Ala Lys Glu Trp Leu Asp Asn Ala Arg Gln Ala Cys
    1170             1175             1180
Leu Lys Ser Gly Asn Val His Ile Ala Asn Leu Cys Lys Val Val Ala
1185             1190             1195             1200
Pro Ala Pro Ser Lys Ser Arg Pro Glu Pro Val Val Val Cys Leu Arg
             1205             1210             1215
Gly Lys Ser Gly Gln Gly Lys Ser Phe Leu Ala Asn Val Leu Ala Gln
             1220             1225             1230
Ala Ile Ser Thr His Phe Thr Gly Arg Ile Asp Ser Val Trp Tyr Cys
             1235             1240             1245
Pro Pro Asp Pro Asp His Phe Asp Gly Tyr Asn Gln Gln Thr Val Val
1250             1255             1260
Val Met Asp Asp Leu Gly Gln Asn Pro Asp Gly Lys Asp Phe Lys Tyr
1265             1270             1275             1280
Phe Ala Gln Met Val Ser Thr Thr Gly Phe Ile Pro Pro Met Ala Ser
             1285             1290             1295
Leu Glu Asp Lys Gly Lys Pro Phe Asn Ser Lys Val Ile Ile Ala Thr
             1300             1305             1310
Thr Asn Leu Tyr Ser Gly Phe Thr Pro Arg Thr Met Val Cys Pro Asp
             1315             1320             1325
Ala Leu Asn Arg Arg Phe His Phe Asp Ile Asp Val Ser Ala Lys Asp
             1330             1335             1340
Gly Tyr Lys Ile Asn Ser Lys Leu Asp Ile Ile Lys Ala Leu Glu Asp
1345             1350             1355             1360
```

-continued

Thr His Ala Asn Pro Val Ala Met Phe Gln Tyr Asp Cys Ala Leu Leu
            1365                1370                1375

Asn Gly Met Ala Val Glu Met Lys Arg Met Gln Gln Asp Met Phe Lys
            1380                1385                1390

Pro Gln Pro Pro Leu Gln Asn Val Tyr Gln Leu Val Gln Glu Val Ile
            1395                1400                1405

Asp Arg Val Glu Leu His Glu Lys Val Ser Ser His Pro Ile Phe Lys
    1410                1415                1420

Gln Ile Ser Ile Pro Ser Gln Lys Ser Val Leu Tyr Phe Leu Ile Glu
1425                1430                1435                1440

Lys Gly Gln His Glu Ala Ala Ile Glu Phe Phe Glu Gly Met Val His
            1445                1450                1455

Asp Ser Ile Lys Glu Glu Leu Arg Pro Leu Ile Gln Gln Thr Ser Phe
            1460                1465                1470

Val Lys Arg Ala Phe Lys Arg Leu Lys Glu Asn Phe Glu Ile Val Ala
    1475                1480                1485

Leu Cys Leu Thr Leu Leu Ala Asn Ile Val Ile Met Ile Arg Glu Thr
            1490                1495                1500

Arg Lys Arg Gln Lys Met Val Asp Asp Ala Val Asn Glu Tyr Ile Glu
1505                1510                1515                1520

Lys Ala Asn Ile Thr Thr Asp Asp Lys Thr Leu Asp Glu Ala Glu Lys
            1525                1530                1535

Ser Pro Leu Glu Thr Ser Gly Ala Ser Thr Val Gly Phe Arg Glu Arg
            1540                1545                1550

Thr Leu Pro Gly Gln Lys Ala Cys Asp Asp Val Asn Ser Glu Pro Ala
            1555                1560                1565

Gln Pro Val Glu Glu Gln Pro Gln Ala Glu Gly Pro Tyr Ala Gly Pro
    1570                1575                1580

Leu Glu Arg Gln Lys Pro Leu Lys Val Arg Ala Lys Leu Pro Gln Gln
1585                1590                1595                1600

Glu Gly Pro Tyr Ala Gly Pro Met Glu Arg Gln Lys Pro Leu Lys Val
            1605                1610                1615

Lys Ala Lys Ala Pro Val Val Lys Glu Gly Pro Tyr Glu Gly Pro Val
            1620                1625                1630

Lys Lys Pro Val Ala Leu Lys Val Lys Ala Lys Asn Leu Ile Val Thr
    1635                1640                1645

Glu Ser Gly Ala Pro Pro Thr Asp Leu Gln Lys Met Val Met Gly Asn
    1650                1655                1660

Thr Lys Pro Val Glu Leu Ile Leu Asp Gly Lys Thr Val Ala Ile Cys
1665                1670                1675                1680

Cys Ala Thr Gly Val Phe Gly Thr Ala Tyr Leu Val Pro Arg His Leu
            1685                1690                1695

Phe Ala Glu Lys Tyr Asp Lys Ile Met Val Asp Gly Arg Ala Met Thr
            1700                1705                1710

Asp Ser Asp Tyr Arg Val Phe Glu Phe Glu Ile Lys Val Lys Gly Gln
    1715                1720                1725

Asp Met Leu Ser Asp Ala Ala Leu Met Val Leu His Arg Gly Asn Arg
    1730                1735                1740

Val Arg Asp Ile Thr Lys His Phe Arg Asp Thr Ala Arg Met Lys Lys
1745                1750                1755                1760

Gly Thr Pro Val Val Gly Val Ile Asn Asn Ala Asp Val Gly Arg Leu
            1765                1770                1775

```
Ile Phe Ser Gly Glu Ala Leu Thr Tyr Lys Asp Ile Val Val Cys Met
            1780                1785                1790

Asp Gly Asp Thr Met Pro Gly Leu Phe Ala Tyr Arg Ala Ala Thr Lys
        1795                1800                1805

Ala Gly Tyr Cys Gly Gly Ala Val Leu Ala Lys Asp Gly Ala Asp Thr
    1810                1815                1820

Phe Ile Val Gly Thr His Ser Ala Gly Asn Gly Val Gly Tyr Cys
1825                1830                1835                1840

Ser Cys Val Ser Arg Ser Met Leu Leu Lys Met Lys Ala His Ile Asp
            1845                1850                1855

Pro Glu Pro His His Glu Gly Leu Ile Val Asp Thr Arg Asp Val Glu
        1860                1865                1870

Glu Arg Val His Val Met Arg Lys Thr Lys Leu Ala Pro Thr Val Ala
    1875                1880                1885

His Gly Val Phe Asn Pro Glu Phe Gly Pro Ala Ala Leu Ser Asn Lys
1890                1895                1900

Asp Pro Arg Leu Asn Glu Gly Val Val Leu Asp Glu Val Ile Phe Ser
1905                1910                1915                1920

Lys His Lys Gly Asp Thr Lys Met Ser Glu Glu Asp Lys Ala Leu Phe
        1925                1930                1935

Arg Arg Cys Ala Ala Asp Tyr Ala Ser Arg Leu His Ser Val Leu Gly
            1940                1945                1950

Thr Ala Asn Ala Pro Leu Ser Ile Tyr Glu Ala Ile Lys Gly Val Asp
        1955                1960                1965

Gly Leu Asp Ala Met Glu Pro Asp Thr Ala Pro Gly Leu Pro Trp Ala
    1970                1975                1980

Leu Gln Gly Lys Arg Arg Gly Ala Leu Ile Asp Phe Glu Asn Gly Thr
1985                1990                1995                2000

Val Gly Pro Glu Val Glu Ala Ala Leu Lys Leu Met Glu Lys Arg Glu
        2005                2010                2015

Tyr Lys Phe Val Cys Gln Thr Phe Leu Lys Asp Glu Ile Arg Pro Leu
            2020                2025                2030

Glu Lys Val Arg Ala Gly Lys Thr Arg Ile Val Asp Val Leu Pro Val
        2035                2040                2045

Glu His Ile Leu Tyr Thr Arg Met Met Ile Gly Arg Phe Cys Ala Gln
    2050                2055                2060

Met His Ser Asn Asn Gly Pro Gln Ile Gly Ser Ala Val Gly Cys Asn
2065                2070                2075                2080

Pro Asp Val Asp Trp Gln Arg Phe Gly Thr His Phe Ala Gln Tyr Arg
        2085                2090                2095

Asn Val Trp Asp Val Asp Tyr Ser Ala Phe Asp Ala Asn His Cys Ser
            2100                2105                2110

Asp Ala Met Asn Ile Met Phe Glu Glu Val Phe Arg Thr Glu Phe Gly
        2115                2120                2125

Phe His Pro Asn Ala Glu Trp Ile Leu Lys Thr Leu Val Asn Thr Glu
    2130                2135                2140

His Ala Tyr Glu Asn Lys Arg Ile Thr Val Gly Gly Gly Met Pro Ser
2145                2150                2155                2160

Gly Cys Ser Ala Thr Ser Ile Ile Asn Thr Ile Leu Asn Asn Ile Tyr
            2165                2170                2175

Val Leu Tyr Ala Leu Arg Arg His Tyr Glu Gly Val Glu Leu Asp Thr
        2180                2185                2190

Tyr Thr Met Ile Ser Tyr Gly Asp Asp Ile Val Val Ala Ser Asp Tyr
```

-continued

```
                2195                  2200                  2205

Asp Leu Asp Phe Glu Ala Leu Lys Pro His Phe Lys Ser Leu Gly Gln
            2210                  2215                  2220

Thr Ile Thr Pro Ala Asp Lys Ser Asp Lys Gly Phe Val Leu Gly His
2225                  2230                  2235                  2240

Ser Ile Thr Asp Val Thr Phe Leu Lys Arg His Phe His Met Asp Tyr
                2245                  2250                  2255

Gly Thr Gly Phe Tyr Lys Pro Val Met Ala Ser Lys Thr Leu Glu Ala
            2260                  2265                  2270

Ile Leu Ser Phe Ala Arg Arg Gly Thr Ile Gln Glu Lys Leu Ile Ser
        2275                  2280                  2285

Val Ala Gly Leu Ala Val His Ser Gly Pro Asp Glu Tyr Arg Arg Leu
    2290                  2295                  2300

Phe Glu Pro Phe Gln Gly Leu Phe Glu Ile Pro Ser Tyr Arg
2305                  2310                  2315

<210> SEQ ID NO 25
<211> LENGTH: 2232
<212> TYPE: PRT
<213> ORGANISM: equine rhinovirus 1

<400> SEQUENCE: 25

Met Ala Ala Ser Lys Val Tyr Arg Val Cys Glu Gln Thr Leu Leu Ala
 1               5                  10                  15

Gly Ala Val Arg Met Met Asp Lys Phe Leu Gln Lys Arg Thr Val Phe
            20                  25                  30

Val Pro His Leu Asp Lys Thr Ile Arg Leu Thr Gly Leu His Asn Tyr
        35                  40                  45

Asp Asn Thr Cys Trp Leu Asn Ala Leu Thr Gln Leu Thr Gln Ile Leu
    50                  55                  60

Gly Ile Arg Leu Phe Asp Glu His Phe Gly Asn Arg Gly Leu Phe Thr
65                  70                  75                  80

Arg Lys Thr Ile Asp Trp Val Ser Asp Gln Thr Gly Ile Lys Asp Leu
                85                  90                  95

Lys Ser Gly Ala Pro Pro Leu Val Val Tyr Lys Leu Trp Gln His
            100                 105                 110

Gly His Leu Asp Val Gly Thr Met Glu Lys Pro Arg Ser Ile Thr Leu
        115                 120                 125

Trp Ser Gly Pro Lys Val Cys Leu Ser Asp Phe Trp Ala Cys Val Ser
    130                 135                 140

Ala Lys Pro Gly His Ala Val Phe Tyr Leu Leu Thr Ser Glu Gly Trp
145                 150                 155                 160

Ile Cys Val Asp Asp Lys Lys Ile Tyr Pro Glu Thr Pro Lys Thr Glu
                165                 170                 175

Asp Val Leu Val Phe Ala Pro Tyr Asp Phe Glu Ser Leu Gly Lys Asp
            180                 185                 190

Pro Pro Lys Leu His Gln Arg Tyr Glu Lys Ala Phe Glu Leu Ser Gly
        195                 200                 205

Gly Gly Thr Ser Thr Pro Thr Thr Gly Asn Gln Asn Met Ser Gly Asn
    210                 215                 220

Ser Gly Ser Ile Val Gln Asn Phe Tyr Met Gln Gln Tyr Gln Asn Ser
225                 230                 235                 240

Ile Asp Ala Asp Leu Gly Asp Asn Val Ile Ser Pro Glu Gly Gln Gly
                245                 250                 255
```

```
Ser Asn Thr Ser Ser Thr Ser Ser Gln Ser Ser Gly Leu Gly
         260                 265             270

Gly Trp Phe Ser Ser Leu Leu Asn Leu Gly Thr Lys Leu Leu Ala Asp
             275                 280             285

Lys Lys Thr Glu Glu Thr Thr Asn Ile Glu Asp Arg Ile Glu Thr Thr
         290                 295             300

Val Val Gly Val Thr Ile Ile Asn Ser Gln Gly Ser Val Gly Thr Thr
305                 310                 315                 320

Tyr Cys Tyr Ser Lys Pro Asp Gly Arg Pro Pro Ser Thr Val Ser Asp
                 325                 330                 335

Pro Val Thr Arg Leu Gly Pro Thr Leu Ser Arg His Tyr Thr Phe Lys
             340                 345             350

Val Gly Glu Trp Pro His Ser Gln Ser His Gly His Ala Trp Ile Cys
             355                 360             365

Pro Leu Pro Gly Asp Lys Leu Lys Lys Met Gly Ser Phe His Glu Val
         370                 375             380

Val Lys Ala His His Leu Val Lys Asn Gly Trp Asp Val Val Val Gln
385                 390                 395                 400

Val Asn Pro Ser Phe Ala His Ser Gly Pro Leu Cys Val Ala Ala Val
                 405                 410                 415

Pro Glu Tyr Glu His Thr His Glu Lys Ala Leu Lys Trp Ser Glu Leu
             420                 425             430

Glu Glu Pro Ala Tyr Thr Tyr Gln Gln Leu Ser Val Phe Pro His Gln
             435                 440             445

Leu Leu Asn Leu Arg Thr Asn Ser Ser Val His Leu Val Met Pro Tyr
         450                 455             460

Ile Gly Pro Gly Gln Pro Thr Asn Leu Thr Leu His Asn Pro Trp Thr
465                 470                 475                 480

Ile Val Ile Leu Ile Leu Ser Glu Leu Thr Gly Pro Gly Gln Thr Val
                 485                 490                 495

Pro Val Thr Met Ser Val Ala Pro Ile Asp Ala Met Val Asn Gly Pro
             500                 505             510

Leu Pro Asn Pro Glu Ala Pro Ile Arg Val Val Ser Val Pro Glu Ser
         515                 520             525

Asp Ser Phe Met Ser Ser Val Pro Asp Asn Ser Thr Pro Leu Tyr Pro
         530                 535             540

Lys Val Val Pro Pro Arg Gln Val Pro Gly Arg Phe Thr Asn Phe
545                 550                 555                 560

Ile Asp Val Ala Lys Gln Thr Tyr Ser Phe Cys Ser Ile Ser Gly Lys
                 565                 570             575

Pro Tyr Phe Glu Val Thr Asn Thr Ser Gly Asp Glu Pro Leu Phe Gln
             580                 585             590

Met Asp Val Ser Leu Ser Ala Ala Glu Leu His Gly Thr Tyr Val Ala
             595                 600             605

Ser Leu Ser Ser Phe Phe Ala Gln Tyr Arg Gly Ser Leu Asn Phe Asn
         610                 615             620

Phe Ile Phe Thr Gly Ala Ala Ala Thr Lys Ala Lys Phe Leu Val Ala
625                 630                 635                 640

Phe Val Pro Pro His Ser Ala Ala Pro Lys Thr Arg Asp Glu Ala Met
                 645                 650             655

Ala Cys Ile His Ala Val Trp Asp Val Gly Leu Asn Ser Ala Phe Ser
             660                 665             670

Phe Asn Val Pro Tyr Pro Ser Pro Ala Asp Phe Met Ala Val Tyr Ser
```

-continued

```
              675                 680                 685
Ala Glu Arg Thr Val Val Asn Val Ser Gly Trp Leu Gln Val Tyr Ala
    690                 695                 700
Leu Thr Ala Leu Thr Ser Thr Asp Ile Ala Val Asn Ser Lys Gly Arg
705                 710                 715                 720
Val Leu Val Ala Val Ser Ala Gly Pro Asp Phe Ser Leu Arg His Pro
                725                 730                 735
Ala Asp Leu Pro Asp Lys Gln Val Thr Asn Val Gly Glu Asp Gly Glu
            740                 745                 750
Pro Gly Glu Thr Glu Pro Arg His Ala Leu Ser Pro Val Asp Met His
        755                 760                 765
Val His Thr Asp Val Ser Phe Leu Leu Asp Arg Phe Asp Val Glu
    770                 775                 780
Thr Leu Glu Leu Ser Asn Leu Thr Gly Ser Pro Ala Thr His Val Leu
785                 790                 795                 800
Asp Pro Phe Gly Ser Thr Ala Gln Leu Ala Trp Ala Arg Leu Leu Asn
                805                 810                 815
Thr Cys Thr Tyr Phe Phe Ser Asp Leu Glu Leu Ser Ile Gln Phe Lys
            820                 825                 830
Phe Thr Thr Thr Pro Ser Ser Val Gly Glu Gly Phe Val Trp Val Lys
        835                 840                 845
Trp Leu Pro Val Gly Ala Pro Thr Lys Thr Thr Asp Ala Trp Gln Leu
    850                 855                 860
Glu Gly Gly Gly Asn Ser Val Arg Ile Gln Lys Leu Ala Val Ala Gly
865                 870                 875                 880
Met Cys Pro Thr Val Val Phe Lys Ile Ala Gly Ser Arg Ser Gln Ala
                885                 890                 895
Cys Ala Ser Ala Leu Pro Tyr Thr Ser Met Trp Arg Val Val Pro Val
            900                 905                 910
Phe Tyr Asn Gly Trp Gly Ala Pro Thr Lys Glu Lys Ala Thr Tyr Asn
        915                 920                 925
Trp Leu Pro Gly Ala His Phe Gly Ser Ile Leu Leu Thr Ser Asp Ala
    930                 935                 940
His Asp Lys Gly Gly Cys Tyr Leu Arg Tyr Ala Phe Arg Ala Pro Ala
945                 950                 955                 960
Met Tyr Cys Pro Arg Pro Ile Pro Pro Ala Phe Thr Arg Pro Ala Asp
                965                 970                 975
Lys Thr Arg His Lys Phe Pro Thr Asn Ile Asn Lys Gln Cys Thr Asn
            980                 985                 990
Tyr Ser Leu Leu Lys Leu Ala Gly Asp Val Glu Ser Asn Pro Gly Pro
        995                 1000                1005
Thr Ile Phe Ser Lys Ala Ser Ala Asp Leu Asn Ala Leu Ser Thr Ser
    1010                1015                1020
Leu Gly Glu Leu Thr Gly Met Leu Lys Asp Leu Lys Ala Lys Ala Glu
1025                1030                1035                1040
Thr Tyr Ser Pro Phe Tyr Lys Met Ala Lys Met Leu Phe Lys Leu Ala
                1045                1050                1055
Thr Leu Ala Val Ala Ala Met Arg Thr Lys Asp Pro Val Val Val
            1060                1065                1070
Met Leu Ile Ala Asp Phe Gly Leu Glu Val Phe Asp Thr Gly Phe Phe
        1075                1080                1085
Phe Ser Tyr Phe Gln Glu Lys Leu Gln Pro Tyr Met Lys Thr Ile Pro
    1090                1095                1100
```

-continued

```
Gly Lys Ile Ser Asp Leu Val Thr Asp Ala Ala Thr Ala Ala Ala Gln
1105                1110                1115                1120

Ile Pro Lys Gly Val Tyr Ser Phe Val Ser Ser Phe Glu Thr Pro
                1125                1130                1135

Glu Gly Val Val Glu Lys Gln Val Ser Leu Arg Thr Val Asn Asp Ile
                1140                1145                1150

Phe Ala Leu Leu Lys Asn Ser Asp Trp Phe Ile Lys Thr Leu Val Ala
                1155                1160                1165

Leu Lys Lys Trp Leu Thr Ser Trp Phe Ala Gln Glu Gln Gln Ala Asp
    1170                1175                1180

Asp Ala Leu Tyr Ser Glu Leu Glu Lys Tyr Pro Leu Tyr Lys Leu Lys
1185                1190                1195                1200

Leu Lys Glu Pro Asp Thr Gln Glu Glu Ala Arg Gln Trp Phe Lys Asp
                1205                1210                1215

Met Gln Gln Arg Ala Leu Ala Val Lys Asp Lys Gly Leu Phe Ser Leu
                1220                1225                1230

Leu Gln Ile Pro Leu Val Asn Leu Pro Gln Ser Arg Pro Glu Pro Val
    1235                1240                1245

Val Cys Val Leu Arg Gly Ala Ser Gly Gln Gly Lys Ser Tyr Leu Ala
1250                1255                1260

Asn Leu Met Ala Gln Ala Ile Ser Leu Leu Leu Val Gly Lys Gln Asp
1265                1270                1275                1280

Ser Val Trp Ser Cys Pro Pro Asp Pro Thr Tyr Phe Asp Gly Tyr Asn
                1285                1290                1295

Gly Gln Ala Val Val Ile Met Asp Ala Leu Gly Gln Asp Pro Asn Gly
                1300                1305                1310

Ala Asp Phe Lys Tyr Phe Cys Gln Met Val Ser Thr Thr Ala Phe Val
                1315                1320                1325

Pro Pro Met Ala His Leu Asp Asp Lys Gly Ile Pro Phe Thr Ser Pro
    1330                1335                1340

Val Val Ile Cys Thr Thr Asn Leu His Ser Ser Phe Thr Pro Ile Thr
1345                1350                1355                1360

Val Ser Cys Pro Glu Ala Leu Lys Arg Arg Phe Arg Phe Asp Val Thr
                1365                1370                1375

Val Ser Ala Lys Pro Gly Phe Val Arg Thr Val Gly Ser Asn Gln Leu
                1380                1385                1390

Leu Asn Leu Pro Leu Ala Leu Lys Pro Ala Gly Leu Pro Pro His Pro
    1395                1400                1405

Ile Phe Glu Asn Asp Met Pro Ile Ile Asn Gly Gln Ala Val Lys Leu
    1410                1415                1420

Ala Leu Ser Gly Gly Glu Val Thr Ala Phe Glu Leu Ile Glu Met Ile
1425                1430                1435                1440

Leu Ser Glu Val Gln Asn Arg Gln Asp Thr His Lys Met Pro Ile Phe
                1445                1450                1455

Lys Gln Ser Trp Ser Asp Leu Phe Arg Lys Cys Thr Thr Asp Glu Glu
                1460                1465                1470

Gln Lys Met Leu Gln Phe Leu Ile Asp Asn Lys Asp Ser Glu Ile Leu
    1475                1480                1485

Arg Ala Phe Val Ser Glu Arg Ser Ile Leu Leu His Glu Glu Tyr Leu
    1490                1495                1500

Lys Trp Glu Ser Tyr Met Thr Arg Arg Ala Lys Phe His Arg Leu Ala
1505                1510                1515                1520
```

-continued

```
Ala Asp Phe Ala Met Phe Leu Ser Ile Leu Thr Ser Leu Ile Val Ile
            1525                1530                1535

Phe Cys Leu Val Tyr Ser Met Tyr Gln Leu Phe Lys Thr Pro Asp Glu
        1540                1545                1550

Gln Ser Ala Tyr Asp Pro Ser Thr Lys Pro Lys Pro Lys Thr Gln Glu
        1555                1560                1565

Val Lys Thr Leu Lys Ile Arg Thr Glu Thr Gly Val Pro Ala Thr Asp
    1570                1575                1580

Leu Gln Gln Ser Ile Met Lys Asn Val Gln Pro Ile Glu Leu Tyr Leu
1585                1590                1595                1600

Asp Asn Glu Leu Val Thr Asp Cys Ser Ala Leu Gly Val Tyr Asp Asn
            1605                1610                1615

Ser Tyr Leu Val Pro Leu His Leu Phe Glu Phe Asp Phe Asp Thr Ile
            1620                1625                1630

Val Leu Gly Gly Arg His Tyr Lys Lys Ala Glu Cys Glu Lys Val Glu
            1635                1640                1645

Phe Glu Leu Glu Val Asn Gly Asp Val Val Ser Ser Asp Ala Cys Leu
        1650                1655                1660

Leu Arg Val Ser Ser Gly Pro Lys Val Arg Asn Ile Val His Leu Phe
1665                1670                1675                1680

Thr Asn Glu Ile Glu Leu Lys Lys Met Thr Gln Val Thr Gly Ile Met
            1685                1690                1695

Asn Ser Pro His Gln Ala Arg Thr Val Phe Phe Gly Ser Phe Leu Thr
        1700                1705                1710

Val Arg Lys Ser Ile Leu Thr Ser Asp Gly Thr Val Met Pro Asn Val
            1715                1720                1725

Leu Ser Tyr Ala Ala Gln Thr Ser Arg Gly Tyr Cys Gly Ala Ala Ile
    1730                1735                1740

Val Ala Gly Ser Pro Ala Arg Ile Ile Gly Ile His Ser Ala Gly Thr
1745                1750                1755                1760

Gly Ser Val Ala Phe Cys Ser Leu Val Ser Arg Asp Ala Leu Glu Gln
            1765                1770                1775

Leu Trp Pro Gln Lys Gln Gly Asn Val Ser Arg Leu Asp Asp Asp Val
        1780                1785                1790

Arg Val Ser Val Pro Arg Arg Ser Lys Leu Val Lys Ser Leu Ala Tyr
        1795                1800                1805

Pro Ile Phe Lys Pro Asp Tyr Gly Pro Ala Pro Leu Ser Gln Phe Asp
    1810                1815                1820

Lys Arg Leu Ser Asp Gly Val Lys Leu Asp Glu Val Val Phe Ala Lys
1825                1830                1835                1840

His Thr Gly Asp Lys Glu Ile Ser Ala Gln Asp Gln Lys Trp Leu Leu
            1845                1850                1855

Arg Ala Ala His Val Tyr Ala Gln Lys Val Phe Ser Arg Ile Gly Phe
        1860                1865                1870

Asp Asn Gln Ala Leu Thr Glu Lys Glu Ala Ile Cys Gly Ile Pro Gly
        1875                1880                1885

Leu Asp Lys Met Glu Gln Asp Thr Ala Pro Gly Leu Pro Tyr Ala Gln
    1890                1895                1900

Gln Asn Lys Arg Arg Lys Asp Ile Cys Asp Phe Glu Glu Gly Arg Leu
1905                1910                1915                1920

Lys Gly Ala Glu Leu Gln Lys Asp Arg Phe Met Ala Gly Asp Tyr Ser
            1925                1930                1935

Asn Leu Val Tyr Gln Ser Phe Leu Lys Asp Glu Ile Arg Pro Leu Glu
```

-continued

```
        1940                1945                1950

Lys Val Arg Ala Gly Lys Thr Arg Leu Ile Asp Val Pro Pro Met Pro
     1955                1960                1965

His Val Val Val Gly Arg Gln Leu Leu Gly Arg Phe Val Ala Lys Phe
   1970                1975                1980

His Glu Ala Asn Gly Phe Asp Ile Gly Ser Ala Ile Gly Cys Asp Pro
1985               1990                1995                2000

Asp Val Asp Trp Thr Arg Phe Gly Leu Glu Leu Glu Arg Phe Arg Tyr
               2005                2010                2015

Val Tyr Ala Cys Asp Tyr Ser Arg Phe Asp Ala Asn His Ala Ala Asp
           2020                2025                2030

Ala Met Arg Val Val Leu Asn Tyr Phe Phe Ser Glu Asp His Gly Phe
       2035                2040                2045

Asp Pro Gly Val Pro Ala Phe Ile Glu Ser Leu Val Asp Ser Val His
   2050                2055                2060

Ala Tyr Glu Glu Lys Arg Tyr Asn Ile Tyr Gly Gly Leu Pro Ser Gly
2065               2070                2075                2080

Cys Ser Cys Thr Ser Ile Leu Asn Thr Ile Leu Asn Asn Val Tyr Ile
               2085                2090                2095

Leu Ala Ala Met Met Lys Ala Tyr Glu Asn Phe Glu Pro Asp Asp Ile
           2100                2105                2110

Gln Val Ile Cys Tyr Gly Asp Asp Cys Leu Ile Ala Ser Asp Phe Glu
       2115                2120                2125

Ile Asp Phe Gln Gln Leu Val Pro Val Phe Ser Ser Phe Gly Gln Val
   2130                2135                2140

Ile Thr Thr Ala Asp Lys Thr Asp Phe Phe Lys Leu Thr Thr Leu Ser
2145               2150                2155                2160

Glu Val Thr Phe Leu Lys Arg Ala Phe Val Leu Thr Ala Phe Tyr Lys
               2165                2170                2175

Pro Val Met Asp Val Lys Thr Leu Glu Ala Ile Leu Ser Phe Val Arg
           2180                2185                2190

Pro Gly Thr Gln Ala Glu Lys Leu Leu Ser Val Ala Gln Leu Ala Gly
       2195                2200                2205

His Cys Glu Pro Glu Gln Tyr Glu Arg Leu Phe Glu Pro Phe Ala Gly
   2210                2215                2220

Met Tyr Phe Val Pro Thr Trp Arg
2225               2230
```